(12) United States Patent
Takahashi

(10) Patent No.: US 9,034,328 B2
(45) Date of Patent: May 19, 2015

(54) ANTI-ERBB3 ANTIBODY

(75) Inventor: Nobuaki Takahashi, Tokyo (JP)

(73) Assignee: KYOWA HAKKO KIRIN CO., LTD, Tokyo (JP)

( * ) Notice: Subject to any disclaimer, the term of this patent is extended or adjusted under 35 U.S.C. 154(b) by 0 days.

(21) Appl. No.: 13/527,733

(22) Filed: Jun. 20, 2012

(65) Prior Publication Data

US 2012/0328623 A1    Dec. 27, 2012

Related U.S. Application Data

(60) Provisional application No. 61/498,732, filed on Jun. 20, 2011.

(51) Int. Cl.
*A61K 39/395* (2006.01)
*C07K 16/32* (2006.01)
*A61K 39/00* (2006.01)

(52) U.S. Cl.
CPC ............ *C07K 16/32* (2013.01); *A61K 39/39558* (2013.01); *A61K 2039/505* (2013.01); *A61K 2039/507* (2013.01); *C07K 2317/24* (2013.01); *C07K 2317/76* (2013.01)

(58) Field of Classification Search
None
See application file for complete search history.

(56) References Cited

U.S. PATENT DOCUMENTS 7,705,130 B2 * 4/2010 Rothe et al. ................. 530/387.1
7,846,440 B2 * 12/2010 Schoeberl et al. ......... 424/141.1

2004/0197332 A1   10/2004 Ullrich et al.
2008/0124345 A1    5/2008 Rothe et al.
2009/0291085 A1   11/2009 Schoeberl et al.
2010/0256340 A1   10/2010 Brinkmann et al.
2012/0107306 A1 *  5/2012 Elis et al. ................... 424/133.1

FOREIGN PATENT DOCUMENTS

| JP | 2005504044 A | | 2/2005 |
| JP | 2009521913 A | | 6/2009 |
| JP | 2010518820 A | | 6/2010 |
| WO | WO 2007/077028 | * | 7/2007 |
| WO | WO 2008/100624 | * | 8/2008 |
| WO | 2011022727 A2 | | 2/2011 |

OTHER PUBLICATIONS

Chen, et al., "An Immunological Approach Reveals Biological Differences between the Two NDF/Heregulin Receptors, ErbB-3 and ErbB-4", The Journal of Biological Chemistry, 1996, vol. 271, No. 13, pp. 7620-7629.
Sala, et al., "An ErbB-3 antibody, MP-RM-1, inhibits tumor growth by blocking ligand-dependent and independent activation of ErbB-3/Akt signaling", Oncogene, Aug. 8, 2012, 19 pgs total.
Jose Baselga et al., "Novel anticancer targets: Revisiting ERBB2 and discovering ERBB3", Nature Reviews, vol. 9, Jul. 2009, p. 463-475.

* cited by examiner

*Primary Examiner* — Marianne P Allen
(74) *Attorney, Agent, or Firm* — Sughrue Mion, PLLC

(57) ABSTRACT

The present invention relates to an antibody or an antibody fragment thereof which recognizes an extracellular domain of erbB3 and inhibit EGF-like ligand-dependent phosphorylation of erbB3, a DNA encoding the antibody or the antibody fragment thereof, a method of producing the antibody or the antibody fragment thereof, a therapeutic drug including the antibody or the antibody fragment thereof, and therapeutic application using the antibody or the antibody fragment thereof.

14 Claims, 6 Drawing Sheets

SEQUENCE LISTING

<160> NUMBER OF SEQ ID NOS: 100

<210> SEQ ID NO 1
<211> LENGTH: 5765
<212> TYPE: DNA
<213> ORGANISM: Homo sapiens
<220> FEATURE:
<221> NAME/KEY: CDS
<222> LOCATION: (277)..(4305)

<400> SEQUENCE: 1

| | | |
|---|---|---|
| actccagcct cgcgcgggag ggggcgcggc cgtgactcac ccccttccct ctgcgttcct | 60 | |
| ccctccctct ctctctctct ctcacacaca cacacccctc ccctgccatc cctcccggga | 120 | |
| ctccggctcc ggctccgatt gcaatttgca acctccgctg ccgtcgccgc agcagccacc | 180 | |
| aattcgccag cggttcaggt ggctcttgcc tcgatgtcct agcctagggg ccccgggcc | 240 | |
| ggacttggct gggctccctt caccctctgc ggagtc atg agg gcg aac gac gct | 294 |
| | Met Arg Ala Asn Asp Ala | |
| | 1 5 | |
| ctg cag gtg ctg ggc ttg ctt ttc agc ctg gcc cgg ggc tcc gag gtg | 342 |
| Leu Gln Val Leu Gly Leu Leu Phe Ser Leu Ala Arg Gly Ser Glu Val | |
| 10 15 20 | |
| ggc aac tct cag gca gtg tgt cct ggg act ctg aat ggc ctg agt gtg | 390 |
| Gly Asn Ser Gln Ala Val Cys Pro Gly Thr Leu Asn Gly Leu Ser Val | |
| 25 30 35 | |
| acc ggc gat gct gag aac caa tac cag aca ctg tac aag ctc tac gag | 438 |
| Thr Gly Asp Ala Glu Asn Gln Tyr Gln Thr Leu Tyr Lys Leu Tyr Glu | |
| 40 45 50 | |
| agg tgt gag gtg gtg atg ggg aac ctt gag att gtg ctc acg gga cac | 486 |
| Arg Cys Glu Val Val Met Gly Asn Leu Glu Ile Val Leu Thr Gly His | |
| 55 60 65 70 | |
| aat gcc gac ctc tcc ttc ctg cag tgg att cga gaa gtg aca ggc tat | 534 |
| Asn Ala Asp Leu Ser Phe Leu Gln Trp Ile Arg Glu Val Thr Gly Tyr | |
| 75 80 85 | |
| gtc ctc gtg gcc atg aat gaa ttc tct act cta cca ttg ccc aac ctc | 582 |
| Val Leu Val Ala Met Asn Glu Phe Ser Thr Leu Pro Leu Pro Asn Leu | |
| 90 95 100 | |
| cgc gtg gtg cga ggg acc cag gtc tac gat ggg aag ttt gcc atc ttc | 630 |
| Arg Val Val Arg Gly Thr Gln Val Tyr Asp Gly Lys Phe Ala Ile Phe | |
| 105 110 115 | |
| gtc atg ttg aac tat aac acc aac tcc agc cac gct ctg cgc cag ctc | 678 |
| Val Met Leu Asn Tyr Asn Thr Asn Ser Ser His Ala Leu Arg Gln Leu | |
| 120 125 130 | |
| cgc ttg act cag ctc acc gag att ctg tca ggg ggt gtt tat att gag | 726 |
| Arg Leu Thr Gln Leu Thr Glu Ile Leu Ser Gly Gly Val Tyr Ile Glu | |
| 135 140 145 150 | |
| aag aac gat aag ctt tgt cac atg gac aca att gac tgg agg gac atc | 774 |
| Lys Asn Asp Lys Leu Cys His Met Asp Thr Ile Asp Trp Arg Asp Ile | |
| 155 160 165 | |
| gtg agg gac cga gat gct gag ata gtg gtg aag gac aat ggc aga agc | 822 |
| Val Arg Asp Arg Asp Ala Glu Ile Val Val Lys Asp Asn Gly Arg Ser | |
| 170 175 180 | |
| tgt ccc ccc tgt cat gag gtt tgc aag ggg cga tgc tgg ggt cct gga | 870 |
| Cys Pro Pro Cys His Glu Val Cys Lys Gly Arg Cys Trp Gly Pro Gly | |
| 185 190 195 | |
| tca gaa gac tgc cag aca ttg acc aag acc atc tgt gct cct cag tgt | 918 |
| Ser Glu Asp Cys Gln Thr Leu Thr Lys Thr Ile Cys Ala Pro Gln Cys | |
| 200 205 210 | |
| aat ggt cac tgc ttt ggg ccc aac ccc aac cag tgc tgc cat gat gag | 966 |
| Asn Gly His Cys Phe Gly Pro Asn Pro Asn Gln Cys Cys His Asp Glu | |

```
                215                 220                 225                 230
tgt gcc ggg ggc tgc tca ggc cct cag gac aca gac tgc ttt gcc tgc       1014
Cys Ala Gly Gly Cys Ser Gly Pro Gln Asp Thr Asp Cys Phe Ala Cys
                    235                 240                 245 cgg cac ttc aat gac agt gga gcc tgt gta cct cgc tgt cca cag cct       1062
Arg His Phe Asn Asp Ser Gly Ala Cys Val Pro Arg Cys Pro Gln Pro
            250                 255                 260 ctt gtc tac aac aag cta act ttc cag ctg gaa ccc aat ccc cac acc       1110
Leu Val Tyr Asn Lys Leu Thr Phe Gln Leu Glu Pro Asn Pro His Thr
        265                 270                 275 aag tat cag tat gga gga gtt tgt gta gcc agc tgt ccc cat aac ttt       1158
Lys Tyr Gln Tyr Gly Gly Val Cys Val Ala Ser Cys Pro His Asn Phe
    280                 285                 290 gtg gtg gat caa aca tcc tgt gtc agg gcc tgt cct cct gac aag atg       1206
Val Val Asp Gln Thr Ser Cys Val Arg Ala Cys Pro Pro Asp Lys Met
295                 300                 305                 310 gaa gta gat aaa aat ggg ctc aag atg tgt gag cct tgt ggg gga cta       1254
Glu Val Asp Lys Asn Gly Leu Lys Met Cys Glu Pro Cys Gly Gly Leu
                    315                 320                 325 tgt ccc aaa gcc tgt gag gga aca ggc tct ggg agc cgc ttc cag act       1302
Cys Pro Lys Ala Cys Glu Gly Thr Gly Ser Gly Ser Arg Phe Gln Thr
                330                 335                 340 gtg gac tcg agc aac att gat gga ttt gtg aac tgc acc aag atc ctg       1350
Val Asp Ser Ser Asn Ile Asp Gly Phe Val Asn Cys Thr Lys Ile Leu
            345                 350                 355 ggc aac ctg gac ttt ctg atc acc ggc ctc aat gga gac ccc tgg cac       1398
Gly Asn Leu Asp Phe Leu Ile Thr Gly Leu Asn Gly Asp Pro Trp His
        360                 365                 370 aag atc cct gcc ctg gac cca gag aag ctc aat gtc ttc cgg aca gta       1446
Lys Ile Pro Ala Leu Asp Pro Glu Lys Leu Asn Val Phe Arg Thr Val
375                 380                 385                 390 cgg gag atc aca ggt tac ctg aac atc cag tcc tgg ccg ccc cac atg       1494
Arg Glu Ile Thr Gly Tyr Leu Asn Ile Gln Ser Trp Pro Pro His Met
                    395                 400                 405 cac aac ttc agt gtt ttt tcc aat ttg aca acc att gga ggc aga agc       1542
His Asn Phe Ser Val Phe Ser Asn Leu Thr Thr Ile Gly Gly Arg Ser
                410                 415                 420 ctc tac aac cgg ggc ttc tca ttg ttg atc atg aag aac ttg aat gtc       1590
Leu Tyr Asn Arg Gly Phe Ser Leu Leu Ile Met Lys Asn Leu Asn Val
            425                 430                 435 aca tct ctg ggc ttc cga tcc ctg aag gaa att agt gct ggg cgt atc       1638
Thr Ser Leu Gly Phe Arg Ser Leu Lys Glu Ile Ser Ala Gly Arg Ile
        440                 445                 450 tat ata agt gcc aat agg cag ctc tgc tac cac cac tct ttg aac tgg       1686
Tyr Ile Ser Ala Asn Arg Gln Leu Cys Tyr His His Ser Leu Asn Trp
455                 460                 465                 470 acc aag gtg ctt cgg ggg cct acg gaa gag cga cta gac atc aag cat       1734
Thr Lys Val Leu Arg Gly Pro Thr Glu Glu Arg Leu Asp Ile Lys His
                    475                 480                 485 aat cgg ccg cgc aga gac tgc gtg gca gag ggc aaa gtg tgt gac cca       1782
Asn Arg Pro Arg Arg Asp Cys Val Ala Glu Gly Lys Val Cys Asp Pro
                490                 495                 500 ctg tgc tcc tct ggg gga tgc tgg ggc cca ggc cct ggt cag tgc ttg       1830
Leu Cys Ser Ser Gly Gly Cys Trp Gly Pro Gly Pro Gly Gln Cys Leu
            505                 510                 515 tcc tgt cga aat tat agc cga gga ggt gtc tgt gtg acc cac tgc aac       1878
Ser Cys Arg Asn Tyr Ser Arg Gly Gly Val Cys Val Thr His Cys Asn
        520                 525                 530 ttt ctg aat ggg gag cct cga gaa ttt gcc cat gag gcc gaa tgc ttc       1926
```

```
Phe Leu Asn Gly Glu Pro Arg Glu Phe Ala His Glu Ala Glu Cys Phe
535                 540                 545                 550 tcc tgc cac ccg gaa tgc caa ccc atg gag ggc act gcc aca tgc aat      1974
Ser Cys His Pro Glu Cys Gln Pro Met Glu Gly Thr Ala Thr Cys Asn
                555                 560                 565 ggc tcg ggc tct gat act tgt gct caa tgt gcc cat ttt cga gat ggg      2022
Gly Ser Gly Ser Asp Thr Cys Ala Gln Cys Ala His Phe Arg Asp Gly
            570                 575                 580 ccc cac tgt gtg agc agc tgc ccc cat gga gtc cta ggt gcc aag ggc      2070
Pro His Cys Val Ser Ser Cys Pro His Gly Val Leu Gly Ala Lys Gly
        585                 590                 595 cca atc tac aag tac cca gat gtt cag aat gaa tgt cgg ccc tgc cat      2118
Pro Ile Tyr Lys Tyr Pro Asp Val Gln Asn Glu Cys Arg Pro Cys His
    600                 605                 610 gag aac tgc acc cag ggg tgt aaa gga cca gag ctt caa gac tgt tta      2166
Glu Asn Cys Thr Gln Gly Cys Lys Gly Pro Glu Leu Gln Asp Cys Leu
615                 620                 625                 630 gga caa aca ctg gtg ctg atc ggc aaa acc cat ctg aca atg gct ttg      2214
Gly Gln Thr Leu Val Leu Ile Gly Lys Thr His Leu Thr Met Ala Leu
                635                 640                 645 aca gtg ata gca gga ttg gta gtg att ttc atg atg ctg ggc ggc act      2262
Thr Val Ile Ala Gly Leu Val Val Ile Phe Met Met Leu Gly Gly Thr
            650                 655                 660 ttt ctc tac tgg cgt ggg cgc cgg att cag aat aaa agg gct atg agg      2310
Phe Leu Tyr Trp Arg Gly Arg Arg Ile Gln Asn Lys Arg Ala Met Arg
        665                 670                 675 cga tac ttg gaa cgg ggt gag agc ata gag cct ctg gac ccc agt gag      2358
Arg Tyr Leu Glu Arg Gly Glu Ser Ile Glu Pro Leu Asp Pro Ser Glu
    680                 685                 690 aag gct aac aaa gtc ttg gcc aga atc ttc aaa gag aca gag cta agg      2406
Lys Ala Asn Lys Val Leu Ala Arg Ile Phe Lys Glu Thr Glu Leu Arg
695                 700                 705                 710 aag ctt aaa gtg ctt ggc tcg ggt gtc ttt gga act gtg cac aaa gga      2454
Lys Leu Lys Val Leu Gly Ser Gly Val Phe Gly Thr Val His Lys Gly
                715                 720                 725 gtg tgg atc cct gag ggt gaa tca atc aag att cca gtc tgc att aaa      2502
Val Trp Ile Pro Glu Gly Glu Ser Ile Lys Ile Pro Val Cys Ile Lys
            730                 735                 740 gtc att gag gac aag agt gga cgg cag agt ttt caa gct gtg aca gat      2550
Val Ile Glu Asp Lys Ser Gly Arg Gln Ser Phe Gln Ala Val Thr Asp
        745                 750                 755 cat atg ctg gcc att ggc agc ctg gac cat gcc cac att gta agg ctg      2598
His Met Leu Ala Ile Gly Ser Leu Asp His Ala His Ile Val Arg Leu
    760                 765                 770 ctg gga cta tgc cca ggg tca tct ctg cag ctt gtc act caa tat ttg      2646
Leu Gly Leu Cys Pro Gly Ser Ser Leu Gln Leu Val Thr Gln Tyr Leu
775                 780                 785                 790 cct ctg ggt tct ctg ctg gat cat gtg aga caa cac cgg ggg gca ctg      2694
Pro Leu Gly Ser Leu Leu Asp His Val Arg Gln His Arg Gly Ala Leu
                795                 800                 805 ggg cca cag ctg ctg ctc aac tgg gga gta caa att gcc aag gga atg      2742
Gly Pro Gln Leu Leu Leu Asn Trp Gly Val Gln Ile Ala Lys Gly Met
            810                 815                 820 tac tac ctt gag gaa cat ggt atg gtg cat aga aac ctg gct gcc cga      2790
Tyr Tyr Leu Glu Glu His Gly Met Val His Arg Asn Leu Ala Ala Arg
        825                 830                 835 aac gtg cta ctc aag tca ccc agt cag gtt cag gtg gca gat ttt ggt      2838
Asn Val Leu Leu Lys Ser Pro Ser Gln Val Gln Val Ala Asp Phe Gly
    840                 845                 850
```

-continued

| | |
|---|---|
| gtg gct gac ctg ctg cct cct gat gat aag cag ctg cta tac agt gag<br>Val Ala Asp Leu Leu Pro Pro Asp Asp Lys Gln Leu Leu Tyr Ser Glu<br>855                            860                   865                 870 | 2886 |
| gcc aag act cca att aag tgg atg gcc ctt gag agt atc cac ttt ggg<br>Ala Lys Thr Pro Ile Lys Trp Met Ala Leu Glu Ser Ile His Phe Gly<br>               875                   880                   885 | 2934 |
| aaa tac aca cac cag agt gat gtc tgg agc tat ggt gtg aca gtt tgg<br>Lys Tyr Thr His Gln Ser Asp Val Trp Ser Tyr Gly Val Thr Val Trp<br>890                     895                   900 | 2982 |
| gag ttg atg acc ttc ggg gca gag ccc tat gca ggg cta cga ttg gct<br>Glu Leu Met Thr Phe Gly Ala Glu Pro Tyr Ala Gly Leu Arg Leu Ala<br>               905                   910                   915 | 3030 |
| gaa gta cca gac ctg cta gag aag ggg gag cgg ttg gca cag ccc cag<br>Glu Val Pro Asp Leu Leu Glu Lys Gly Glu Arg Leu Ala Gln Pro Gln<br>920                            925                   930 | 3078 |
| atc tgc aca att gat gtc tac atg gtg atg gtc aag tgt tgg atg att<br>Ile Cys Thr Ile Asp Val Tyr Met Val Met Val Lys Cys Trp Met Ile<br>935                            940                   945                 950 | 3126 |
| gat gag aac att cgc cca acc ttt aaa gaa cta gcc aat gag ttc acc<br>Asp Glu Asn Ile Arg Pro Thr Phe Lys Glu Leu Ala Asn Glu Phe Thr<br>               955                   960                   965 | 3174 |
| agg atg gcc cga gac cca cca cgg tat ctg gtc ata aag aga gag agt<br>Arg Met Ala Arg Asp Pro Pro Arg Tyr Leu Val Ile Lys Arg Glu Ser<br>970                            975                   980 | 3222 |
| ggg cct gga ata gcc cct ggg cca gag ccc cat ggt ctg aca aac aag<br>Gly Pro Gly Ile Ala Pro Gly Pro Glu Pro His Gly Leu Thr Asn Lys<br>               985                   990                   995 | 3270 |
| aag cta gag gaa gta gag ctg gag cca gaa cta gac cta gac cta<br>Lys Leu Glu Glu Val Glu Leu Glu Pro Glu Leu Asp Leu Asp Leu<br>1000                   1005                 1010 | 3315 |
| gac ttg gaa gca gag gag gac aac ctg gca acc acc aca ctg ggc<br>Asp Leu Glu Ala Glu Glu Asp Asn Leu Ala Thr Thr Thr Leu Gly<br>              1015                 1020                 1025 | 3360 |
| tcc gcc ctc agc cta cca gtt gga aca ctt aat cgg cca cgt ggg<br>Ser Ala Leu Ser Leu Pro Val Gly Thr Leu Asn Arg Pro Arg Gly<br>1030                   1035                 1040 | 3405 |
| agc cag agc ctt tta agt cca tca tct gga tac atg ccc atg aac<br>Ser Gln Ser Leu Leu Ser Pro Ser Ser Gly Tyr Met Pro Met Asn<br>              1045                 1050                 1055 | 3450 |
| cag ggt aat ctt ggg gag tct tgc cag gag tct gca gtt tct ggg<br>Gln Gly Asn Leu Gly Glu Ser Cys Gln Glu Ser Ala Val Ser Gly<br>1060                   1065                 1070 | 3495 |
| agc agt gaa cgg tgc ccc cgt cca gtc tct cta cac cca atg cca<br>Ser Ser Glu Arg Cys Pro Arg Pro Val Ser Leu His Pro Met Pro<br>              1075                 1080                 1085 | 3540 |
| cgg gga tgc ctg gca tca gag tca tca gag ggg cat gta aca ggc<br>Arg Gly Cys Leu Ala Ser Glu Ser Ser Glu Gly His Val Thr Gly<br>1090                   1095                 1100 | 3585 |
| tct gag gct gag ctc cag gag aaa gtg tca atg tgt agg agc cgg<br>Ser Glu Ala Glu Leu Gln Glu Lys Val Ser Met Cys Arg Ser Arg<br>1105                   1110                 1115 | 3630 |
| agc agg agc cgg agc cca cgg cca cgc gga gat agc gcc tac cat<br>Ser Arg Ser Arg Ser Pro Arg Pro Arg Gly Asp Ser Ala Tyr His<br>              1120                 1125                 1130 | 3675 |
| tcc cag cgc cac agt ctg ctg act cct gtt acc cca ctc tcc cca<br>Ser Gln Arg His Ser Leu Leu Thr Pro Val Thr Pro Leu Ser Pro<br>1135                   1140                 1145 | 3720 |
| ccc ggg tta gag gaa gag gat gtc aac ggt tat gtc atg cca gat<br>Pro Gly Leu Glu Glu Glu Asp Val Asn Gly Tyr Val Met Pro Asp<br>              1150                 1155                 1160 | 3765 |

| | | | | | | | | | | | |
|---|---|---|---|---|---|---|---|---|---|---|---|
| aca | cac | ctc | aaa | ggt | act | ccc | tcc | tcc | cgg | gaa | ggc | acc | ctt | tct | 3810 |
| Thr | His | Leu | Lys | Gly | Thr | Pro | Ser | Ser | Arg | Glu | Gly | Thr | Leu | Ser | |
| | 1165 | | | | 1170 | | | | | 1175 | | | | | |
| tca | gtg | ggt | ctc | agt | tct | gtc | ctg | ggt | act | gaa | gaa | gaa | gat | gaa | 3855 |
| Ser | Val | Gly | Leu | Ser | Ser | Val | Leu | Gly | Thr | Glu | Glu | Glu | Asp | Glu | |
| | 1180 | | | | 1185 | | | | | 1190 | | | | | |
| gat | gag | gag | tat | gaa | tac | atg | aac | cgg | agg | aga | agg | cac | agt | cca | 3900 |
| Asp | Glu | Glu | Tyr | Glu | Tyr | Met | Asn | Arg | Arg | Arg | Arg | His | Ser | Pro | |
| | 1195 | | | | 1200 | | | | | 1205 | | | | | |
| cct | cat | ccc | cct | agg | cca | agt | tcc | ctt | gag | gag | ctg | ggt | tat | gag | 3945 |
| Pro | His | Pro | Pro | Arg | Pro | Ser | Ser | Leu | Glu | Glu | Leu | Gly | Tyr | Glu | |
| | 1210 | | | | 1215 | | | | | 1220 | | | | | |
| tac | atg | gat | gtg | ggg | tca | gac | ctc | agt | gcc | tct | ctg | ggc | agc | aca | 3990 |
| Tyr | Met | Asp | Val | Gly | Ser | Asp | Leu | Ser | Ala | Ser | Leu | Gly | Ser | Thr | |
| | 1225 | | | | 1230 | | | | | 1235 | | | | | |
| cag | agt | tgc | cca | ctc | cac | cct | gta | ccc | atc | atg | ccc | act | gca | ggc | 4035 |
| Gln | Ser | Cys | Pro | Leu | His | Pro | Val | Pro | Ile | Met | Pro | Thr | Ala | Gly | |
| | 1240 | | | | 1245 | | | | | 1250 | | | | | |
| aca | act | cca | gat | gaa | gac | tat | gaa | tat | atg | aat | cgg | caa | cga | gat | 4080 |
| Thr | Thr | Pro | Asp | Glu | Asp | Tyr | Glu | Tyr | Met | Asn | Arg | Gln | Arg | Asp | |
| | 1255 | | | | 1260 | | | | | 1265 | | | | | |
| gga | ggt | ggt | cct | ggg | ggt | gat | tat | gca | gcc | atg | ggg | gcc | tgc | cca | 4125 |
| Gly | Gly | Gly | Pro | Gly | Gly | Asp | Tyr | Ala | Ala | Met | Gly | Ala | Cys | Pro | |
| | 1270 | | | | 1275 | | | | | 1280 | | | | | |
| gca | tct | gag | caa | ggg | tat | gaa | gag | atg | aga | gct | ttt | cag | ggg | cct | 4170 |
| Ala | Ser | Glu | Gln | Gly | Tyr | Glu | Glu | Met | Arg | Ala | Phe | Gln | Gly | Pro | |
| | 1285 | | | | 1290 | | | | | 1295 | | | | | |
| gga | cat | cag | gcc | ccc | cat | gtc | cat | tat | gcc | cgc | cta | aaa | act | cta | 4215 |
| Gly | His | Gln | Ala | Pro | His | Val | His | Tyr | Ala | Arg | Leu | Lys | Thr | Leu | |
| | 1300 | | | | 1305 | | | | | 1310 | | | | | |
| cgt | agc | tta | gag | gct | aca | gac | tct | gcc | ttt | gat | aac | cct | gat | tac | 4260 |
| Arg | Ser | Leu | Glu | Ala | Thr | Asp | Ser | Ala | Phe | Asp | Asn | Pro | Asp | Tyr | |
| | 1315 | | | | 1320 | | | | | 1325 | | | | | |
| tgg | cat | agc | agg | ctt | ttc | ccc | aag | gct | aat | gcc | cag | aga | acg | taa | 4305 |
| Trp | His | Ser | Arg | Leu | Phe | Pro | Lys | Ala | Asn | Ala | Gln | Arg | Thr | | |
| | 1330 | | | | 1335 | | | | | 1340 | | | | | |

| | | |
|---|---|---|
| ctcctgctcc ctgtggcact cagggagcat ttaatggcag ctagtgcctt tagagggtac | 4365 |
| cgtcttctcc ctattccctc tctctcccag gtcccagccc cttttcccca gtcccagaca | 4425 |
| attccattca atctttggag cttttaaac attttgacac aaaattctta tggtatgtag | 4485 |
| ccagctgtgc actttcttct ctttcccaac cccaggaaag gttttccta ttttgtgtgc | 4545 |
| tttcccagtc ccattcctca gcttcttcac aggcactcct ggagatatga aggattactc | 4605 |
| tccatatccc ttcctctcag gctcttgact acttggaact aggctcttat gtgtgccttt | 4665 |
| gtttcccatc agactgtcaa gaagaggaaa gggaggaaac ctagcagagg aaagtgtaat | 4725 |
| tttggtttat gactcttaac cccctagaaa gacagaagct taaaatctgt gaagaaagag | 4785 |
| gttaggagta gatattgatt actatcataa ttcagcactt aactatgagc caggcatcat | 4845 |
| actaaacttc acctacatta tctcacttag tcctttatca tccttaaaac aattctgtga | 4905 |
| catacatatt atctcatttt acacaaaggg aagtcgggca tggtggctca tgcctgtaat | 4965 |
| ctcagcactt tgggaggctg aggcagaagg attacctgag gcaaggagtt tgagaccagc | 5025 |
| ttagccaaca tagtaagacc cccatctctt taaaaaaaaa aaaaaaaaa aaaaaaaac | 5085 |
| tttgaaactg ggtgcagtgg ctcatgcctg taatcccagc cagcactttg ggaggctgag | 5145 |
| atgggaagat cacttgagcc cagaattaga gataagccta tggaaacata gcaagacact | 5205 |

-continued

```
gtctctacag gggaaaaaaa aaaagaaac tgagccttaa agagatgaaa taaattaagc   5265
agtagatcca ggatgcaaaa tcctcccaat tcctgtgcat gtgctcttat tgtaaggtgc   5325
caagaaaaac tgatttaagt tacagccctt gtttaagggg cactgtttct tgttttttgca  5385 ctgaatcaag tctaacccca acagccacat cctcctatac ctagacatct catctcagga   5445
agtggtggtg ggggtagtca gaaggaaaaa taactggaca tctttgtgta aaccataatc   5505
cacatgtgcc gtaaatgatc ttcactcctt atccgagggc aaattcacaa ggatccccaa   5565
gatccacttt tagaagccat tctcatccag cagtgagaag cttccaggta ggacagaaaa   5625
aagatccagc ttcagctgca cacctctgtc cccttggatg gggaactaag ggaaaacgtc   5685
tgttgtatca ctgaagtttt tgttttgtt tttatacgtg tctgaataaa aatgccaaag    5745
ttttttttca gcaaaaaaaa                                                5765
```

<210> SEQ ID NO 2
<211> LENGTH: 1342
<212> TYPE: PRT
<213> ORGANISM: Homo sapiens

<400> SEQUENCE: 2

```
Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270
```

```
Glu Pro Asn Pro His Thr Lys Tyr Gln Tyr Gly Val Cys Val Ala
            275                 280                 285

Ser Cys Pro His Asn Phe Val Val Asp Gln Thr Ser Cys Val Arg Ala
290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
                340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
                420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
            515                 520                 525

Cys Val Thr His Cys Asn Phe Leu Asn Gly Glu Pro Arg Glu Phe Ala
530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
                580                 585                 590

Val Leu Gly Ala Lys Gly Pro Ile Tyr Lys Tyr Pro Asp Val Gln Asn
            595                 600                 605

Glu Cys Arg Pro Cys His Glu Asn Cys Thr Gln Gly Cys Lys Gly Pro
610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
                660                 665                 670

Asn Lys Arg Ala Met Arg Arg Tyr Leu Glu Arg Gly Glu Ser Ile Glu
            675                 680                 685

Pro Leu Asp Pro Ser Glu Lys Ala Asn Lys Val Leu Ala Arg Ile Phe
```

```
            690             695             700
Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
    770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
                820                 825                 830

Arg Asn Leu Ala Ala Arg Asn Val Leu Leu Lys Ser Pro Ser Gln Val
            835                 840                 845

Gln Val Ala Asp Phe Gly Val Ala Asp Leu Leu Pro Pro Asp Asp Lys
        850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
                900                 905                 910

Ala Gly Leu Arg Leu Ala Glu Val Pro Asp Leu Leu Glu Lys Gly Glu
            915                 920                 925

Arg Leu Ala Gln Pro Gln Ile Cys Thr Ile Asp Val Tyr Met Val Met
        930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
            980                 985                 990

His Gly Leu Thr Asn Lys Lys Leu  Glu Glu Val Glu Leu  Glu Pro Glu
        995                 1000                1005

Leu Asp  Leu Asp Leu Asp  Leu  Glu Ala Glu Glu Asp   Asn Leu Ala
    1010                1015                1020

Thr Thr  Thr Leu Gly Ser Ala  Leu Ser Leu Pro Val  Gly Thr Leu
    1025                1030                1035

Asn Arg  Pro Arg Gly Ser Gln  Ser Leu Leu Ser Pro  Ser Ser Gly
    1040                1045                1050

Tyr Met  Pro Met Asn Gln Gly  Asn Leu Gly Glu Ser  Cys Gln Glu
    1055                1060                1065

Ser Ala  Val Ser Gly Ser Ser  Glu Arg Cys Pro Arg  Pro Val Ser
    1070                1075                1080

Leu His  Pro Met Pro Arg Gly  Cys Leu Ala Ser Glu  Ser Ser Glu
    1085                1090                1095

Gly His  Val Thr Gly Ser Glu  Ala Glu Leu Gln Glu  Lys Val Ser
    1100                1105                1110
```

-continued

```
Met Cys Arg Ser Arg Ser Arg Ser Arg Pro Arg Pro Arg Gly
    1115                1120                1125

Asp Ser Ala Tyr His Ser Gln Arg His Ser Leu Leu Thr Pro Val
    1130                1135                1140

Thr Pro Leu Ser Pro Pro Gly Leu Glu Glu Glu Asp Val Asn Gly
    1145                1150                1155

Tyr Val Met Pro Asp Thr His Leu Lys Gly Thr Pro Ser Ser Arg
    1160                1165                1170

Glu Gly Thr Leu Ser Ser Val Gly Leu Ser Ser Val Leu Gly Thr
    1175                1180                1185

Glu Glu Glu Asp Glu Asp Glu Tyr Glu Tyr Met Asn Arg Arg
    1190                1195                1200

Arg Arg His Ser Pro Pro His Pro Pro Arg Pro Ser Ser Leu Glu
    1205                1210                1215

Glu Leu Gly Tyr Glu Tyr Met Asp Val Gly Ser Asp Leu Ser Ala
    1220                1225                1230

Ser Leu Gly Ser Thr Gln Ser Cys Pro Leu His Pro Val Pro Ile
    1235                1240                1245

Met Pro Thr Ala Gly Thr Thr Pro Asp Glu Asp Tyr Glu Tyr Met
    1250                1255                1260

Asn Arg Gln Arg Asp Gly Gly Gly Pro Gly Gly Asp Tyr Ala Ala
    1265                1270                1275

Met Gly Ala Cys Pro Ala Ser Glu Gln Gly Tyr Glu Glu Met Arg
    1280                1285                1290

Ala Phe Gln Gly Pro Gly His Gln Ala Pro His Val His Tyr Ala
    1295                1300                1305

Arg Leu Lys Thr Leu Arg Ser Leu Glu Ala Thr Asp Ser Ala Phe
    1310                1315                1320

Asp Asn Pro Asp Tyr Trp His Ser Arg Leu Phe Pro Lys Ala Asn
    1325                1330                1335

Ala Gln Arg Thr
    1340

<210> SEQ ID NO 3
<211> LENGTH: 643
<212> TYPE: PRT
<213> ORGANISM: Artificial
<220> FEATURE:
<223> OTHER INFORMATION: Description of artificial sequence;
      extracellular region of erbB3

<400> SEQUENCE: 3

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
                20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
        50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
```

```
            100                 105                 110
Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
            130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
            195                 200                 205

Ile Cys Ala Pro Gln Cys Asn Gly His Cys Phe Gly Pro Asn Pro Asn
            210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
            275                 280                 285

Ser Cys Pro His Asn Phe Val Val Asp Gln Thr Ser Cys Val Arg Ala
            290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
            370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
            450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
            515                 520                 525
```

```
Cys Val Thr His Cys Asn Phe Leu Asn Gly Glu Pro Arg Glu Phe Ala
        530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
                580                 585                 590

Val Leu Gly Ala Lys Gly Pro Ile Tyr Lys Tyr Pro Asp Val Gln Asn
                595                 600                 605

Glu Cys Arg Pro Cys His Glu Asn Cys Thr Gln Gly Cys Lys Gly Pro
            610                 615                 620

Glu Leu Gln Asp Cys Leu Gly Gln Thr Leu Val Leu Ile Gly Lys Thr
625                 630                 635                 640

His Leu Thr
```

```
<210> SEQ ID NO 4
<211> LENGTH: 4020
<212> TYPE: DNA
<213> ORGANISM: Mus musculus
<220> FEATURE:
<221> NAME/KEY: CDS
<222> LOCATION: (1)..(4020)

<400> SEQUENCE: 4
```

| | | | | | | | | | | | | | | | | |
|---|---|---|---|---|---|---|---|---|---|---|---|---|---|---|---|---|
| atg | agt | gcg | att | ggg | act | ctg | cag | gtg | ctg | ggt | ttc | ctt | ctc | agc | ctg | 48 |
| Met | Ser | Ala | Ile | Gly | Thr | Leu | Gln | Val | Leu | Gly | Phe | Leu | Leu | Ser | Leu | |
| 1 | | | | 5 | | | | | 10 | | | | | 15 | | |
| gcc | cgg | ggt | tcc | gag | atg | ggc | aac | tct | cag | gca | gta | tgt | cct | ggg | act | 96 |
| Ala | Arg | Gly | Ser | Glu | Met | Gly | Asn | Ser | Gln | Ala | Val | Cys | Pro | Gly | Thr | |
| | | | 20 | | | | | 25 | | | | | 30 | | | |
| cta | aac | ggg | ctg | agt | gtg | acc | ggc | gat | gct | gac | aac | cag | tac | cag | aca | 144 |
| Leu | Asn | Gly | Leu | Ser | Val | Thr | Gly | Asp | Ala | Asp | Asn | Gln | Tyr | Gln | Thr | |
| | | 35 | | | | | 40 | | | | | 45 | | | | |
| ctg | tac | aaa | ctc | tat | gag | aag | tgt | gag | gtg | gtc | atg | ggt | aac | ctg | gag | 192 |
| Leu | Tyr | Lys | Leu | Tyr | Glu | Lys | Cys | Glu | Val | Val | Met | Gly | Asn | Leu | Glu | |
| 50 | | | | | 55 | | | | | 60 | | | | | | |
| att | gtg | ctt | acg | gga | cac | aat | gct | gat | ctt | tcc | ttc | ctg | caa | tgg | atc | 240 |
| Ile | Val | Leu | Thr | Gly | His | Asn | Ala | Asp | Leu | Ser | Phe | Leu | Gln | Trp | Ile | |
| 65 | | | | | 70 | | | | | 75 | | | | | 80 | |
| cga | gaa | gtg | aca | ggc | tat | gta | ctg | gtg | gcc | atg | aat | gaa | ttc | tct | gta | 288 |
| Arg | Glu | Val | Thr | Gly | Tyr | Val | Leu | Val | Ala | Met | Asn | Glu | Phe | Ser | Val | |
| | | | | 85 | | | | | 90 | | | | | 95 | | |
| ctg | ccc | tta | cct | aac | ctc | cga | gtg | gtc | cgg | gga | acc | cag | gtc | tac | gat | 336 |
| Leu | Pro | Leu | Pro | Asn | Leu | Arg | Val | Val | Arg | Gly | Thr | Gln | Val | Tyr | Asp | |
| | | | | 100 | | | | | 105 | | | | | 110 | | |
| ggg | aag | ttt | gcc | atc | ttt | gtc | atg | ttg | aac | tac | aat | acc | aac | tcc | agc | 384 |
| Gly | Lys | Phe | Ala | Ile | Phe | Val | Met | Leu | Asn | Tyr | Asn | Thr | Asn | Ser | Ser | |
| | | | 115 | | | | | 120 | | | | | 125 | | | |
| cat | gct | ctg | cgc | cag | ctc | cgg | ttc | act | cag | ctt | act | gag | att | ctg | tta | 432 |
| His | Ala | Leu | Arg | Gln | Leu | Arg | Phe | Thr | Gln | Leu | Thr | Glu | Ile | Leu | Leu | |
| | | | 130 | | | | | 135 | | | | | 140 | | | |
| ggg | ggc | gtt | tac | att | gag | aag | aat | gac | aaa | ctt | tgc | cac | atg | gat | aca | 480 |
| Gly | Gly | Val | Tyr | Ile | Glu | Lys | Asn | Asp | Lys | Leu | Cys | His | Met | Asp | Thr | |
| 145 | | | | | 150 | | | | | 155 | | | | | 160 | |
| att | gac | tgg | agg | gac | atc | gtg | agg | gtt | cca | gac | gct | gag | ata | gtg | gtg | 528 |
| Ile | Asp | Trp | Arg | Asp | Ile | Val | Arg | Val | Pro | Asp | Ala | Glu | Ile | Val | Val | |
| | | | | 165 | | | | | 170 | | | | | 175 | | |

```
aag aac aac ggg ggg aac tgt cca ccc tgt cac gaa gtc tgc aag ggg      576
Lys Asn Asn Gly Gly Asn Cys Pro Pro Cys His Glu Val Cys Lys Gly
            180                 185                 190 cga tgc tgg ggg cct gga cca gaa gac tgc cag ata ttg acc aag acc      624
Arg Cys Trp Gly Pro Gly Pro Glu Asp Cys Gln Ile Leu Thr Lys Thr
        195                 200                 205 atc tgt gcc cct cag tgt aac ggt cgc tgc ttc ggg ccc aat cct aac      672
Ile Cys Ala Pro Gln Cys Asn Gly Arg Cys Phe Gly Pro Asn Pro Asn
    210                 215                 220 cag tgc tgc cac gat gaa tgt gca ggt ggc tgc tct gga ccc cag gac      720
Gln Cys Cys His Asp Glu Cys Ala Gly Gly Cys Ser Gly Pro Gln Asp
225                 230                 235                 240 aca gat tgc ttc gcc tgc cga cac ttc aat gac agt ggt gcc tgt gtg      768
Thr Asp Cys Phe Ala Cys Arg His Phe Asn Asp Ser Gly Ala Cys Val
                245                 250                 255 ccc agg tgt cca gcg ccc ctt gtg tac aac aag cta acg ttc cag ctt      816
Pro Arg Cys Pro Ala Pro Leu Val Tyr Asn Lys Leu Thr Phe Gln Leu
            260                 265                 270 gag ccc aac ccc cat atc aag tat cag tac gga gga gtc tgt gtt gcc      864
Glu Pro Asn Pro His Ile Lys Tyr Gln Tyr Gly Gly Val Cys Val Ala
        275                 280                 285 agt tgt ccc cat aac ttt gtg gtg gat cag aca ttt tgt gtc agg gct      912
Ser Cys Pro His Asn Phe Val Val Asp Gln Thr Phe Cys Val Arg Ala
    290                 295                 300 tgt cct gct gac aag atg gaa gta gat aag aat gga ctc aag atg tgt      960
Cys Pro Ala Asp Lys Met Glu Val Asp Lys Asn Gly Leu Lys Met Cys
305                 310                 315                 320 gag cct tgc aga ggg ctg tgc cca aaa gcc tgt gag ggg acg ggc tct     1008
Glu Pro Cys Arg Gly Leu Cys Pro Lys Ala Cys Glu Gly Thr Gly Ser
                325                 330                 335 gga agc cgc tac cag acc gtg gac tct agc aat atc gat ggg ttc gtg     1056
Gly Ser Arg Tyr Gln Thr Val Asp Ser Ser Asn Ile Asp Gly Phe Val
            340                 345                 350 aac tgt acc aag atc ctg ggc aac ctg gac ttc ctc atc act ggc ctc     1104
Asn Cys Thr Lys Ile Leu Gly Asn Leu Asp Phe Leu Ile Thr Gly Leu
        355                 360                 365 aat ggt gac ccc tgg cac aag atc cct gca ctg gac ccg gaa aag ctc     1152
Asn Gly Asp Pro Trp His Lys Ile Pro Ala Leu Asp Pro Glu Lys Leu
    370                 375                 380 aat gtt ttc agg aca gtc cgg gag att aca ggc tac cta aac atc cag     1200
Asn Val Phe Arg Thr Val Arg Glu Ile Thr Gly Tyr Leu Asn Ile Gln
385                 390                 395                 400 tcc tgg ccc cct cac atg cac aac ttc agt gtt ttt tcc aac ctg acg     1248
Ser Trp Pro Pro His Met His Asn Phe Ser Val Phe Ser Asn Leu Thr
                405                 410                 415 acc atc ggg ggc aga agc ctc tac aat cgg ggc ttc tcc ttg ttg atc     1296
Thr Ile Gly Gly Arg Ser Leu Tyr Asn Arg Gly Phe Ser Leu Leu Ile
            420                 425                 430 atg aag aac ttg aat gtc acg tct ctg ggc ttc cgg tcc ctg aag gaa     1344
Met Lys Asn Leu Asn Val Thr Ser Leu Gly Phe Arg Ser Leu Lys Glu
        435                 440                 445 att agt gct ggg cgt gtc tac ata agt gcc aat cag caa ctt tgt tac     1392
Ile Ser Ala Gly Arg Val Tyr Ile Ser Ala Asn Gln Gln Leu Cys Tyr
    450                 455                 460 cac cac tct ctg aac tgg acc aga ctt ctg cgg ggg ccc gca gag gag     1440
His His Ser Leu Asn Trp Thr Arg Leu Leu Arg Gly Pro Ala Glu Glu
465                 470                 475                 480 aga ctt gac atc aag tac aac cgg cct ctg gga gaa tgc gtg gca gag     1488
Arg Leu Asp Ile Lys Tyr Asn Arg Pro Leu Gly Glu Cys Val Ala Glu
                485                 490                 495
```

| | | |
|---|---|---|
| ggc aaa gtg tgt gat cca ctg tgc tcc tct ggg gga tgc tgg ggc cca<br>Gly Lys Val Cys Asp Pro Leu Cys Ser Ser Gly Gly Cys Trp Gly Pro<br>500 505 510 | | 1536 |
| ggc cct ggt cag tgc ttg tct tgt cga aac tac agc cgg gaa ggt gtc<br>Gly Pro Gly Gln Cys Leu Ser Cys Arg Asn Tyr Ser Arg Glu Gly Val<br>515 520 525 | | 1584 |
| tgt gtg act cac tgc aac gtt ctg caa ggg gaa ccc cga gag ttt gtt<br>Cys Val Thr His Cys Asn Val Leu Gln Gly Glu Pro Arg Glu Phe Val<br>530 535 540 | | 1632 |
| cat gag gct cat tgc ttc tcc tgc cat cca gaa tgc cag ccc atg gag<br>His Glu Ala His Cys Phe Ser Cys His Pro Glu Cys Gln Pro Met Glu<br>545 550 555 560 | | 1680 |
| ggc acc agc acg tgc aat ggc tcg ggc tcc gac gct tgt gct cga tgc<br>Gly Thr Ser Thr Cys Asn Gly Ser Gly Ser Asp Ala Cys Ala Arg Cys<br>565 570 575 | | 1728 |
| gcc cat ttt cgt gat ggg ccc cac tgt gtg aac agc tgc ccc cat gga<br>Ala His Phe Arg Asp Gly Pro His Cys Val Asn Ser Cys Pro His Gly<br>580 585 590 | | 1776 |
| atc cta ggt gcc aaa ggt cca atc tac aaa tat cca gat gct cag aat<br>Ile Leu Gly Ala Lys Gly Pro Ile Tyr Lys Tyr Pro Asp Ala Gln Asn<br>595 600 605 | | 1824 |
| gag tgc cgg ccc tgc cac gag aac tgc acc caa ggg tgt aag gga cca<br>Glu Cys Arg Pro Cys His Glu Asn Cys Thr Gln Gly Cys Lys Gly Pro<br>610 615 620 | | 1872 |
| gaa cta caa gac tgt tta ggc caa gca gag gta tta atg agc aaa cca<br>Glu Leu Gln Asp Cys Leu Gly Gln Ala Glu Val Leu Met Ser Lys Pro<br>625 630 635 640 | | 1920 |
| cac ctg gtc ata gcg gtg aca gta gga ctg act gtg atc ttc ctg att<br>His Leu Val Ile Ala Val Thr Val Gly Leu Thr Val Ile Phe Leu Ile<br>645 650 655 | | 1968 |
| ctg gga ggc tct ttt ctc tat tgg cgt gga cgc agg att cag aat aaa<br>Leu Gly Gly Ser Phe Leu Tyr Trp Arg Gly Arg Arg Ile Gln Asn Lys<br>660 665 670 | | 2016 |
| agg gct atg aga cgc tac ttg gag cgg ggt gag agc atc gag cct ctg<br>Arg Ala Met Arg Arg Tyr Leu Glu Arg Gly Glu Ser Ile Glu Pro Leu<br>675 680 685 | | 2064 |
| gac cca agc gag aag gca aac aaa gtc ttg gct aga atc ttc aaa gag<br>Asp Pro Ser Glu Lys Ala Asn Lys Val Leu Ala Arg Ile Phe Lys Glu<br>690 695 700 | | 2112 |
| aca gag ctg agg aaa ctt aag gtg ctt ggc tct ggt gtc ttt gga act<br>Thr Glu Leu Arg Lys Leu Lys Val Leu Gly Ser Gly Val Phe Gly Thr<br>705 710 715 720 | | 2160 |
| gta cac aag ggg att tgg att ccc gag ggt gaa tcc atc aag att cca<br>Val His Lys Gly Ile Trp Ile Pro Glu Gly Glu Ser Ile Lys Ile Pro<br>725 730 735 | | 2208 |
| gtc tgc att aaa gtc atc gag gac aag agt ggg cgg cag agt ttt cag<br>Val Cys Ile Lys Val Ile Glu Asp Lys Ser Gly Arg Gln Ser Phe Gln<br>740 745 750 | | 2256 |
| gct gtg act gat cac atg ctg gcc gtc ggc agc ctg gac cat gcc cac<br>Ala Val Thr Asp His Met Leu Ala Val Gly Ser Leu Asp His Ala His<br>755 760 765 | | 2304 |
| att gta cgg ctg ctg gga ctg tgc cca ggg tca tct ctg cag ctt gtc<br>Ile Val Arg Leu Leu Gly Leu Cys Pro Gly Ser Ser Leu Gln Leu Val<br>770 775 780 | | 2352 |
| act cag tac ttg cct ctg ggc tct ctc ctt gat cat gta aga cag cac<br>Thr Gln Tyr Leu Pro Leu Gly Ser Leu Leu Asp His Val Arg Gln His<br>785 790 795 800 | | 2400 |
| cgt gag aca ctg gga cca cag ctg ctc ctc aac tgg gga gta caa att<br>Arg Glu Thr Leu Gly Pro Gln Leu Leu Leu Asn Trp Gly Val Gln Ile<br> | | 2448 |

|     |     |
| --- | --- |
| 805 810 815 | |
| gcc aag ggt atg tat tac ctc gag gaa cac agc atg gtg cat agg gac<br>Ala Lys Gly Met Tyr Tyr Leu Glu Glu His Ser Met Val His Arg Asp<br>820              825              830 | 2496 |
| ctt gcg ctc cgg aat gtg atg ctt aag tca ccg agt caa gtc cag gtg<br>Leu Ala Leu Arg Asn Val Met Leu Lys Ser Pro Ser Gln Val Gln Val<br>835              840              845 | 2544 |
| gca gat ttt ggt gtg gct gac ttg ctg ccg cca gat gac aag cag tta<br>Ala Asp Phe Gly Val Ala Asp Leu Leu Pro Pro Asp Asp Lys Gln Leu<br>850              855              860 | 2592 |
| cta cac agt gag gcc aag act cca att aaa tgg atg gcc ctt gag agt<br>Leu His Ser Glu Ala Lys Thr Pro Ile Lys Trp Met Ala Leu Glu Ser<br>865              870              875              880 | 2640 |
| atc cac ttt ggg aaa tac aca cac cag agt gat gtc tgg agt tac ggt<br>Ile His Phe Gly Lys Tyr Thr His Gln Ser Asp Val Trp Ser Tyr Gly<br>                  885              890              895 | 2688 |
| gta acc gtt tgg gag ttg atg acc ttc ggg gca gag ccc tac gca ggg<br>Val Thr Val Trp Glu Leu Met Thr Phe Gly Ala Glu Pro Tyr Ala Gly<br>900              905              910 | 2736 |
| cta cga ctg gct gaa ata cca gac ctg ctg gag aag gga gag cgg tta<br>Leu Arg Leu Ala Glu Ile Pro Asp Leu Leu Glu Lys Gly Glu Arg Leu<br>915              920              925 | 2784 |
| gca cag ccc cag atc tgc acc att gac gtc tac atg gtc atg gtc aag<br>Ala Gln Pro Gln Ile Cys Thr Ile Asp Val Tyr Met Val Met Val Lys<br>930              935              940 | 2832 |
| tgt tgg atg att gac gag aat att cgc cca acc ttt aaa gaa ctg gcc<br>Cys Trp Met Ile Asp Glu Asn Ile Arg Pro Thr Phe Lys Glu Leu Ala<br>945              950              955              960 | 2880 |
| aat gag ttt acc agg atg gcc cgg gac cca cca agg tat ctg gtc atc<br>Asn Glu Phe Thr Arg Met Ala Arg Asp Pro Pro Arg Tyr Leu Val Ile<br>                  965              970              975 | 2928 |
| aag aga gcg agt ggg cct gga ata cct cct gca gca gag cca tct gct<br>Lys Arg Ala Ser Gly Pro Gly Ile Pro Pro Ala Ala Glu Pro Ser Ala<br>980              985              990 | 2976 |
| ctg agc acc aaa gag ttg cag gat gca gag ctg gag cca gac ctg gac<br>Leu Ser Thr Lys Glu Leu Gln Asp Ala Glu Leu Glu Pro Asp Leu Asp<br>995              1000             1005 | 3024 |
| ctc gac cta gac gtg gag gta gaa gag gag ggc ctg gcg acc aca<br>Leu Asp Leu Asp Val Glu Val Glu Glu Glu Gly Leu Ala Thr Thr<br>1010             1015             1020 | 3069 |
| ctg ggt tct gcc ctc agc ttg cct aca gga acg ctt acc cgg cca<br>Leu Gly Ser Ala Leu Ser Leu Pro Thr Gly Thr Leu Thr Arg Pro<br>1025             1030             1035 | 3114 |
| cgt ggg agc cag agt ctt tta agt cct tcg tct gga tac atg ccc<br>Arg Gly Ser Gln Ser Leu Leu Ser Pro Ser Ser Gly Tyr Met Pro<br>1040             1045             1050 | 3159 |
| atg aac cag agc aac ctt ggg gag gct tgt ctg gat tct gcg gtt<br>Met Asn Gln Ser Asn Leu Gly Glu Ala Cys Leu Asp Ser Ala Val<br>1055             1060             1065 | 3204 |
| ttg ggg ggt cgc gaa cag ttc tcc cgt ccc atc tct ctg cac ccg<br>Leu Gly Gly Arg Glu Gln Phe Ser Arg Pro Ile Ser Leu His Pro<br>1070             1075             1080 | 3249 |
| atc cca cgg ggg cgt caa acg tca gag tca tca gag ggc cat gtg<br>Ile Pro Arg Gly Arg Gln Thr Ser Glu Ser Ser Glu Gly His Val<br>1085             1090             1095 | 3294 |
| acg ggc tct gag gct gaa ctc caa gag aga gta tca atg tgt agg<br>Thr Gly Ser Glu Ala Glu Leu Gln Glu Arg Val Ser Met Cys Arg<br>1100             1105             1110 | 3339 |
| agc cgg agc cgg agc cgg agc cca cgg cca cgt ggg gac agt gcc | 3384 |

| | | | | | | | | | | |
|---|---|---|---|---|---|---|---|---|---|---|
| Ser | Arg | Ser | Arg | Ser | Arg | Ser | Pro | Arg | Pro | Arg | Gly | Asp | Ser | Ala |
| 1115 | | | | 1120 | | | | | 1125 | |

```
tac cat tcg cag cga cac agc ctg ctt act ccc gtc acc ccg ctc    3429
Tyr His Ser Gln Arg His Ser Leu Leu Thr Pro Val Thr Pro Leu
    1130                1135                1140 tcc cca cca ggg tta gag gaa gag gat ggc aat ggt tat gtc atg    3474
Ser Pro Pro Gly Leu Glu Glu Glu Asp Gly Asn Gly Tyr Val Met
1145                1150                1155 cca gat acg cac ctc aga ggt aca tcc tct tcc cgg gaa ggc acc    3519
Pro Asp Thr His Leu Arg Gly Thr Ser Ser Ser Arg Glu Gly Thr
    1160                1165                1170 ctt tcg tca gta ggt ctc agt tct gtg ctg ggt acc gaa gag gaa    3564
Leu Ser Ser Val Gly Leu Ser Ser Val Leu Gly Thr Glu Glu Glu
    1175                1180                1185 gat gaa gat gag gag tat gaa tac atg aac cgg aag agg agg ggt    3609
Asp Glu Asp Glu Glu Tyr Glu Tyr Met Asn Arg Lys Arg Arg Gly
    1190                1195                1200 agc ccg gct cgg ccc ccc aga cct ggt tcc ctg gaa gag ctg ggc    3654
Ser Pro Ala Arg Pro Pro Arg Pro Gly Ser Leu Glu Glu Leu Gly
    1205                1210                1215 tat gag tac atg gat gtg ggt tca gac ctc agt gct tct ctg ggc    3699
Tyr Glu Tyr Met Asp Val Gly Ser Asp Leu Ser Ala Ser Leu Gly
    1220                1225                1230 agt acg cag agt tgc cca ctc cat ccc atg gcc atc gtg ccc tct    3744
Ser Thr Gln Ser Cys Pro Leu His Pro Met Ala Ile Val Pro Ser
    1235                1240                1245 gct ggc acg act cca gat gag gac tat gaa tac atg aac cgc agg    3789
Ala Gly Thr Thr Pro Asp Glu Asp Tyr Glu Tyr Met Asn Arg Arg
    1250                1255                1260 cgt ggt gcg ggc ggt tcc gga ggg gat tat gca gct atg ggg gcc    3834
Arg Gly Ala Gly Gly Ser Gly Gly Asp Tyr Ala Ala Met Gly Ala
    1265                1270                1275 tgc cca gca gct gaa caa ggg tat gag gaa atg cga gct ttc cag    3879
Cys Pro Ala Ala Glu Gln Gly Tyr Glu Glu Met Arg Ala Phe Gln
    1280                1285                1290 ggg cct gga cat caa gcc ccc cat gtt cgt tat gcc cgc ctc aaa    3924
Gly Pro Gly His Gln Ala Pro His Val Arg Tyr Ala Arg Leu Lys
    1295                1300                1305 act ctg cgt agt tta gaa gcc act gac tcc gcc ttt gac aac ccc    3969
Thr Leu Arg Ser Leu Glu Ala Thr Asp Ser Ala Phe Asp Asn Pro
    1310                1315                1320 gat tac tgg cat agc agg ctt ttc cct aag gct aac gcc cag aga    4014
Asp Tyr Trp His Ser Arg Leu Phe Pro Lys Ala Asn Ala Gln Arg
    1325                1330                1335 att tga                                                         4020
Ile

<210> SEQ ID NO 5
<211> LENGTH: 1339
<212> TYPE: PRT
<213> ORGANISM: Mus musculus

<400> SEQUENCE: 5

Met Ser Ala Ile Gly Thr Leu Gln Val Leu Gly Phe Leu Leu Ser Leu
1               5                   10                  15

Ala Arg Gly Ser Glu Met Gly Asn Ser Gln Ala Val Cys Pro Gly Thr
            20                  25                  30

Leu Asn Gly Leu Ser Val Thr Gly Asp Ala Asp Asn Gln Tyr Gln Thr
        35                  40                  45
```

```
Leu Tyr Lys Leu Tyr Glu Lys Cys Glu Val Val Met Gly Asn Leu Glu
 50                  55                  60

Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Val
                 85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Phe Thr Gln Leu Thr Glu Ile Leu Leu
130                 135                 140

Gly Gly Val Tyr Ile Glu Lys Asn Asp Lys Leu Cys His Met Asp Thr
145                 150                 155                 160

Ile Asp Trp Arg Asp Ile Val Arg Val Pro Asp Ala Glu Ile Val Val
                165                 170                 175

Lys Asn Asn Gly Gly Asn Cys Pro Pro Cys His Glu Val Cys Lys Gly
            180                 185                 190

Arg Cys Trp Gly Pro Gly Pro Glu Asp Cys Gln Ile Leu Thr Lys Thr
        195                 200                 205

Ile Cys Ala Pro Gln Cys Asn Gly Arg Cys Phe Gly Pro Asn Pro Asn
210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Ala Pro Leu Val Tyr Asn Lys Leu Thr Phe Gln Leu
            260                 265                 270

Glu Pro Asn Pro His Ile Lys Tyr Gln Tyr Gly Gly Val Cys Val Ala
        275                 280                 285

Ser Cys Pro His Asn Phe Val Val Asp Gln Thr Phe Cys Val Arg Ala
290                 295                 300

Cys Pro Ala Asp Lys Met Glu Val Asp Lys Asn Gly Leu Lys Met Cys
305                 310                 315                 320

Glu Pro Cys Arg Gly Leu Cys Pro Lys Ala Cys Glu Gly Thr Gly Ser
                325                 330                 335

Gly Ser Arg Tyr Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
        355                 360                 365

Asn Gly Asp Pro Trp His Lys Ile Pro Ala Leu Asp Pro Glu Lys Leu
370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
        435                 440                 445

Ile Ser Ala Gly Arg Val Tyr Ile Ser Ala Asn Gln Gln Leu Cys Tyr
450                 455                 460

His His Ser Leu Asn Trp Thr Arg Leu Leu Arg Gly Pro Ala Glu Glu
```

```
            465                 470                 475                 480
Arg Leu Asp Ile Lys Tyr Asn Arg Pro Leu Gly Glu Cys Val Ala Glu
                    485                 490                 495
Gly Lys Val Cys Asp Pro Leu Cys Ser Ser Gly Gly Cys Trp Gly Pro
                500                 505                 510
Gly Pro Gly Gln Cys Leu Ser Cys Arg Asn Tyr Ser Arg Glu Gly Val
            515                 520                 525
Cys Val Thr His Cys Asn Val Leu Gln Gly Glu Pro Arg Glu Phe Val
        530                 535                 540
His Glu Ala His Cys Phe Ser Cys His Pro Glu Cys Gln Pro Met Glu
545                 550                 555                 560
Gly Thr Ser Thr Cys Asn Gly Ser Gly Ser Asp Ala Cys Ala Arg Cys
                565                 570                 575
Ala His Phe Arg Asp Gly Pro His Cys Val Asn Ser Cys Pro His Gly
                580                 585                 590
Ile Leu Gly Ala Lys Gly Pro Ile Tyr Lys Tyr Pro Asp Ala Gln Asn
            595                 600                 605
Glu Cys Arg Pro Cys His Glu Asn Cys Thr Gln Gly Cys Lys Gly Pro
        610                 615                 620
Glu Leu Gln Asp Cys Leu Gly Gln Ala Glu Val Leu Met Ser Lys Pro
625                 630                 635                 640
His Leu Val Ile Ala Val Thr Val Gly Leu Thr Val Ile Phe Leu Ile
                645                 650                 655
Leu Gly Gly Ser Phe Leu Tyr Trp Arg Gly Arg Ile Gln Asn Lys
                660                 665                 670
Arg Ala Met Arg Arg Tyr Leu Glu Arg Gly Glu Ser Ile Glu Pro Leu
            675                 680                 685
Asp Pro Ser Glu Lys Ala Asn Lys Val Leu Ala Arg Ile Phe Lys Glu
        690                 695                 700
Thr Glu Leu Arg Lys Leu Lys Val Leu Gly Ser Gly Val Phe Gly Thr
705                 710                 715                 720
Val His Lys Gly Ile Trp Ile Pro Glu Gly Glu Ser Ile Lys Ile Pro
                725                 730                 735
Val Cys Ile Lys Val Ile Glu Asp Lys Ser Gly Arg Gln Ser Phe Gln
            740                 745                 750
Ala Val Thr Asp His Met Leu Ala Val Gly Ser Leu Asp His Ala His
        755                 760                 765
Ile Val Arg Leu Leu Gly Leu Cys Pro Gly Ser Ser Leu Gln Leu Val
    770                 775                 780
Thr Gln Tyr Leu Pro Leu Gly Ser Leu Leu Asp His Val Arg Gln His
785                 790                 795                 800
Arg Glu Thr Leu Gly Pro Gln Leu Leu Leu Asn Trp Gly Val Gln Ile
                805                 810                 815
Ala Lys Gly Met Tyr Tyr Leu Glu Glu His Ser Met Val His Arg Asp
            820                 825                 830
Leu Ala Leu Arg Asn Val Met Leu Lys Ser Pro Ser Gln Val Gln Val
        835                 840                 845
Ala Asp Phe Gly Val Ala Asp Leu Leu Pro Pro Asp Lys Gln Leu
        850                 855                 860
Leu His Ser Glu Ala Lys Thr Pro Ile Lys Trp Met Ala Leu Glu Ser
865                 870                 875                 880
Ile His Phe Gly Lys Tyr Thr His Gln Ser Asp Val Trp Ser Tyr Gly
                885                 890                 895
```

-continued

Val Thr Val Trp Glu Leu Met Thr Phe Gly Ala Glu Pro Tyr Ala Gly
            900                 905                 910

Leu Arg Leu Ala Glu Ile Pro Asp Leu Leu Glu Lys Gly Glu Arg Leu
        915                 920                 925

Ala Gln Pro Gln Ile Cys Thr Ile Asp Val Tyr Met Val Met Val Lys
    930                 935                 940

Cys Trp Met Ile Asp Glu Asn Ile Arg Pro Thr Phe Lys Glu Leu Ala
945                 950                 955                 960

Asn Glu Phe Thr Arg Met Ala Arg Asp Pro Pro Arg Tyr Leu Val Ile
                965                 970                 975

Lys Arg Ala Ser Gly Pro Gly Ile Pro Pro Ala Ala Glu Pro Ser Ala
            980                 985                 990

Leu Ser Thr Lys Glu Leu Gln Asp Ala Glu Leu Glu Pro Asp Leu Asp
        995                 1000                1005

Leu Asp Leu Asp Val Glu Val Glu Glu Glu Gly Leu Ala Thr Thr
    1010                1015                1020

Leu Gly Ser Ala Leu Ser Leu Pro Thr Gly Thr Leu Thr Arg Pro
    1025                1030                1035

Arg Gly Ser Gln Ser Leu Leu Ser Pro Ser Ser Gly Tyr Met Pro
    1040                1045                1050

Met Asn Gln Ser Asn Leu Gly Glu Ala Cys Leu Asp Ser Ala Val
    1055                1060                1065

Leu Gly Gly Arg Glu Gln Phe Ser Arg Pro Ile Ser Leu His Pro
    1070                1075                1080

Ile Pro Arg Gly Arg Gln Thr Ser Glu Ser Ser Glu Gly His Val
    1085                1090                1095

Thr Gly Ser Glu Ala Glu Leu Gln Glu Arg Val Ser Met Cys Arg
    1100                1105                1110

Ser Arg Ser Arg Ser Arg Ser Pro Arg Pro Arg Gly Asp Ser Ala
    1115                1120                1125

Tyr His Ser Gln Arg His Ser Leu Leu Thr Pro Val Thr Pro Leu
    1130                1135                1140

Ser Pro Pro Gly Leu Glu Glu Glu Asp Gly Asn Gly Tyr Val Met
    1145                1150                1155

Pro Asp Thr His Leu Arg Gly Thr Ser Ser Ser Arg Glu Gly Thr
    1160                1165                1170

Leu Ser Ser Val Gly Leu Ser Ser Val Leu Gly Thr Glu Glu Glu
    1175                1180                1185

Asp Glu Asp Glu Glu Tyr Glu Tyr Met Asn Arg Lys Arg Arg Gly
    1190                1195                1200

Ser Pro Ala Arg Pro Pro Arg Pro Gly Ser Leu Glu Glu Leu Gly
    1205                1210                1215

Tyr Glu Tyr Met Asp Val Gly Ser Asp Leu Ser Ala Ser Leu Gly
    1220                1225                1230

Ser Thr Gln Ser Cys Pro Leu His Pro Met Ala Ile Val Pro Ser
    1235                1240                1245

Ala Gly Thr Thr Pro Asp Glu Asp Tyr Glu Tyr Met Asn Arg Arg
    1250                1255                1260

Arg Gly Ala Gly Gly Ser Gly Gly Asp Tyr Ala Ala Met Gly Ala
    1265                1270                1275

Cys Pro Ala Ala Glu Gln Gly Tyr Glu Glu Met Arg Ala Phe Gln
    1280                1285                1290

Gly Pro Gly His Gln Ala Pro His Val Arg Tyr Ala Arg Leu Lys
    1295            1300                1305

Thr Leu Arg Ser Leu Glu Ala Thr Asp Ser Ala Phe Asp Asn Pro
    1310            1315                1320

Asp Tyr Trp His Ser Arg Leu Phe Pro Lys Ala Asn Ala Gln Arg
    1325            1330                1335

Ile

<210> SEQ ID NO 6
<211> LENGTH: 643
<212> TYPE: PRT
<213> ORGANISM: Artificial
<220> FEATURE:
<223> OTHER INFORMATION: Description of artificial sequence;
      extracellular region of mouse erbB3

<400> SEQUENCE: 6

Met Ser Ala Ile Gly Thr Leu Gln Val Leu Gly Phe Leu Leu Ser Leu
1               5                   10                  15

Ala Arg Gly Ser Glu Met Gly Asn Ser Gln Ala Val Cys Pro Gly Thr
                20                  25                  30

Leu Asn Gly Leu Ser Val Thr Gly Asp Ala Asp Asn Gln Tyr Gln Thr
            35                  40                  45

Leu Tyr Lys Leu Tyr Glu Lys Cys Glu Val Val Met Gly Asn Leu Glu
        50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Val
                85                  90                  95

Leu Pro Leu Pro Asn Leu Arg Val Arg Gly Thr Gln Val Tyr Asp
                100                 105                 110

Gly Lys Phe Ala Ile Phe Val Met Leu Asn Tyr Asn Thr Asn Ser Ser
            115                 120                 125

His Ala Leu Arg Gln Leu Arg Phe Thr Gln Leu Thr Glu Ile Leu Leu
        130                 135                 140

Gly Gly Val Tyr Ile Glu Lys Asn Asp Lys Leu Cys His Met Asp Thr
145                 150                 155                 160

Ile Asp Trp Arg Asp Ile Val Arg Val Pro Asp Ala Glu Ile Val Val
                165                 170                 175

Lys Asn Asn Gly Gly Asn Cys Pro Cys His Glu Val Cys Lys Gly
                180                 185                 190

Arg Cys Trp Gly Pro Gly Pro Glu Asp Cys Gln Ile Leu Thr Lys Thr
            195                 200                 205

Ile Cys Ala Pro Gln Cys Asn Gly Arg Cys Phe Gly Pro Asn Pro Asn
        210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Ala Pro Leu Val Tyr Asn Lys Leu Thr Phe Gln Leu
                260                 265                 270

Glu Pro Asn Pro His Ile Lys Tyr Gln Tyr Gly Gly Val Cys Val Ala
            275                 280                 285

Ser Cys Pro His Asn Phe Val Val Asp Gln Thr Phe Cys Val Arg Ala
        290                 295                 300

```
Cys Pro Ala Asp Lys Met Glu Val Asp Lys Asn Gly Leu Lys Met Cys
305                 310                 315                 320

Glu Pro Cys Arg Gly Leu Cys Pro Lys Ala Cys Glu Gly Thr Gly Ser
            325                 330                 335

Gly Ser Arg Tyr Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
            370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
                420                 425                 430

Met Lys Asn Leu Asn Val Thr Ser Leu Gly Phe Arg Ser Leu Lys Glu
            435                 440                 445

Ile Ser Ala Gly Arg Val Tyr Ile Ser Ala Asn Gln Gln Leu Cys Tyr
450                 455                 460

His His Ser Leu Asn Trp Thr Arg Leu Leu Arg Gly Pro Ala Glu Glu
465                 470                 475                 480

Arg Leu Asp Ile Lys Tyr Asn Arg Pro Leu Gly Glu Cys Val Ala Glu
                485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Glu Gly Val
            515                 520                 525

Cys Val Thr His Cys Asn Val Leu Gln Gly Glu Pro Arg Glu Phe Val
530                 535                 540

His Glu Ala His Cys Phe Ser Cys His Pro Glu Cys Gln Pro Met Glu
545                 550                 555                 560

Gly Thr Ser Thr Cys Asn Gly Ser Gly Ser Asp Ala Cys Ala Arg Cys
                565                 570                 575

Ala His Phe Arg Asp Gly Pro His Cys Val Asn Ser Cys Pro His Gly
                580                 585                 590

Ile Leu Gly Ala Lys Gly Pro Ile Tyr Lys Tyr Pro Asp Ala Gln Asn
            595                 600                 605

Glu Cys Arg Pro Cys His Glu Asn Cys Thr Gln Gly Cys Lys Gly Pro
610                 615                 620

Glu Leu Gln Asp Cys Leu Gly Gln Ala Glu Val Leu Met Ser Lys Pro
625                 630                 635                 640

His Leu Val

<210> SEQ ID NO 7
<211> LENGTH: 33
<212> TYPE: DNA
<213> ORGANISM: Artificial
<220> FEATURE:
<223> OTHER INFORMATION: Descrption of artificial sequence; rherbB3
      primer1

<400> SEQUENCE: 7
gggggtacca tgagggcgaa cgacgctatg cag                                33
```

```
<210> SEQ ID NO 8
<211> LENGTH: 33
<212> TYPE: DNA
<213> ORGANISM: Artificial
<220> FEATURE:
<223> OTHER INFORMATION: Description of artificial sequence; rherbB3
      primer2

<400> SEQUENCE: 8
gctctagatg tcagatgggt tttgccgatc agc                                  33

<210> SEQ ID NO 9
<211> LENGTH: 32
<212> TYPE: DNA
<213> ORGANISM: Artificial
<220> FEATURE:
<223> OTHER INFORMATION: Description of artificial sequence; rherbB3-GST
      primer1

<400> SEQUENCE: 9
gaagatctat gagggcgaac gacgctctgc ag                                   32

<210> SEQ ID NO 10
<211> LENGTH: 34
<212> TYPE: DNA
<213> ORGANISM: Artificial
<220> FEATURE:
<223> OTHER INFORMATION: Description of artificial sequence; rherbB3-GST
      primer2

<400> SEQUENCE: 10
gggggtacct gtcagatggg ttttgccgat cagc                                 34

<210> SEQ ID NO 11
<211> LENGTH: 45
<212> TYPE: DNA
<213> ORGANISM: Artificial
<220> FEATURE:
<223> OTHER INFORMATION: Description of artificial sequence; mouse
      erbB3-GST primer1

<400> SEQUENCE: 11
gggagatctg ccaccatgag tgcgattggg actctgcagg tgctg                     45

<210> SEQ ID NO 12
<211> LENGTH: 39
<212> TYPE: DNA
<213> ORGANISM: Artificial
<220> FEATURE:
<223> OTHER INFORMATION: Description of artificial sequence; mouse
      erbB3-GST primer2

<400> SEQUENCE: 12
gggacgcgtg tgtggtttgc tcattaatac ctctgcttg                            39

<210> SEQ ID NO 13
<211> LENGTH: 49
<212> TYPE: DNA
<213> ORGANISM: Artificial
<220> FEATURE:
<223> OTHER INFORMATION: Description of artificial sequence; hD1/mD234
      primer1

<400> SEQUENCE: 13
gggagatctg ccgccaccat gagggcgaac gacgctctgc aggtgctgg                 49

<210> SEQ ID NO 14
```

```
<211> LENGTH: 40
<212> TYPE: DNA
<213> ORGANISM: Artificial
<220> FEATURE:
<223> OTHER INFORMATION: Description of artificial sequence; hD1/mD234
      primer2

<400> SEQUENCE: 14
cagggtggac agttccccccc attgtccttc accactatct                            40

<210> SEQ ID NO 15
<211> LENGTH: 40
<212> TYPE: DNA
<213> ORGANISM: Artificial
<220> FEATURE:
<223> OTHER INFORMATION: Description of artificial sequence; hD1/mD234
      primer3

<400> SEQUENCE: 15
agatagtggt gaaggacaat gggggggaact gtccaccctg                            40

<210> SEQ ID NO 16
<211> LENGTH: 39
<212> TYPE: DNA
<213> ORGANISM: Artificial
<220> FEATURE:
<223> OTHER INFORMATION: Description of artificial sequence; hD1/mD234
      primer4

<400> SEQUENCE: 16
gggacgcgtg tgtggtttgc tcattaatac ctctgcttg                              39

<210> SEQ ID NO 17
<211> LENGTH: 49
<212> TYPE: DNA
<213> ORGANISM: Artificial
<220> FEATURE:
<223> OTHER INFORMATION: Description of artificial sequence; hD1/mD234
      primer5

<400> SEQUENCE: 17
gggagatctg ccgccaccat gagggcgaac gacgctctgc aggtgctgg                   49

<210> SEQ ID NO 18
<211> LENGTH: 38
<212> TYPE: DNA
<213> ORGANISM: Artificial
<220> FEATURE:
<223> OTHER INFORMATION: Description of artificial sequence; hD1/mD234
      primer6

<400> SEQUENCE: 18
ggacgcgtgt gtggtttgct cattaatacc tctgcttg                               38

<210> SEQ ID NO 19
<211> LENGTH: 49
<212> TYPE: DNA
<213> ORGANISM: Artificial
<220> FEATURE:
<223> OTHER INFORMATION: Description of artificial sequence; hD12/mD34
      primer1

<400> SEQUENCE: 19
gggagatctg ccgccaccat gagggcgaac gacgctctgc aggtgctgg                   49

<210> SEQ ID NO 20
<211> LENGTH: 40
```

```
<212> TYPE: DNA
<213> ORGANISM: Artificial
<220> FEATURE:
<223> OTHER INFORMATION: Description of artificial sequence; hD12/mD34
      primer2

<400> SEQUENCE: 20
cccgtcccct cacaggcttt gggacatagt cccccacaag                               40

<210> SEQ ID NO 21
<211> LENGTH: 40
<212> TYPE: DNA
<213> ORGANISM: Artificial
<220> FEATURE:
<223> OTHER INFORMATION: Description of artificial sequence; hD12/mD34
      primer3

<400> SEQUENCE: 21
cttgtggggg actatgtccc aaagcctgtg aggggacggg                               40

<210> SEQ ID NO 22
<211> LENGTH: 39
<212> TYPE: DNA
<213> ORGANISM: Artificial
<220> FEATURE:
<223> OTHER INFORMATION: Description of artificial sequence; hD12/mD34
      primer4

<400> SEQUENCE: 22
gggacgcgtg tgtggtttgc tcattaatac ctctgcttg                                39

<210> SEQ ID NO 23
<211> LENGTH: 49
<212> TYPE: DNA
<213> ORGANISM: Artificial
<220> FEATURE:
<223> OTHER INFORMATION: Description of artificial sequence; hD12/mD34
      primer5

<400> SEQUENCE: 23
gggagatctg ccgccaccat gagggcgaac gacgctctgc aggtgctgg                     49

<210> SEQ ID NO 24
<211> LENGTH: 39
<212> TYPE: DNA
<213> ORGANISM: Artificial
<220> FEATURE:
<223> OTHER INFORMATION: Description of artificial sequence; hD12/mD34
      primer6

<400> SEQUENCE: 24
gggacgcgtg tgtggtttgc tcattaatac ctctgcttg                                39

<210> SEQ ID NO 25
<211> LENGTH: 49
<212> TYPE: DNA
<213> ORGANISM: Artificial
<220> FEATURE:
<223> OTHER INFORMATION: Description of artificial sequence; hD123/mD4
      primer1

<400> SEQUENCE: 25
gggagatctg ccgccaccat gagggcgaac gacgctctgc aggtgctgg                     49

<210> SEQ ID NO 26
<211> LENGTH: 41
<212> TYPE: DNA
```

<213> ORGANISM: Artificial
<220> FEATURE:
<223> OTHER INFORMATION: Description of artificial sequence; hD123/mD4
    primer2

<400> SEQUENCE: 26
acgcattctc ccagaggccg attatgcttg atgtctagtc g                          41

<210> SEQ ID NO 27
<211> LENGTH: 41
<212> TYPE: DNA
<213> ORGANISM: Artificial
<220> FEATURE:
<223> OTHER INFORMATION: Description of artificial sequence; hD123/mD4
    primer3

<400> SEQUENCE: 27
cgactagaca tcaagcataa tcggcctctg ggagaatgcg t                          41

<210> SEQ ID NO 28
<211> LENGTH: 39
<212> TYPE: DNA
<213> ORGANISM: Artificial
<220> FEATURE:
<223> OTHER INFORMATION: Description of artificial sequence; hD123/mD4
    primer4

<400> SEQUENCE: 28
gggacgcgtg tgtggtttgc tcattaatac ctctgcttg                             39

<210> SEQ ID NO 29
<211> LENGTH: 49
<212> TYPE: DNA
<213> ORGANISM: Artificial
<220> FEATURE:
<223> OTHER INFORMATION: Description of artificial sequence; hD123/mD4
    primer5

<400> SEQUENCE: 29
gggagatctg ccgccaccat gagggcgaac gacgctctgc aggtgctgg                  49

<210> SEQ ID NO 30
<211> LENGTH: 27
<212> TYPE: DNA
<213> ORGANISM: Artificial
<220> FEATURE:
<223> OTHER INFORMATION: Description of artificial sequence; hD123/mD4
    primer6

<400> SEQUENCE: 30
actagtcttg tcatcgtcgt ccttgta                                          27

<210> SEQ ID NO 31
<211> LENGTH: 30
<212> TYPE: DNA
<213> ORGANISM: Artificial
<220> FEATURE:
<223> OTHER INFORMATION: Description of artificial sequence: mkRvP1
    primer

<400> SEQUENCE: 31
ttgaagctct tgacaatggg tgaagttgat                                       30

<210> SEQ ID NO 32
<211> LENGTH: 30
<212> TYPE: DNA
<213> ORGANISM: Artificial

```
<220> FEATURE:
<223> OTHER INFORMATION: Description of artificial sequence: mkRvP2
      primer

<400> SEQUENCE: 32
gtaggtgctg tctttgctgt cctgatcagt                                      30

<210> SEQ ID NO 33
<211> LENGTH: 32
<212> TYPE: DNA
<213> ORGANISM: Artificial
<220> FEATURE:
<223> OTHER INFORMATION: Description of artificial sequence: mH-Rv1
      primer

<400> SEQUENCE: 33
attttgtcga cckyggtsyt gctggcyggg tg                                   32

<210> SEQ ID NO 34
<211> LENGTH: 34
<212> TYPE: DNA
<213> ORGANISM: Artificial
<220> FEATURE:
<223> OTHER INFORMATION: Description of artificial sequence: mH-Rv2
      primer

<400> SEQUENCE: 34
gcacacyrct ggacagggat ccatccagag ttcc                                 34

<210> SEQ ID NO 35
<211> LENGTH: 27
<212> TYPE: DNA
<213> ORGANISM: Artificial
<220> FEATURE:
<223> OTHER INFORMATION: Description of artificial sequence; SEQ4618
      primer

<400> SEQUENCE: 35
tctatataag cagagctggg tacgtcc                                         27

<210> SEQ ID NO 36
<211> LENGTH: 27
<212> TYPE: DNA
<213> ORGANISM: Artificial
<220> FEATURE:
<223> OTHER INFORMATION: Description of artificial sequence; SEQ1783
      primer

<400> SEQUENCE: 36
ggtacgtgaa ccgtcagatc gcctgga                                         27

<210> SEQ ID NO 37
<211> LENGTH: 41
<212> TYPE: DNA
<213> ORGANISM: Artificial
<220> FEATURE:
<223> OTHER INFORMATION: Description of artificial sequence;
      1153Hc-SalIU primer

<400> SEQUENCE: 37
acgcgtcgac ctcaccatgg aatggagcgg ggtccttatc t                         41

<210> SEQ ID NO 38
<211> LENGTH: 34
<212> TYPE: DNA
<213> ORGANISM: Artificial
<220> FEATURE:
```

```
<223> OTHER INFORMATION: Description of artificial sequence;
      1153Hc-NheIL primer

<400> SEQUENCE: 38
ctagctagct gaggagactg tgagagtggt gcct                               34

<210> SEQ ID NO 39
<211> LENGTH: 38
<212> TYPE: DNA
<213> ORGANISM: Artificial
<220> FEATURE:
<223> OTHER INFORMATION: Description of artificial sequence;
      1153Lc-BglII primer

<400> SEQUENCE: 39
gaagatctct caccatgagg gtccttgctg agctcctg                           38

<210> SEQ ID NO 40
<211> LENGTH: 41
<212> TYPE: DNA
<213> ORGANISM: Artificial
<220> FEATURE:
<223> OTHER INFORMATION: Description of artificial sequence;
      1153Lc-BsiWI primer

<400> SEQUENCE: 40
agagagagag cgtacgtctg atttccagct tggtgcctcc a                       41

<210> SEQ ID NO 41
<211> LENGTH: 41
<212> TYPE: DNA
<213> ORGANISM: Artificial
<220> FEATURE:
<223> OTHER INFORMATION: Description of artificial sequence;
      920104Hc-SalIU primer

<400> SEQUENCE: 41
acgcgtcgac ctcaccatga aagtgttgag tctgttgtac c                       41

<210> SEQ ID NO 42
<211> LENGTH: 35
<212> TYPE: DNA
<213> ORGANISM: Artificial
<220> FEATURE:
<223> OTHER INFORMATION: Description of artificial sequence;
      920104Hc-NheIL primer

<400> SEQUENCE: 42
ctagctagct gaggagacgg tgactgaggt tcctt                              35

<210> SEQ ID NO 43
<211> LENGTH: 44
<212> TYPE: DNA
<213> ORGANISM: Artificial
<220> FEATURE:
<223> OTHER INFORMATION: Description of artificial sequence;
      920104Lc-BglII primer

<400> SEQUENCE: 43
gaagatctct caccatggag acagacacac tcctgttatg ggta                    44

<210> SEQ ID NO 44
<211> LENGTH: 46
<212> TYPE: DNA
<213> ORGANISM: Artificial
<220> FEATURE:
<223> OTHER INFORMATION: Description of artificial sequence;
```

```
                920104Lc-BsiWI primer

<400> SEQUENCE: 44
agagagagag cgtacgtttc agctccagct tggtcccagc accgaa              46

<210> SEQ ID NO 45
<211> LENGTH: 44
<212> TYPE: DNA
<213> ORGANISM: Artificial
<220> FEATURE:
<223> OTHER INFORMATION: Description of artificial sequence;
      1126 Hc-SalIU primer

<400> SEQUENCE: 45
acgcgtcgac ctcaccatga acttcaggct cagcttgatt ttcc                44

<210> SEQ ID NO 46
<211> LENGTH: 37
<212> TYPE: DNA
<213> ORGANISM: Artificial
<220> FEATURE:
<223> OTHER INFORMATION: Description of artificial sequence;
      1126 Hc-NheIL primer

<400> SEQUENCE: 46
ctagctagct gcagagacag tgaccagagt cccttgg                        37

<210> SEQ ID NO 47
<211> LENGTH: 48
<212> TYPE: DNA
<213> ORGANISM: Artificial
<220> FEATURE:
<223> OTHER INFORMATION: Description of artificial sequence;
      1126Lc-PmeIU primer

<400> SEQUENCE: 47
agctttgttt aaacctcacc atgaagttgc ctgttaggct gttggtgc             48

<210> SEQ ID NO 48
<211> LENGTH: 42
<212> TYPE: DNA
<213> ORGANISM: Artificial
<220> FEATURE:
<223> OTHER INFORMATION: Description of artificial sequence;
      1126Lc-BsiWI primer

<400> SEQUENCE: 48
agagagagag cgtacgtttt atttccagct tggtcccccc tc                   42

<210> SEQ ID NO 49
<211> LENGTH: 43
<212> TYPE: DNA
<213> ORGANISM: Artificial
<220> FEATURE:
<223> OTHER INFORMATION: Description of artificial sequence;
      12511Hc-SalIU primer

<400> SEQUENCE: 49
acgcgtcgac ctcaccatgg gatggagctg gatctttctt ttc                  43

<210> SEQ ID NO 50
<211> LENGTH: 36
<212> TYPE: DNA
<213> ORGANISM: Artificial
<220> FEATURE:
<223> OTHER INFORMATION: Description of artificial sequence;
      12511Hc-NheIL primer
```

```
<400> SEQUENCE: 50
ctagctagct gcagagacag tgaccagagt cccttg                              36

<210> SEQ ID NO 51
<211> LENGTH: 44
<212> TYPE: DNA
<213> ORGANISM: Artificial
<220> FEATURE:
<223> OTHER INFORMATION: Description of artificial sequence;
      12511Lc-BglII primer

<400> SEQUENCE: 51
gaagatctct caccatggag acagacacac tcctgctatg ggtg                     44

<210> SEQ ID NO 52
<211> LENGTH: 42
<212> TYPE: DNA
<213> ORGANISM: Artificial
<220> FEATURE:
<223> OTHER INFORMATION: Description of artificial sequence;
      12511Lc-BsiWI primer

<400> SEQUENCE: 52
agagagagag cgtacgtttg atttccagct tggtgcctcc ac                       42

<210> SEQ ID NO 53
<211> LENGTH: 414
<212> TYPE: DNA
<213> ORGANISM: Mus musculus
<220> FEATURE:
<221> NAME/KEY: CDS
<222> LOCATION: (1)..(414)

<400> SEQUENCE: 53 atg gaa tgg agc ggg gtc ctt atc ttt ctc ctg tca gta act gca ggt      48
Met Glu Trp Ser Gly Val Leu Ile Phe Leu Leu Ser Val Thr Ala Gly
1               5                   10                  15 gtc cac tcc cag gtc cag ctg cag cag tct gga gct gag ctg gtg agg      96
Val His Ser Gln Val Gln Leu Gln Gln Ser Gly Ala Glu Leu Val Arg
            20                  25                  30 cct ggg act tca gtg aag atg tcc tgc aag gct gct gga tac acc ttt     144
Pro Gly Thr Ser Val Lys Met Ser Cys Lys Ala Ala Gly Tyr Thr Phe
        35                  40                  45 act aac tac tgg ata gtt tgg gta aag cag agg cct gga cat ggc ctt     192
Thr Asn Tyr Trp Ile Val Trp Val Lys Gln Arg Pro Gly His Gly Leu
    50                  55                  60 gag tgg att gga gat att tac ccg gga agt ggt cat act aac tat aat     240
Glu Trp Ile Gly Asp Ile Tyr Pro Gly Ser Gly His Thr Asn Tyr Asn
65                  70                  75                  80 gag aag ttc aag ggc aag gcc aca ctg act gca gac aca tcc tcc agc     288
Glu Lys Phe Lys Gly Lys Ala Thr Leu Thr Ala Asp Thr Ser Ser Ser
                85                  90                  95 aca gcc aac atg cag ctc agc agc ctg aca tct gag gac tct gcc att     336
Thr Ala Asn Met Gln Leu Ser Ser Leu Thr Ser Glu Asp Ser Ala Ile
            100                 105                 110 tat tac tgt gta aga cct atc aac tac gat ggt agc tac gac tac tgg     384
Tyr Tyr Cys Val Arg Pro Ile Asn Tyr Asp Gly Ser Tyr Asp Tyr Trp
        115                 120                 125 ggc caa ggc acc act ctc aca gtc tcc tca                             414
Gly Gln Gly Thr Thr Leu Thr Val Ser Ser
    130                 135
```

```
<210> SEQ ID NO 54
<211> LENGTH: 138
<212> TYPE: PRT
<213> ORGANISM: Mus musculus

<400> SEQUENCE: 54

Met Glu Trp Ser Gly Val Leu Ile Phe Leu Leu Ser Val Thr Ala Gly
1               5                   10                  15

Val His Ser Gln Val Gln Leu Gln Gln Ser Gly Ala Glu Leu Val Arg
            20                  25                  30

Pro Gly Thr Ser Val Lys Met Ser Cys Lys Ala Ala Gly Tyr Thr Phe
        35                  40                  45

Thr Asn Tyr Trp Ile Val Trp Val Lys Gln Arg Pro Gly His Gly Leu
    50                  55                  60

Glu Trp Ile Gly Asp Ile Tyr Pro Gly Ser Gly His Thr Asn Tyr Asn
65                  70                  75                  80

Glu Lys Phe Lys Gly Lys Ala Thr Leu Thr Ala Asp Thr Ser Ser Ser
                85                  90                  95

Thr Ala Asn Met Gln Leu Ser Ser Leu Thr Ser Glu Asp Ser Ala Ile
            100                 105                 110

Tyr Tyr Cys Val Arg Pro Ile Asn Tyr Asp Gly Ser Tyr Asp Tyr Trp
        115                 120                 125

Gly Gln Gly Thr Thr Leu Thr Val Ser Ser
    130                 135

<210> SEQ ID NO 55
<211> LENGTH: 381
<212> TYPE: DNA
<213> ORGANISM: Mus musculus
<220> FEATURE:
<221> NAME/KEY: CDS
<222> LOCATION: (1)..(381)

<400> SEQUENCE: 55 atg agg gtc ctt gct gag ctc ctg ggg ctg ctg ctg ttc tgc ttt tta      48
Met Arg Val Leu Ala Glu Leu Leu Gly Leu Leu Leu Phe Cys Phe Leu
1               5                   10                  15 ggt gtg aga tgt gac atc cag atg aac cag tct cca tcc agt ctg tct      96
Gly Val Arg Cys Asp Ile Gln Met Asn Gln Ser Pro Ser Ser Leu Ser
            20                  25                  30 gca tcc ctt gga gac aca att acc atc act tgc cat gcc agt cag aac     144
Ala Ser Leu Gly Asp Thr Ile Thr Ile Thr Cys His Ala Ser Gln Asn
        35                  40                  45 att aat gtt tgg tta agc tgg tac cag cag aaa cca gga aat att cct     192
Ile Asn Val Trp Leu Ser Trp Tyr Gln Gln Lys Pro Gly Asn Ile Pro
    50                  55                  60 aaa cta ttg atc tat aag gct tcc aac ttg cac aca ggc gtc cca tca     240
Lys Leu Leu Ile Tyr Lys Ala Ser Asn Leu His Thr Gly Val Pro Ser
65                  70                  75                  80 agg ttt agt ggc agt gga tct gga aca ggt ttc aca tta acc atc agc     288
Arg Phe Ser Gly Ser Gly Ser Gly Thr Gly Phe Thr Leu Thr Ile Ser
                85                  90                  95 agc ctg cag cct gaa gac att gcc act tac tac tgt caa cag ggt caa     336
Ser Leu Gln Pro Glu Asp Ile Ala Thr Tyr Tyr Cys Gln Gln Gly Gln
            100                 105                 110 agt tat cct cgg acg ttc ggt gga ggc acc aag ctg gaa atc aga         381
Ser Tyr Pro Arg Thr Phe Gly Gly Gly Thr Lys Leu Glu Ile Arg
        115                 120                 125

<210> SEQ ID NO 56
```

```
<211> LENGTH: 127
<212> TYPE: PRT
<213> ORGANISM: Mus musculus

<400> SEQUENCE: 56

Met Arg Val Leu Ala Glu Leu Leu Gly Leu Leu Leu Phe Cys Phe Leu
1               5                   10                  15

Gly Val Arg Cys Asp Ile Gln Met Asn Gln Ser Pro Ser Ser Leu Ser
            20                  25                  30

Ala Ser Leu Gly Asp Thr Ile Thr Ile Thr Cys His Ala Ser Gln Asn
        35                  40                  45

Ile Asn Val Trp Leu Ser Trp Tyr Gln Gln Lys Pro Gly Asn Ile Pro
50                  55                  60

Lys Leu Leu Ile Tyr Lys Ala Ser Asn Leu His Thr Gly Val Pro Ser
65                  70                  75                  80

Arg Phe Ser Gly Ser Gly Ser Gly Thr Gly Phe Thr Leu Thr Ile Ser
                85                  90                  95

Ser Leu Gln Pro Glu Asp Ile Ala Thr Tyr Tyr Cys Gln Gln Gly Gln
            100                 105                 110

Ser Tyr Pro Arg Thr Phe Gly Gly Gly Thr Lys Leu Glu Ile Arg
        115                 120                 125

<210> SEQ ID NO 57
<211> LENGTH: 119
<212> TYPE: PRT
<213> ORGANISM: Mus musculus

<400> SEQUENCE: 57

Gln Val Gln Leu Gln Gln Ser Gly Ala Glu Leu Val Arg Pro Gly Thr
1               5                   10                  15

Ser Val Lys Met Ser Cys Lys Ala Ala Gly Tyr Thr Phe Thr Asn Tyr
            20                  25                  30

Trp Ile Val Trp Val Lys Gln Arg Pro Gly His Gly Leu Glu Trp Ile
        35                  40                  45

Gly Asp Ile Tyr Pro Gly Ser Gly His Thr Asn Tyr Asn Glu Lys Phe
50                  55                  60

Lys Gly Lys Ala Thr Leu Thr Ala Asp Thr Ser Ser Ser Thr Ala Asn
65                  70                  75                  80

Met Gln Leu Ser Ser Leu Thr Ser Glu Asp Ser Ala Ile Tyr Tyr Cys
                85                  90                  95

Val Arg Pro Ile Asn Tyr Asp Gly Ser Tyr Asp Tyr Trp Gly Gln Gly
            100                 105                 110

Thr Thr Leu Thr Val Ser Ser
        115

<210> SEQ ID NO 58
<211> LENGTH: 107
<212> TYPE: PRT
<213> ORGANISM: Mus musculus

<400> SEQUENCE: 58

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45
```

-continued

```
Tyr Lys Ala Ser Asn Leu His Thr Gly Val Pro Ser Arg Phe Ser Gly
         50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Gly Gln Ser Tyr Pro Arg
                 85                  90                  95

Thr Phe Gly Gly Gly Thr Lys Leu Glu Ile Arg
                100                 105
```

<210> SEQ ID NO 59
<211> LENGTH: 5
<212> TYPE: PRT
<213> ORGANISM: Mus musculus

<400> SEQUENCE: 59

```
Asn Tyr Trp Ile Val
1               5
```

<210> SEQ ID NO 60
<211> LENGTH: 17
<212> TYPE: PRT
<213> ORGANISM: Mus musculus

<400> SEQUENCE: 60

```
Asp Ile Tyr Pro Gly Ser Gly His Thr Asn Tyr Asn Glu Lys Phe Lys
1               5                   10                  15

Gly
```

<210> SEQ ID NO 61
<211> LENGTH: 10
<212> TYPE: PRT
<213> ORGANISM: Mus musculus

<400> SEQUENCE: 61

```
Pro Ile Asn Tyr Asp Gly Ser Tyr Asp Tyr
1               5                   10
```

<210> SEQ ID NO 62
<211> LENGTH: 11
<212> TYPE: PRT
<213> ORGANISM: Mus musculus

<400> SEQUENCE: 62

```
His Ala Ser Gln Asn Ile Asn Val Trp Leu Ser
1               5                   10
```

<210> SEQ ID NO 63
<211> LENGTH: 7
<212> TYPE: PRT
<213> ORGANISM: Mus musculus

<400> SEQUENCE: 63

```
Lys Ala Ser Asn Leu His Thr
1               5
```

<210> SEQ ID NO 64
<211> LENGTH: 9
<212> TYPE: PRT
<213> ORGANISM: Mus musculus

<400> SEQUENCE: 64

```
Gln Gln Gly Gln Ser Tyr Pro Arg Thr
1               5
```

<210> SEQ ID NO 65
<211> LENGTH: 420
<212> TYPE: DNA
<213> ORGANISM: Mus musculus
<220> FEATURE:
<221> NAME/KEY: CDS
<222> LOCATION: (1)..(420)

<400> SEQUENCE: 65

| | | | | | | | | | | | | | | | | |
|---|---|---|---|---|---|---|---|---|---|---|---|---|---|---|---|---|
| atg | aaa | gtg | ttg | agt | ctg | ttg | tac | ctg | ttg | aca | gcc | att | cct | ggt | atc | 48 |
| Met | Lys | Val | Leu | Ser | Leu | Leu | Tyr | Leu | Leu | Thr | Ala | Ile | Pro | Gly | Ile | |
| 1 | | | | 5 | | | | | 10 | | | | | 15 | | |
| ctg | tct | gat | gta | cag | ctt | cag | gag | tca | gga | cct | ggc | ctc | gtg | aaa | cct | 96 |
| Leu | Ser | Asp | Val | Gln | Leu | Gln | Glu | Ser | Gly | Pro | Gly | Leu | Val | Lys | Pro | |
| | | | 20 | | | | | 25 | | | | | 30 | | | |
| tct | cag | tct | ctg | tct | ctc | acc | tgc | tct | gtc | act | ggc | tac | tcc | ttc | acc | 144 |
| Ser | Gln | Ser | Leu | Ser | Leu | Thr | Cys | Ser | Val | Thr | Gly | Tyr | Ser | Phe | Thr | |
| | | 35 | | | | | 40 | | | | | 45 | | | | |
| aat | ggt | tat | tac | tgg | aac | tgg | atc | cgg | cag | ttt | cca | gga | aac | aaa | ctg | 192 |
| Asn | Gly | Tyr | Tyr | Trp | Asn | Trp | Ile | Arg | Gln | Phe | Pro | Gly | Asn | Lys | Leu | |
| | 50 | | | | | 55 | | | | | 60 | | | | | |
| gaa | tgg | atg | ggc | tac | ata | agc | tac | gat | ggt | aac | aat | agc | tac | aac | cca | 240 |
| Glu | Trp | Met | Gly | Tyr | Ile | Ser | Tyr | Asp | Gly | Asn | Asn | Ser | Tyr | Asn | Pro | |
| 65 | | | | | 70 | | | | | 75 | | | | | 80 | |
| tct | ctc | aaa | aat | cga | atc | tcc | atc | act | cgt | gac | aca | tct | aag | aac | cag | 288 |
| Ser | Leu | Lys | Asn | Arg | Ile | Ser | Ile | Thr | Arg | Asp | Thr | Ser | Lys | Asn | Gln | |
| | | | | 85 | | | | | 90 | | | | | 95 | | |
| ttt | ttc | ctg | aag | ttg | aat | tct | gtg | act | act | gag | gac | aca | gcc | aca | tat | 336 |
| Phe | Phe | Leu | Lys | Leu | Asn | Ser | Val | Thr | Thr | Glu | Asp | Thr | Ala | Thr | Tyr | |
| | | | 100 | | | | | 105 | | | | | 110 | | | |
| tac | tgt | gca | agc | cat | ggt | tac | tac | gag | gag | gat | tac | tat | gct | atg | gac | 384 |
| Tyr | Cys | Ala | Ser | His | Gly | Tyr | Tyr | Glu | Glu | Asp | Tyr | Tyr | Ala | Met | Asp | |
| | | | 115 | | | | | 120 | | | | | 125 | | | |
| tac | tgg | ggt | caa | gga | acc | tca | gtc | acc | gtc | tcc | tca | | | | | 420 |
| Tyr | Trp | Gly | Gln | Gly | Thr | Ser | Val | Thr | Val | Ser | Ser | | | | | |
| | 130 | | | | | 135 | | | | | 140 | | | | | |

<210> SEQ ID NO 66
<211> LENGTH: 140
<212> TYPE: PRT
<213> ORGANISM: Mus musculus

<400> SEQUENCE: 66

Met Lys Val Leu Ser Leu Leu Tyr Leu Leu Thr Ala Ile Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Ser Val Thr Gly Tyr Ser Phe Thr
        35                  40                  45

Asn Gly Tyr Tyr Trp Asn Trp Ile Arg Gln Phe Pro Gly Asn Lys Leu
    50                  55                  60

Glu Trp Met Gly Tyr Ile Ser Tyr Asp Gly Asn Asn Ser Tyr Asn Pro
65                  70                  75                  80

Ser Leu Lys Asn Arg Ile Ser Ile Thr Arg Asp Thr Ser Lys Asn Gln
                85                  90                  95

Phe Phe Leu Lys Leu Asn Ser Val Thr Thr Glu Asp Thr Ala Thr Tyr
            100                 105                 110

Tyr Cys Ala Ser His Gly Tyr Tyr Glu Glu Asp Tyr Tyr Ala Met Asp
        115                 120                 125

```
Tyr Trp Gly Gln Gly Thr Ser Val Thr Val Ser Ser
        130                 135                 140

<210> SEQ ID NO 67
<211> LENGTH: 393
<212> TYPE: DNA
<213> ORGANISM: Mus musculus
<220> FEATURE:
<221> NAME/KEY: CDS
<222> LOCATION: (1)..(393)

<400> SEQUENCE: 67 atg gag aca gac aca ctc ctg tta tgg gta ctg ctg ctc tgg gtt cca      48
Met Glu Thr Asp Thr Leu Leu Leu Trp Val Leu Leu Leu Trp Val Pro
1               5                   10                  15 ggt tcc act ggt gac att gtg ctg aca cag tct cct gct tcc tta gct      96
Gly Ser Thr Gly Asp Ile Val Leu Thr Gln Ser Pro Ala Ser Leu Ala
            20                  25                  30 gta tct ctg ggg cag agg gcc acc atc tca tgc agg gcc agc aaa agt     144
Val Ser Leu Gly Gln Arg Ala Thr Ile Ser Cys Arg Ala Ser Lys Ser
        35                  40                  45 gtc agt aca tct ggc tat agt tat atg cac tgg tac caa cag aaa cca     192
Val Ser Thr Ser Gly Tyr Ser Tyr Met His Trp Tyr Gln Gln Lys Pro
    50                  55                  60 gga cag cca ccc aaa ctc ctc atc tat ctt gca tcc aac cta gaa tct     240
Gly Gln Pro Pro Lys Leu Leu Ile Tyr Leu Ala Ser Asn Leu Glu Ser
65                  70                  75                  80 ggg gtc cct gcc agg ttc agt ggc agt ggg tct ggg aca gac ttc acc     288
Gly Val Pro Ala Arg Phe Ser Gly Ser Gly Ser Gly Thr Asp Phe Thr
                85                  90                  95 ctc aac atc cat cct gtg gag gag gag gat gct gca acc tat tac tgt     336
Leu Asn Ile His Pro Val Glu Glu Glu Asp Ala Ala Thr Tyr Tyr Cys
            100                 105                 110 cag cac agt agg gag ctt ccg ctc acg ttc ggt gct ggg acc aag ctg     384
Gln His Ser Arg Glu Leu Pro Leu Thr Phe Gly Ala Gly Thr Lys Leu
        115                 120                 125 gag ctg aaa                                                          393
Glu Leu Lys
    130

<210> SEQ ID NO 68
<211> LENGTH: 131
<212> TYPE: PRT
<213> ORGANISM: Mus musculus

<400> SEQUENCE: 68

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Thr Ser Gly Tyr Ser Tyr Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110
```

-continued

Gln His Ser Arg Glu Leu Pro Leu Thr Phe Gly Ala Gly Thr Lys Leu
            115                 120                 125
Glu Leu Lys
        130

<210> SEQ ID NO 69
<211> LENGTH: 121
<212> TYPE: PRT
<213> ORGANISM: Mus musculus

<400> SEQUENCE: 69

Val Gln Leu Gln Glu Ser Gly Pro Gly Leu Val Lys Pro Ser Gln Ser
1               5                   10                  15
Leu Ser Leu Thr Cys Ser Val Thr Gly Tyr Ser Phe Thr Asn Gly Tyr
            20                  25                  30
Tyr Trp Asn Trp Ile Arg Gln Phe Pro Gly Asn Lys Leu Glu Trp Met
        35                  40                  45
Gly Tyr Ile Ser Tyr Asp Gly Asn Asn Ser Tyr Asn Pro Ser Leu Lys
    50                  55                  60
Asn Arg Ile Ser Ile Thr Arg Asp Thr Ser Lys Asn Gln Phe Phe Leu
65                  70                  75                  80
Lys Leu Asn Ser Val Thr Thr Glu Asp Thr Ala Thr Tyr Tyr Cys Ala
                85                  90                  95
Ser His Gly Tyr Tyr Glu Glu Asp Tyr Tyr Ala Met Asp Tyr Trp Gly
            100                 105                 110
Gln Gly Thr Ser Val Thr Val Ser Ser
            115                 120

<210> SEQ ID NO 70
<211> LENGTH: 111
<212> TYPE: PRT
<213> ORGANISM: Mus musculus

<400> SEQUENCE: 70

Asp Ile Val Leu Thr Gln Ser Pro Ala Ser Leu Ala Val Ser Leu Gly
1               5                   10                  15
Gln Arg Ala Thr Ile Ser Cys Arg Ala Ser Lys Ser Val Ser Thr Ser
            20                  25                  30
Gly Tyr Ser Tyr Met His Trp Tyr Gln Gln Lys Pro Gly Gln Pro Pro
        35                  40                  45
Lys Leu Leu Ile Tyr Leu Ala Ser Asn Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln His Ser Arg
                85                  90                  95
Glu Leu Pro Leu Thr Phe Gly Ala Gly Thr Lys Leu Glu Leu Lys
            100                 105                 110

<210> SEQ ID NO 71
<211> LENGTH: 6
<212> TYPE: PRT
<213> ORGANISM: Mus musculus

<400> SEQUENCE: 71

Asn Gly Tyr Tyr Trp Asn
1               5

```
<210> SEQ ID NO 72
<211> LENGTH: 16
<212> TYPE: PRT
<213> ORGANISM: Mus musculus

<400> SEQUENCE: 72

Tyr Ile Ser Tyr Asp Gly Asn Asn Ser Tyr Asn Pro Ser Leu Lys Asn
1               5                   10                  15

<210> SEQ ID NO 73
<211> LENGTH: 13
<212> TYPE: PRT
<213> ORGANISM: Mus musculus

<400> SEQUENCE: 73

His Gly Tyr Tyr Glu Glu Asp Tyr Tyr Ala Met Asp Tyr
1               5                   10

<210> SEQ ID NO 74
<211> LENGTH: 15
<212> TYPE: PRT
<213> ORGANISM: Mus musculus

<400> SEQUENCE: 74

Arg Ala Ser Lys Ser Val Ser Thr Ser Gly Tyr Ser Tyr Met His
1               5                   10                  15

<210> SEQ ID NO 75
<211> LENGTH: 7
<212> TYPE: PRT
<213> ORGANISM: Mus musculus

<400> SEQUENCE: 75

Leu Ala Ser Asn Leu Glu Ser
1               5

<210> SEQ ID NO 76
<211> LENGTH: 9
<212> TYPE: PRT
<213> ORGANISM: Mus musculus

<400> SEQUENCE: 76

Gln His Ser Arg Glu Leu Pro Leu Thr
1               5

<210> SEQ ID NO 77
<211> LENGTH: 414
<212> TYPE: DNA
<213> ORGANISM: Mus musculus
<220> FEATURE:
<221> NAME/KEY: CDS
<222> LOCATION: (1)..(414)

<400> SEQUENCE: 77 atg aac ttc agg ctc agc ttg att ttc ctt gcc ctt att tta aaa ggt      48
Met Asn Phe Arg Leu Ser Leu Ile Phe Leu Ala Leu Ile Leu Lys Gly
1               5                   10                  15 gtc cag tgt gaa gtg aag ctg gtg gag tct ggg gga ggc tta gtg aag      96
Val Gln Cys Glu Val Lys Leu Val Glu Ser Gly Gly Gly Leu Val Lys
                20                  25                  30 cct gga ggg tcc ctg aaa ctc tcc tgt gca gcc tct gga ttc act ttc     144
Pro Gly Gly Ser Leu Lys Leu Ser Cys Ala Ala Ser Gly Phe Thr Phe
            35                  40                  45 agt agc ttt gcc atg tct tgg gtt cgc cag act cca gag aag agg ctg     192
```

```
Ser Ser Phe Ala Met Ser Trp Val Arg Gln Thr Pro Glu Lys Arg Leu
    50                  55                  60 gag tgg gtc gca gtc att aat agt aat ggt ggt atc acc gac tat cca      240
Glu Trp Val Ala Val Ile Asn Ser Asn Gly Gly Ile Thr Asp Tyr Pro
65                  70                  75                  80 gac act gtg aag gac cga ttc acc atc tcc aga gac aat gcc aag aac      288
Asp Thr Val Lys Asp Arg Phe Thr Ile Ser Arg Asp Asn Ala Lys Asn
                85                  90                  95 acc ctg tac ctg caa atg agc agt ctg agg tct gag gac aca gcc ttg      336
Thr Leu Tyr Leu Gln Met Ser Ser Leu Arg Ser Glu Asp Thr Ala Leu
            100                 105                 110 tat ttc tgt gca aga cgg ggt ggt aac tac gcc tgg ttt gct tac tgg      384
Tyr Phe Cys Ala Arg Arg Gly Gly Asn Tyr Ala Trp Phe Ala Tyr Trp
        115                 120                 125 ggc caa ggg act ctg gtc act gtc tct gca                              414
Gly Gln Gly Thr Leu Val Thr Val Ser Ala
130                 135

<210> SEQ ID NO 78
<211> LENGTH: 138
<212> TYPE: PRT
<213> ORGANISM: Mus musculus

<400> SEQUENCE: 78

Met Asn Phe Arg Leu Ser Leu Ile Phe Leu Ala Leu Ile Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Phe Ala Met Ser Trp Val Arg Gln Thr Pro Glu Lys Arg Leu
    50                  55                  60

Glu Trp Val Ala Val Ile Asn Ser Asn Gly Gly Ile Thr Asp Tyr Pro
65                  70                  75                  80

Asp Thr Val Lys Asp Arg Phe Thr Ile Ser Arg Asp Asn Ala Lys Asn
                85                  90                  95

Thr Leu Tyr Leu Gln Met Ser Ser Leu Arg Ser Glu Asp Thr Ala Leu
            100                 105                 110

Tyr Phe Cys Ala Arg Arg Gly Gly Asn Tyr Ala Trp Phe Ala Tyr Trp
        115                 120                 125

Gly Gln Gly Thr Leu Val Thr Val Ser Ala
    130                 135

<210> SEQ ID NO 79
<211> LENGTH: 393
<212> TYPE: DNA
<213> ORGANISM: Mus musculus
<220> FEATURE:
<221> NAME/KEY: CDS
<222> LOCATION: (1)..(393)

<400> SEQUENCE: 79 atg aag ttg cct gtt agg ctg ttg gtg ctg atg ttc tgg att cct gct       48
Met Lys Leu Pro Val Arg Leu Leu Val Leu Met Phe Trp Ile Pro Ala
1               5                   10                  15 tcc agc agt gat gtt ttg atg acc caa act cca ctc tcc ctg cct gtc       96
Ser Ser Ser Asp Val Leu Met Thr Gln Thr Pro Leu Ser Leu Pro Val
            20                  25                  30 agt ctt gga gat cag gcc tcc atc tct tgc aga tcc agt cag agc att      144
Ser Leu Gly Asp Gln Ala Ser Ile Ser Cys Arg Ser Ser Gln Ser Ile
```

```
                35                  40                  45
gta cat agt aat gga aac acc tat tta gaa tgg tac ctg cag aaa cca     192
Val His Ser Asn Gly Asn Thr Tyr Leu Glu Trp Tyr Leu Gln Lys Pro
     50                  55                  60 ggc cag tct cca aag ctc ctg atc tac aaa gtt tcc aac cga ttt tct     240
Gly Gln Ser Pro Lys Leu Leu Ile Tyr Lys Val Ser Asn Arg Phe Ser
 65                  70                  75                  80 ggg gtc cca gac agg ttc agt ggc agt gga tca ggg aca gat ttc aca     288
Gly Val Pro Asp Arg Phe Ser Gly Ser Gly Ser Gly Thr Asp Phe Thr
                 85                  90                  95 ctc aag atc agc aga gtg gag gct gag gat ctg gga gtt tat tac tgc     336
Leu Lys Ile Ser Arg Val Glu Ala Glu Asp Leu Gly Val Tyr Tyr Cys
            100                 105                 110 ttt caa ggt tca cat gtt ccg tac acg ttc gga ggg ggg acc aag ctg     384
Phe Gln Gly Ser His Val Pro Tyr Thr Phe Gly Gly Gly Thr Lys Leu
        115                 120                 125 gaa ata aaa                                                         393
Glu Ile Lys
    130
```

<210> SEQ ID NO 80
<211> LENGTH: 131
<212> TYPE: PRT
<213> ORGANISM: Mus musculus

<400> SEQUENCE: 80

Met Lys Leu Pro Val Arg Leu Leu Val Leu Met Phe Trp Ile Pro Ala
 1               5                   10                  15

Ser Ser Ser Asp Val Leu Met Thr Gln Thr Pro Leu Ser Leu Pro Val
                20                  25                  30

Ser Leu Gly Asp Gln Ala Ser Ile Ser Cys Arg Ser Ser Gln Ser Ile
            35                  40                  45

Val His Ser Asn Gly Asn Thr Tyr Leu Glu Trp Tyr Leu Gln Lys Pro
     50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Tyr Cys
            100                 105                 110

Phe Gln Gly Ser His Val Pro Tyr Thr Phe Gly Gly Gly Thr Lys Leu
        115                 120                 125

Glu Ile Lys
    130

<210> SEQ ID NO 81
<211> LENGTH: 119
<212> TYPE: PRT
<213> ORGANISM: Mus musculus

<400> SEQUENCE: 81

Glu Val Lys Leu Val Glu Ser Gly Gly Gly Leu Val Lys Pro Gly Gly
 1               5                   10                  15

Ser Leu Lys Leu Ser Cys Ala Ala Ser Gly Phe Thr Phe Ser Ser Phe
                20                  25                  30

Ala Met Ser Trp Val Arg Gln Thr Pro Glu Lys Arg Leu Glu Trp Val
            35                  40                  45

Ala Val Ile Asn Ser Asn Gly Gly Ile Thr Asp Tyr Pro Asp Thr Val

```
                   50                  55                  60
Lys Asp Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Leu Tyr Phe Cys
                 85                  90                  95

Ala Arg Arg Gly Gly Asn Tyr Ala Trp Phe Ala Tyr Trp Gly Gln Gly
            100                 105                 110

Thr Leu Val Thr Val Ser Ala
        115

<210> SEQ ID NO 82
<211> LENGTH: 112
<212> TYPE: PRT
<213> ORGANISM: Mus musculus

<400> SEQUENCE: 82

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Tyr Thr Phe Gly Gly Gly Thr Lys Leu Glu Ile Lys
            100                 105                 110

<210> SEQ ID NO 83
<211> LENGTH: 5
<212> TYPE: PRT
<213> ORGANISM: Mus musculus

<400> SEQUENCE: 83

Ser Phe Ala Met Ser
 1               5

<210> SEQ ID NO 84
<211> LENGTH: 17
<212> TYPE: PRT
<213> ORGANISM: Mus musculus

<400> SEQUENCE: 84

Val Ile Asn Ser Asn Gly Gly Ile Thr Asp Tyr Pro Asp Thr Val Lys
 1               5                  10                  15

Asp

<210> SEQ ID NO 85
<211> LENGTH: 10
<212> TYPE: PRT
<213> ORGANISM: Mus musculus

<400> SEQUENCE: 85

Arg Gly Gly Asn Tyr Ala Trp Phe Ala Tyr
 1               5                  10
```

```
<210> SEQ ID NO 86
<211> LENGTH: 16
<212> TYPE: PRT
<213> ORGANISM: Mus musculus

<400> SEQUENCE: 86

Arg Ser Ser Gln Ser Ile Val His Ser Asn Gly Asn Thr Tyr Leu Glu
1               5                   10                  15

<210> SEQ ID NO 87
<211> LENGTH: 7
<212> TYPE: PRT
<213> ORGANISM: Mus musculus

<400> SEQUENCE: 87

Lys Val Ser Asn Arg Phe Ser
1               5

<210> SEQ ID NO 88
<211> LENGTH: 9
<212> TYPE: PRT
<213> ORGANISM: Mus musculus

<400> SEQUENCE: 88

Phe Gln Gly Ser His Val Pro Tyr Thr
1               5

<210> SEQ ID NO 89
<211> LENGTH: 414
<212> TYPE: DNA
<213> ORGANISM: Mus musculus
<220> FEATURE:
<221> NAME/KEY: CDS
<222> LOCATION: (1)..(414)

<400> SEQUENCE: 89 atg gga tgg agc tgg atc ttt ctt ttc ctc ctg tca gga act gca ggt      48
Met Gly Trp Ser Trp Ile Phe Leu Phe Leu Leu Ser Gly Thr Ala Gly
1               5                   10                  15 gtc cat tgc cag atc cag ctg caa cag tct gga cct gag ctg gtg aac      96
Val His Cys Gln Ile Gln Leu Gln Gln Ser Gly Pro Glu Leu Val Asn
                20                  25                  30 cct ggg gct tca gtg aag ata tcc tgc aag cct tct ggc tac acc ttc     144
Pro Gly Ala Ser Val Lys Ile Ser Cys Lys Pro Ser Gly Tyr Thr Phe
            35                  40                  45 act gac tac tat ata aac tgg gtg aag cag agg cct gga cag gga ctt     192
Thr Asp Tyr Tyr Ile Asn Trp Val Lys Gln Arg Pro Gly Gln Gly Leu
        50                  55                  60 gag tgg att gga tgg att cac cct gga ggc gga tat act aag tac aat     240
Glu Trp Ile Gly Trp Ile His Pro Gly Gly Gly Tyr Thr Lys Tyr Asn
65                  70                  75                  80 gaa aaa ttc agg ggc aag gcc aca gtg act gta gac aca tcc gcc aac     288
Glu Lys Phe Arg Gly Lys Ala Thr Val Thr Val Asp Thr Ser Ala Asn
                85                  90                  95 aca gtt tac atg cag ctc agc agc ctg acc tct gac gac tct gcg gtc     336
Thr Val Tyr Met Gln Leu Ser Ser Leu Thr Ser Asp Asp Ser Ala Val
                100                 105                 110 tat ttc tgt gca aga agg gac tat ggt gac tac ggg ttt gct tac tgg     384
Tyr Phe Cys Ala Arg Arg Asp Tyr Gly Asp Tyr Gly Phe Ala Tyr Trp
            115                 120                 125 ggc caa ggg act ctg gtc act gtc tct gca                             414
Gly Gln Gly Thr Leu Val Thr Val Ser Ala
        130                 135
```

<210> SEQ ID NO 90
<211> LENGTH: 138
<212> TYPE: PRT
<213> ORGANISM: Mus musculus

<400> SEQUENCE: 90

```
Met Gly Trp Ser Trp Ile Phe Leu Phe Leu Leu Ser Gly Thr Ala Gly
1               5                   10                  15

Val His Cys Gln Ile Gln Leu Gln Gln Ser Gly Pro Glu Leu Val Asn
            20                  25                  30

Pro Gly Ala Ser Val Lys Ile Ser Cys Lys Pro Ser Gly Tyr Thr Phe
        35                  40                  45

Thr Asp Tyr Tyr Ile Asn Trp Val Lys Gln Arg Pro Gly Gln Gly Leu
    50                  55                  60

Glu Trp Ile Gly Trp Ile His Pro Gly Gly Gly Tyr Thr Lys Tyr Asn
65                  70                  75                  80

Glu Lys Phe Arg Gly Lys Ala Thr Val Thr Val Asp Thr Ser Ala Asn
                85                  90                  95

Thr Val Tyr Met Gln Leu Ser Ser Leu Thr Ser Asp Asp Ser Ala Val
            100                 105                 110

Tyr Phe Cys Ala Arg Arg Asp Tyr Gly Asp Tyr Gly Phe Ala Tyr Trp
        115                 120                 125

Gly Gln Gly Thr Leu Val Thr Val Ser Ala
    130                 135
```

<210> SEQ ID NO 91
<211> LENGTH: 393
<212> TYPE: DNA
<213> ORGANISM: Mus musculus
<220> FEATURE:
<221> NAME/KEY: CDS
<222> LOCATION: (1)..(393)

<400> SEQUENCE: 91

```
atg gag aca gac aca ctc ctg cta tgg gtg ctg ctg ctc tgg gtt cca      48
Met Glu Thr Asp Thr Leu Leu Leu Trp Val Leu Leu Leu Trp Val Pro
1               5                   10                  15 ggt tcc aca ggt gac att gtg ctg acc caa tct cca gct tct ttg gct      96
Gly Ser Thr Gly Asp Ile Val Leu Thr Gln Ser Pro Ala Ser Leu Ala
            20                  25                  30 gtg tct cta ggg cag agg gcc acc ata tcc tgc aga gtc agt gaa agt     144
Val Ser Leu Gly Gln Arg Ala Thr Ile Ser Cys Arg Val Ser Glu Ser
        35                  40                  45 gtt gat agt tat ggc aat agt ttt atg cac tgg tac cag cag aaa cca     192
Val Asp Ser Tyr Gly Asn Ser Phe Met His Trp Tyr Gln Gln Lys Pro
    50                  55                  60 gga cag cca ccc aaa ctc ctc atc tat cgt gca tcc aac cta gaa tct     240
Gly Gln Pro Pro Lys Leu Leu Ile Tyr Arg Ala Ser Asn Leu Glu Ser
65                  70                  75                  80 ggg atc cct gac agg ttc agt ggc agt gtg tct agg aca gac ttc acc     288
Gly Ile Pro Asp Arg Phe Ser Gly Ser Val Ser Arg Thr Asp Phe Thr
                85                  90                  95 ctc acc att aat cct gtg gag cct gat gat gtt gca acc tat tac tgt     336
Leu Thr Ile Asn Pro Val Glu Pro Asp Asp Val Ala Thr Tyr Tyr Cys
            100                 105                 110 cag caa act aat gag gat cct ccg acg ttc ggt gga ggc acc aag ctg     384
Gln Gln Thr Asn Glu Asp Pro Pro Thr Phe Gly Gly Gly Thr Lys Leu
        115                 120                 125 gaa atc aaa                                                          393
Glu Ile Lys
```

```
Glu Ile Lys
    130

<210> SEQ ID NO 92
<211> LENGTH: 131
<212> TYPE: PRT
<213> ORGANISM: Mus musculus

<400> SEQUENCE: 92

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Val Ser Glu Ser
        35                  40                  45

Val Asp Ser Tyr Gly Asn Ser Phe Met His Trp Tyr Gln Gln Lys Pro
    50                  55                  60

Gly Gln Pro Pro Lys Leu Leu Ile Tyr Arg Ala Ser Asn Leu Glu Ser
65                  70                  75                  80

Gly Ile Pro Asp Arg Phe Ser Gly Ser Val Ser Arg Thr Asp Phe Thr
                85                  90                  95

Leu Thr Ile Asn Pro Val Glu Pro Asp Asp Val Ala Thr Tyr Tyr Cys
            100                 105                 110

Gln Gln Thr Asn Glu Asp Pro Pro Thr Phe Gly Gly Gly Thr Lys Leu
        115                 120                 125

Glu Ile Lys
    130

<210> SEQ ID NO 93
<211> LENGTH: 119
<212> TYPE: PRT
<213> ORGANISM: Mus musculus

<400> SEQUENCE: 93

Gln Ile Gln Leu Gln Gln Ser Gly Pro Glu Leu Val Asn Pro Gly Ala
1               5                   10                  15

Ser Val Lys Ile Ser Cys Lys Pro Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Trp Ile His Pro Gly Gly Gly Tyr Thr Lys Tyr Asn Glu Lys Phe
    50                  55                  60

Arg Gly Lys Ala Thr Val Thr Val Asp Thr Ser Ala Asn Thr Val Tyr
65                  70                  75                  80

Met Gln Leu Ser Ser Leu Thr Ser Asp Asp Ser Ala Val Tyr Phe Cys
                85                  90                  95

Ala Arg Arg Asp Tyr Gly Asp Tyr Gly Phe Ala Tyr Trp Gly Gln Gly
            100                 105                 110

Thr Leu Val Thr Val Ser Ala
        115

<210> SEQ ID NO 94
<211> LENGTH: 111
<212> TYPE: PRT
<213> ORGANISM: Mus musculus

<400> SEQUENCE: 94

Asp Ile Val Leu Thr Gln Ser Pro Ala Ser Leu Ala Val Ser Leu Gly
```

```
                1               5                  10                 15
            Gln Arg Ala Thr Ile Ser Cys Arg Val Ser Glu Ser Val Asp Ser Tyr
                            20                  25                  30
            Gly Asn Ser Phe Met His Trp Tyr Gln Gln Lys Pro Gly Gln Pro Pro
                        35                  40                  45
            Lys Leu Leu Ile Tyr Arg Ala Ser Asn Leu Glu Ser Gly Ile Pro Asp
                    50                  55                  60
            Arg Phe Ser Gly Ser Val Ser Arg Thr Asp Phe Thr Leu Thr Ile Asn
            65                  70                  75                  80
            Pro Val Glu Pro Asp Asp Val Ala Thr Tyr Tyr Cys Gln Gln Thr Asn
                                85                  90                  95
            Glu Asp Pro Pro Thr Phe Gly Gly Gly Thr Lys Leu Glu Ile Lys
                            100                 105                 110
```

<210> SEQ ID NO 95
<211> LENGTH: 5
<212> TYPE: PRT
<213> ORGANISM: Mus musculus

<400> SEQUENCE: 95

```
Asp Tyr Tyr Ile Asn
1               5
```

<210> SEQ ID NO 96
<211> LENGTH: 17
<212> TYPE: PRT
<213> ORGANISM: Mus musculus

<400> SEQUENCE: 96

```
Trp Ile His Pro Gly Gly Gly Tyr Thr Lys Tyr Asn Glu Lys Phe Arg
1               5                  10                  15
Gly
```

<210> SEQ ID NO 97
<211> LENGTH: 10
<212> TYPE: PRT
<213> ORGANISM: Mus musculus

<400> SEQUENCE: 97

```
Arg Asp Tyr Gly Asp Tyr Gly Phe Ala Tyr
1               5                  10
```

<210> SEQ ID NO 98
<211> LENGTH: 15
<212> TYPE: PRT
<213> ORGANISM: Mus musculus

<400> SEQUENCE: 98

```
Arg Val Ser Glu Ser Val Asp Ser Tyr Gly Asn Ser Phe Met His
1               5                  10                  15
```

<210> SEQ ID NO 99
<211> LENGTH: 7
<212> TYPE: PRT
<213> ORGANISM: Mus musculus

<400> SEQUENCE: 99

```
Arg Ala Ser Asn Leu Glu Ser
1               5
```

<210> SEQ ID NO 100

```
<211> LENGTH: 9
<212> TYPE: PRT
<213> ORGANISM: Mus musculus

<400> SEQUENCE: 100

Gln Gln Thr Asn Glu Asp Pro Pro Thr
1               5
```

ANTI-ERBB3 ANTIBODY

TECHNICAL FIELD

The present invention relates to an antibody or an antibody fragment thereof which recognizes an extracellular domain of erbB3 and inhibits EGF-like ligand-dependent phosphorylation of erbB3, a DNA encoding the antibody or the antibody fragment thereof, a method of producing the antibody or the antibody fragment thereof, a therapeutic drug comprising the antibody or the antibody fragment thereof, and therapeutic application using the antibody or the antibody fragment thereof.

BACKGROUND ART erbB3 is a single pass type transmembrane protein which belongs to epidermal growth factor receptor (EGFR) family (Non-Patent Documents 1, 2, and 3). The three-dimensional structure of erbB3 is similar to that of EGFR, Her2, and erbB4, and the extracellular domain thereof is constituted with four-domain structure including domains 1, 2, 3, and 4 from N-terminal. EGFR family molecules other than erbB3 have intracellular kinase domains, and kinase activity is performed when their receptors are activated, but the intracellular domain of erbB3 does not have the kinase activity.

Regarding activation of erbB3, two pathways are known which include 1. a signaling cascade in which erbB3-specific ligand heregulin binds to erbB3, erbB3 is phosphorylated due to other EGFR family forming a hetero dimer with erbB3, and then a phosphatidyl inositol-3 phosphate kinase (PI3 kinase) and Akt are activated, and 2. a signaling cascade in which EGFR family (EGFR, Her2, or the like) other than erbB3 is activated due to the binding or overexpression of the ligand, erbB3 is consequently phosphorylated, and then the PI3 kinase and Akt are activated.

The results obtained by exhaustively analyzing the affinity between the intracellular domain of EGFR family molecules and signaling proteins by using protein arrays strongly suggest that among the EGFR family molecules, erbB3 particularly shows high affinity with the PI3 kinase and plays an important role in activating the PI3 kinase (Non-Patent Document 4). In recent years, erbB3 has been reported to be involved in making cancer to be resistant to an EGFR inhibitor (Non-Patent Documents 5 and 6).

It has been clarified that in drug-resistant tumors, tumor cells keep growing in the presence of a drug since a hepatocyte growth factor receptor (HGFR or Met) causes phosphorylation of erbB3 (Non-Patent Document 5) or since Met increases the expression of erbB3 (Non-Patent Document 6).

There are several reports on correlation between the expression of erbB3 and prognosis of cancer. Chen et al. (Non-Patent Document 7) select 5 genes (DUSP6, MMD, STAT1, ERBB3, and LCK) highly correlated with the prognosis of lung cancer, based on the results of array analysis, and erbB3 is included in the selected genes.

In immunohistological analysis, the expression of erbB3 is reported to be a poor prognostic factor of lung cancer (Non-Patent Document 8). Muller-Tidow et al. (Non-Patent Document 9) investigated kinases relating to metastasis of lung cancer by array analysis, and as a result, erbB3 was identified to be a third gene highly correlated to the risk of distant metastasis after INSR and NTRK1. The expression of erbB3 is reported to be a poor prognostic factor in breast cancer (Non-Patent Document 10) and ovarian cancer (Non-Patent Document 11) in addition to lung cancer.

Regarding anti-erbB3 antibodies, an antibody which inhibits binding of heregulin to erbB3 (Non-Patent Document 12), an antibody which does not bind with erbB1 and erbB2 but specifically binds with erbB3 (Patent Document 1), an antibody which inhibits heregulin-dependent erbB2-erbB3 interaction (Patent Document 2), an antibody which binds with the extracellular domain of erbB3 (Patent Document 3), and an antibody which binds to a domain 1 of erbB3 to inhibit heregulin-dependent phosphorylation of erbB3 (Patent Document 4) are reported.

CITATION LIST

Patent Document

Patent Document 1: U.S. Pat. No. 5,480,968
Patent Document 2: U.S. Pat. No. 5,968,511
Patent Document 3: WO-A-2007/077028
Patent Document 4: WO-A-2008/100624

Non-Patent Document

Non-Patent Document 1: Harari P. M. et. al., Endocr Relat Cancer. 2004, 11, 689-708.
Non-Patent Document 2: Nagy P. et. al., Pathol Oncol Res. 1999, 5, 255-71.
Non-Patent Document 3: Hynes N. E. et. al., Nat Rev Cancer. 2005, 5, 341-54.
Non-Patent Document 4: Jones R. B. et. al., Nature. 2006, 439, 168-74.
Non-Patent Document 5: Engelman J. A. et. al., Science. 2007, 316, 1039-43.
Non-Patent Document 6: Sergina N. V. et. al., Nature. 2007, 445, 437-41.
Non-Patent Document 7: Chen H. Y. et. al., N Engl J. Med. 2007, 356, 11-20.
Non-Patent Document 8: Hilbe W. et. al., J Clin Pathol. 2003, 56, 736-41.
Non-Patent Document 9: Muller-Tidow C. Et. Al., Cancer Res. 2005, 65, 1778-82.
Non-Patent Document 10: Bieche I. et. al., Int J. Cancer. 2003, 106, 758-65.
Non-Patent Document 11: Tanner B. et. al. J Clin Oncol. 2006, 24, 4317-23.
Non-Patent Document 12: Chen et al., J Bio Chem 1996, 271, 7620-7629, 1996.

SUMMARY OF THE INVENTION

Problems to be Solved by the Invention

There is a demand for a therapeutic drug for erbB3-expressing cell-related diseases. According to the present invention, it is possible to provide an antibody or an antibody fragment thereof which inhibits EGF-like ligand-dependent phosphorylation of erbB3, a DNA encoding the antibody or the antibody fragment thereof, a method of producing the antibody or the antibody fragment thereof, a treatment method using the antibody or the antibody fragment thereof, and a therapeutic drug comprising the antibody or the antibody fragment thereof. In addition, according to the present invention, it can provide combination therapy using the anti-erbB3 antibody.

Means for Solving the Problems

The present invention relates to the following (1) to (16).

(1) An antibody or an antibody fragment thereof which specifically binds to an extracellular domain of erbB3 and inhibits epidermal growth factor (EGF)-like ligand-dependent phosphorylation of erbB3.

(2) An antibody which specifically binds to an extracellular domain of erbB3 and inhibits both erbB3-specific ligand-dependent phosphorylation of erbB3 and erbB3-specific ligand-independent phosphorylation of erbB3.

(3) The antibody or the antibody fragment thereof described in (1) or (2), wherein the phosphorylation of erbB3 is phosphorylation of erbB3 depending on at least two ligands selected from an epidermal growth factor (EGF), a transforming growth factor α (TGF-α), amphiregulin, betacellulin, epiregulin, a heparin-binding epidermal growth factor-like growth factor (HB-EGF), and heregulin.

(4) The antibody or the antibody fragment thereof described in any one of (1) to (3), wherein the extracellular domain of erbB3 is an extracellular domain comprising at least one domain selected from a domain 1 consisting of an amino acid sequence from positions 20 to 179, a domain 2 consisting of an amino acid sequence from positions 180 to 328, a domain 3 consisting of an amino acid sequence from positions 329 to 487, and a domain 4 consisting of an amino acid sequence from positions 488 to 643 in the amino acid sequence represented by SEQ ID NO:3.

(5) The antibody or the antibody fragment thereof described in any one of (1) to (4), wherein the antibody is an antibody selected from the following (a) to (c):

(a) an antibody or an antibody fragment thereof which competes with at least one antibody clone selected from a 1153 antibody clone, a 12511 antibody clone, a 920104 antibody clone, and a 1126 antibody clone, (b) an antibody or an antibody fragment thereof which binds with an epitope comprising an epitope bound by at least one antibody clone selected from the 1153 antibody clone, the 12511 antibody clone, the 920104 antibody clone, and the 1126 antibody clone, (c) an antibody or an antibody fragment thereof which binds with an epitope which is the same as the epitope bound by at least one antibody clone selected from the 1153 antibody clone, the 12511 antibody clone, the 920104 antibody clone, and the 1126 antibody clone.

(6) The antibody or the antibody fragment thereof described in any one of (1) to (5), wherein the antibody is any one of antibody selected from an antibody comprising an antibody heavy chain variable region (hereinafter, described as VH, in case) comprising the amino acid sequence represented by SEQ ID NO:57 and an antibody light chain variable region (hereinafter, described as VL, in case) comprising the amino acid sequence represented by SEQ ID NO:58, an antibody comprising an VH comprising the amino acid sequence represented by SEQ ID NO:69 and an VL comprising the amino acid sequence represented by SEQ ID NO:70, an antibody comprising an VH comprising the amino acid sequence represented by SEQ ID NO:81 and an VL comprising the amino acid sequence represented by SEQ ID NO:82, and an antibody comprising an VH comprising the amino acid sequence represented by SEQ ID NO:93 and an VL comprising the amino acid sequence represented by SEQ ID NO:94.

(7) A DNA encoding the antibody or the antibody fragment thereof described in any one of (1) to (6).

(8) A method of producing the antibody or the antibody fragment thereof described in any one of (1) to (6), comprising:

culturing a transformant obtained by introducing a vector comprising the DNA described in (7) into a cell in a medium to form and accumulate the antibody or the antibody fragment thereof described in any one of (1) to (6) in culture; and purifying the antibody or the antibody fragment thereof from the culture.

(9) An antibody composition comprising:

a first antibody or an antibody fragment thereof which binds with at least one domain selected from a domain 1 consisting of an amino acid sequence from positions 20 to 179, a domain 2 consisting of an amino acid sequence from positions 180 to 328, a domain 3 consisting of an amino acid sequence from positions 329 to 487, and a domain 4 consisting of an amino acid sequence from positions 488 to 643 in the amino acid sequence represented by SEQ ID NO:3 in the extracellular domain of erbB3; and a second antibody or an antibody fragment thereof which binds with a domain different from the domain bound by the first antibody.

(10) The antibody composition described in (9), wherein the first antibody or the antibody fragment thereof is an antibody or an antibody fragment thereof which binds with the domain 2 or 4 in the extracellular domain of erbB3.

(11) The antibody composition described in (9) or (10), wherein the second antibody or the antibody fragment thereof is an antibody or an antibody fragment thereof which binds with the domain 1 or 3 in the extracellular domain of erbB3.

(12) The antibody composition described in any one of (9) to (11), wherein the first antibody or the antibody fragment thereof is an antibody or an antibody fragment thereof selected from the following (a) to (c):

(a) an antibody or an antibody fragment thereof which competes with a 1126 antibody clone, (b) an antibody or an antibody fragment thereof which binds with an epitope comprising an epitope bound by the 1126 antibody clone, (c) an antibody or an antibody fragment thereof which binds with an epitope which is the same as the epitope bound by the 1126 antibody clone.

(13) The antibody composition described in any one of (9) to (12), wherein the second antibody or the antibody fragment thereof is an antibody or an antibody fragment thereof selected from the following (a) to (c):

(a) an antibody or an antibody fragment thereof which competes with a 1153 antibody clone, (b) an antibody or an antibody fragment thereof which binds with an epitope comprising an epitope bound by the 1153 antibody clone, (c) an antibody or an antibody fragment thereof which binds with an epitope which is the same as the epitope bound by the 1153 antibody clone.

(14) A method of treating a disease related to an erbB3-expressing cell, comprising using the antibody composition described in any one of (9) to (13).

(15) The method described in (14), wherein the disease related to an erbB3-expressing cell is cancer.

(16) A drug for treating a disease related to an erbB3-expressing cell, comprising:

the antibody composition described in any one of (9) to (13).

Effect of the Invention

According to the present invention, it is possible to provide an antibody or an antibody fragment thereof which recognizes the extracellular domain of erbB3 and inhibit EGF-like ligand-dependent phosphorylation of erbB3, a DNA encoding the antibody or the antibody fragment thereof, a method of producing the antibody or the antibody fragment thereof, a therapeutic drug comprising the antibody or the antibody fragment thereof, and therapeutic application using the antibody or the antibody fragment thereof.

BRIEF DESCRIPTION OF DRAWINGS

FIG. 2(a) shows amphiregulin- or betacellulin-dependent phosphorylation of erbB3.

FIG. 3(a) shows epiregulin-dependent phosphorylation of erbB3.

EMBODIMENTS FOR CARRYING OUT THE INVENTION

Figure 1:
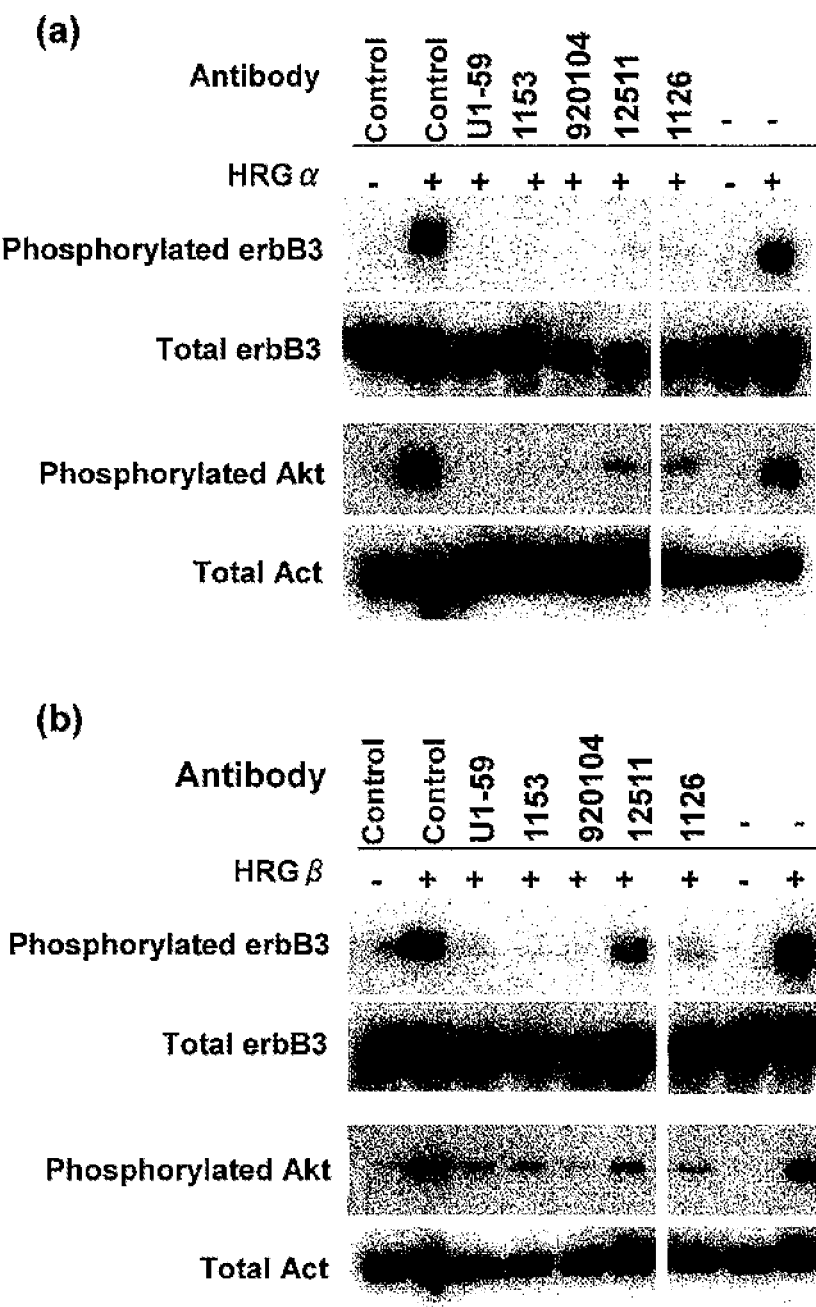
FIG. 1(a) shows the inhibitory effect of the anti-human erbB3 antibody on heregulin α (HRG α)-dependent phosphorylation of erbB3 and Akt phosphorylation in the human squamous carcinoma cell line A431.
FIG. 1(b) shows the inhibitory effect of the anti-human erbB3 antibody on heregulin β (HRG β)-dependent phosphorylation of erbB3 and Akt phosphorylation in the human squamous carcinoma cell line A431. Figure (a) shows heregulin α-dependent phosphorylation, Figure (b) shows heregulin β-dependent phosphorylation, and phosphorylated erbB3, total erbB3 proteins, phosphorylated Akt, and total Akt proteins are shown from the top. Moreover, the antibodies used are shown in the uppermost portion of figures (a) and (b).

The antibody of the present invention relates to an antibody or an antibody fragment thereof which specifically binds to the extracellular domain (abbreviated to ECD in some cases) of erbB3 and inhibits EGF-like ligand-dependent phosphorylation of erbB3.

erbB3 is a member of an epidermal growth factor receptor (EGFR) family (also referred to as a HER family or an erbB family) which is a tyrosine kinase type receptor family. erbB3 is also called as erbB3 receptor, epidermal growth factor receptor 3 (EGFR3), a HER3 receptor, or Her3 receptor, or simply also called as HER3 or Her3. erbB3 is a single pass type transmembrane protein. erbB3 includes a ligand-binding domain and a dimer-forming domain in the extracellular domain and includes a tyrosine phosphorylation domain in its intracellular domain. It is known that when heregulin known as a erbB3-specific ligand binds to the ligand-binding domain of the extracellular domain, dimerization of erbB3 is caused, whereby a cell growth signal is sent.

Particularly, it is known that a heterodimer formed between erbB3 and erbB 1 (EGFR1 or HER1), erbB2 (EGFR2, HER2, or Neu), or erbB4 (EGFR4 or HER4) which is other member of the EGF receptor (EGFR) family is involved in cell growth.

In the present invention, erbB3 refers to a polypeptide comprising the amino acid sequence suggested by Kraus et al. (Proc. Nat. Acad. Sci. 86: 9193-9197, 1989.). Specifically, erbB3 refers to a membrane protein comprising the amino acid sequence represented by SEQ ID NO:2 and a membrane protein comprising the amino acid sequence represented by SEQ ID No:3.

The information on the amino acid sequence of erbB3 is available from a known database such as NCBI (http://www.ncbi.nlm.nih.gov/), and examples thereof include human erbB3 (NCBI accession No. NP_001973.2) comprising the amino acid sequence represented by SEQ ID NO:2, mouse erbB3 (NCBI accession No. NP_034283.1) comprising the amino acid sequence represented by SEQ ID NO:5, and the like.

Examples of erbB3 in the present invention include a polypeptide which consists of an amino acid sequence formed by deletion, substitution, or addition of one or more amino acids in the amino acid sequence represented by SEQ ID NO:2 and has the function of erbB3.

The erbB3 of the present invention also includes a polypeptide which comprises an amino acid sequence 70% or more, preferably 80% or more, even more preferably 90% or more, and most preferably 95%, 96%, 97%, 98%, and 99% or more homologous to the amino acid sequence represented by SEQ ID NO:2 and has the function of erbB3.

The polypeptide comprising the amino acid sequence formed by deletion, substitution, or addition of one or more amino acids in the amino acid sequence represented by SEQ ID NO:2 can be obtained by, for example, introducing site-specific mutation to the DNA encoding the amino acid sequence represented by SEQ ID NO:2, by using the method of introducing site-specific mutation [Molecular Cloning, A Laboratory Manual, Second Edition, Cold Spring Harbor Laboratory Press (1989), Current Protocols in Molecular Biology, John Wiley & Sons (1987-1997), Nucleic Acids Research, 10, 6487 (1982), Proc. Natl. Sci. Acad. USA, 79, 6409 (1982), Gene, 34, 315 (1985), Nucleic Acids Research, 13, 4431 (1985), Proc. Natl. Acad. Sci. USA, 82, 488 (1985)] and the like. Though unrestricted particularly, the number of the amino acids deleted, substituted, or added is preferably one to dozens of amino acids, for example, 1 to 20, and more preferably one to several amino acids, for example, 1 to 5.

Examples of a gene encoding erbB3 includes a nucleotide sequence of the human erbB3 shown at positions 277 to 4305 of the nucleotide sequence represented by SEQ ID NO:1 (NCBI accession No. NM_001982.3), and a nucleotide sequence of the mouse erbB3 shown in SEQ ID NO:4 (NCBI accession No. NM_010153.1).

The gene encoding erbB3 of the present invention also includes a gene having DNA encoding a polypeptide which consists of a nucleotide sequence formed by deletion, substitution, or addition of one or more nucleotides in the nucleotide sequence from positions 277 to 4305 represented by SEQ ID NO:1 and has the function of erbB3, a gene having DNA encoding a polypeptide which consists of a nucleotide sequence at least 60% or more, preferably 70% and 80% or more, and even more preferably 90%, 95%, 96%, 97%, 98%, and 99% or more homologous to the nucleotide sequence from positions 277 to 4305 represented by SEQ ID NO:1 and has the function of erbB3, a gene having DNA encoding a polypeptide which consists of DNA hybridized with DNA from positions 277 to 4305 represented by SEQ ID NO:1 under a stringent condition and has the function of erbB3, and the like.

In the present invention, the DNA which hybridizes under stringent conditions refers to a DNA which is obtained by colony hybridization, plaque hybridization, Southern blot hybridization, DNA microarray analysis, or the like using a DNA comprising the nucleotide sequence from positions 277 to 4305 represented by SEQ ID NO:1 as a probe.

A specific example of such DNA is a DNA which can be identified by performing hybridization at 65° C. in the presence of 0.7 to 1.0 mol/L sodium chloride using a filter or a slide glass with colony- or plaque-derived DNA, PCR products or oligo DNA encoding the DNA sequence immobilized thereon, and then washing the filter or a slide glass at 65° C. with a 0.1 to 2-fold concentration SSC solution (1-fold concentration SSC solution: 150 mmol/L sodium chloride and 15 mmol/L sodium citrate). Hybridization can be carried out according to the methods described in Molecular Cloning, A Laboratory Manual, Second Edition, Cold Spring Harbor Laboratory Press (1989), Current Protocols in Molecular Biology, John Wiley & Sons (1987-1997); DNA Cloning 1: Core Techniques, A Practical Approach, Second Edition, Oxford University (1995); and the like.

Specifically, the DNA capable of hybridization includes DNA having at least 60% or more homology, preferably 70%, 80% or more homology, and more preferably 90%, 95%, 96%, 97%, 98%, 99% or more homology to the nucleotide sequence from positions 277 to 4305 represented by SEQ ID NO:1.

In the nucleotide sequence of the gene encoding a protein of a eukaryote, genetic polymorphism is often recognized. The erbB3 gene used in the present invention also includes a gene in which small modification is generated in the nucleotide sequence by such polymorphism.

The number of the homology described in the present invention may be a number calculated by using a homology search program known by the skilled person, unless otherwise indicated. Regarding the nucleotide sequence, the number may be calculated by using a default parameter in BLAST [*J. Mol. Biol.*, 215, 403 (1990)] or the like, and regarding the amino acid sequence, the number may be calculated by using a default parameter in BLAST2 [*Nucleic Acids Res.*, 25, 3389 (1997); *Genome Res.*, 7, 649 (1997); http://www.ncbi.nlm.nih.gov/Education/BLASTinfo/information3.html] or the like.

As the default parameter, G (cost to open gap) is 5 for the nucleotide sequence and 11 for the amino acid sequence; –E (cost to extend gap) is 2 for the nucleotide sequence and 1 for the amino acid sequence; –q (penalty for nucleotide mismatch) is –3; –r (reward for nucleotide match) is 1; –e (expect value) is 10; –W (wordsize) is 11 residues for the nucleotide sequence and 3 residues for the amino acid sequence; –y (Dropoff (X) for blast extensions in bits) is 20 for blastn and 7 for a program other than blastn; –X (X dropoff value for gapped alignment in bits) is 15; and Z (final X dropoff value for gapped alignment in bits) is 50 for blastn and 25 for a program other than blastn (http://www.ncbi.nlm.nih.gov/blast/html/blastcgihelp.html).

The polypeptide comprising a partial sequence of the amino acid sequence represented by SEQ ID NO: 2 can be prepared according to a method known by the skilled person. For example, it can be prepared by deleting a part of DNA encoding the amino acid sequence represented by SEQ ID NO: 2 and culturing a transformant into which an expression vector comprising the DNA is introduced.

Also, based on the thus prepared polypeptide or DNA, a polypeptide comprising an amino acid sequence in which one or more amino acid(s) is/are deleted, substituted or added in a partial sequence of the amino acid sequence represented by SEQ ID NO: 2 can be prepared in the same manner as described above.

The polypeptide comprising a partial sequence of the amino acid sequence represented by SEQ ID NO: 2; or the polypeptide comprising an amino acid sequence in which at least one amino acid is deleted, substituted or added in a partial sequence of the amino acid sequence represented by SEQ ID NO: 2 can also be produced by a chemical synthesis method such as fluorenylmethoxycarbonyl (Fmoc) method or t-butyloxycarbonyl (tBoc) method.

The extracellular domain of human erbB3 of the present invention includes, for example, domains predicted by using the amino acid sequence represented by SEQ ID NO: 2 with conventionally known transmembrane domain prediction program SOSUI (http://bp.nuap.nagoya-u.ac.jp/sosui/sosui_submit.html), TMHMM ver. 2 (http://www.cbs.dtu.dk/services/TMHMM-2.0/) or ExPASy Proteomics Server (http://Ca.expasy.org/). Specific examples thereof include domains predicted with ExPASy Proteomics Server.

The extracellular domain (ECD) of erbB3 is divided into domains 1 to 4 (D1 to D4), and it is known that domains 1 and 3 play an important role in ligand binding, and domain 2 plays an important role in dimer formation, similarly to other EGFR family. Specifically, an amino acid sequence from positions 20 to 179 in the amino acid sequence represented by SEQ ID NO:3 forms the domain 1, an amino acid sequence from positions 180 to 328 forms the domain 2, an amino acid sequence from positions 329 to 487 forms the domain 3, and an amino acid sequence from positions 488 to 643 forms the domain 4.

The EGF-like ligand refers to the EGF ligand family binding to the EGFR family. Specific examples thereof include an epidermal growth factor (EGF), a transforming growth factor α (TGF-α), amphiregulin, betacellulin, epiregulin, a heparin-binding epidermal growth factor-like growth factor (HB-EGF), NTAK, and heregulin (neuregulin).

In the present invention, examples of functions of erbB3 include a function of promoting cell growth and differentiation resulting from phosphorylation of the erbB3, followed by homodimerization and heterodimerization of erbB3 is induced depending on binding of heregulin. To confirm such a function of erbB3, a target protein is introduced to a host cell to prepare a protein-expressing cell, whereby the ligand-dependent effect can be confirmed under appropriate cell culture conditions.

Examples of the antibody of the present invention include an antibody which specifically binds to the extracellular domain of erbB3 and inhibits EGF-like ligand-dependent phosphorylation of erbB3, an antibody which specifically binds to the extracellular domain of erbB3 and inhibits both the erbB3-specific ligand-dependent phosphorylation of erbB3 and the erbB3-specific ligand-independent phosphorylation of erbB3.

In the present invention, the erbB3-specific ligand-dependent phosphorylation of erbB3 refers to phosphorylation of tyrosine residues of the intracellular domain of erbB3, which is caused when heregulin known as an erbB3-specific ligand binds to the extracellular domain of erbB3.

In the present invention, the erbB3-specific ligand-independent phosphorylation of erbB3 refers to phosphorylation of tyrosine residues of the intracellular domain of erbB3, which is caused when the EGF-like ligand including heregulin as the erbB3-specific ligand binds to the extracellular domain of erbB family other than erbB3 and a heterodimer is formed between the erbB family and erbB3. The erbB3-specific ligand-independent phosphorylation of erbB3 can also be referred to as indirect phosphorylation of erbB3 caused depending on the EGF-like ligand.

The antibody of the present invention can simultaneously inhibit the erbB3-specific ligand-dependent/independent phosphorylation of erbB3 described above.

Specific examples of the antibody include an antibody which inhibits the phosphorylation of erbB3 caused depending on at least 2, 3, 4, 5, or 6 ligands selected from an epidermal growth factor (EGF), a transforming growth factor α (TGF-α), amphiregulin, betacellulin, epiregulin, a heparin-binding epidermal growth factor-like growth factor (HB-EGF), NTAK, and heregulin (neuregulin). Preferably, the examples include an antibody which inhibits the phosphorylation of erbB3 caused depending on all types of EGF-like ligands.

Examples of the antibody of the present invention include an antibody binding to the extracellular domain which comprises at least one domain selected from the domain 1 consisting of an amino acid sequence from positions 20 to 179 in the amino acid sequence represented by SEQ ID NO:3, the domain 2 consisting of an amino acid sequence from positions 180 to 328, the domain 3 consisting of an amino acid sequence from positions 329 to 487, and the domain 4 consisting of an amino acid sequence from positions 488 to 643. The examples preferably includes an antibody binding to the extracellular domain comprising at least one domain of the domains 2 and 4, and more preferably includes an antibody binding to the extracellular domain comprising the domain 2, and an antibody binding to the extracellular domain comprising the domain 4.

Examples of the antibody of the present invention also include an antibody binding to epitopes present in the respective domains from D1 to D4 in the extracellular domain of erbB3.

Moreover, examples of the antibody of the present invention include an antibody which can inhibit dimerization of the erbB3, and an antibody which can inhibit heterodimerization caused between erbB3 and other erbB family (erbB1, erbB2, and erbB4). The examples specifically include an antibody which can inhibit the interaction of at least one combination selected from erbB3-erbB1, erbB3-erbB2, and erbB3-erbB4.

Examples of the antibody of the present invention also include an antibody which inhibits the phosphorylation of erbB3 caused depending on interaction of a growth factor receptor with erbB3. Specific examples thereof include an antibody which inhibits phosphorylation of erbB3 depending on hepatocyte growth factor (HGF) receptor (c-Met).

The antibody of the present invention also comprises all of monoclonal antibodies, oligoclonal antibodies, and polyclonal antibodies.

In the present invention, monoclonal antibodies refer to antibodies which monoclonal antibody-producing cells secret. The monoclonal antibody recognizes only a single epitope (also referred to as an "antigen determinant"), and the amino acid sequence (primary structure) constituting monoclonal antibodies is uniform. The oligoclonal antibody or polyclonal antibody is an antibody mixture including two or more monoclonal antibodies.

Examples of the epitope include a single amino acid sequence which the monoclonal antibody recognizes for binding, a three-dimensional structure consisting of an amino acid sequence, a sugar chain-bound amino acid sequence, a three-dimensional structure consisting of a sugar chain-bound amino acid sequence, and the like. The three-dimensional structure is a three-dimensional structure of naturally occurring proteins, which refers to a three-dimensional structure constituted with proteins expressed intracellularly or on a cell membrane.

The epitope which the antibody of the present invention recognizes is, for example, an epitope present on erbB3 expressed on a cell membrane. Examples thereof include a primary structure consisting of the amino acid sequence of erbB3, a three-dimensional structure consisting of the amino acid sequence of erbB3, a three-dimensional structure formed when a sugar chain binds to the amino acid sequence of erbB3, amino acid residues on a three dimensional structure which is specified as a result of crystal structure analysis for EGFR family proteins, and the like.

Antibody molecules are also called immunoglobulin (hereinbelow, described as "Ig"). Human antibodies are classified into isotypes including IgA1, IgA2, IgD, IgE, IgG1, IgG2, IgG3, IgG4, and IgM according to the difference between molecular structures. IgG1, IgG2, IgG3, and IgG4 which are relatively highly homologous to each other in terms of the amino acid sequence are also collectively called IgG.

An antibody molecule is constituted with polypeptides called a heavy chain (hereinbelow, described as an "H-chain") and a light chain (hereinbelow, described as an "L-chain"). The H chain is constituted with an H-chain variable region (also described as "VH") and an H-chain constant region (also described as "CH") from the N-terminal, and the L chain is constituted with an L-chain variable region (also described as "VL") and an L-chain constant region (also described as "CL") from the N-terminal respectively.

Regarding CH, α, δ, ε, γ, and μ chains are known for each subclasses. Furthermore, CH is constituted with the respective domains including a CH1 domain, a hinge domain, a CH2 domain, and a CH3 domain from the N-terminal.

A domain refers to a functional structural unit constituting each polypeptide of antibody molecules. The CH2 domain and the CH3 domain are collectively called an Fc region or simply Fc. For CL, a Cλ chain and a Cκ chain are known.

The CH1 domain, hinge domain, CH2 domain, CH3 domain, and Fc region in the present invention can be identified by the number of amino acid residues from the N-terminal according to the EU index [Kabat et al., Sequences of Proteins of Immunological Interest, US Dept. Health and Human Services (1991)]

Specifically, CH1 is identified by the amino acid sequence from positions 118 to 215 in the EU index, the hinge is identified by the amino acid sequence from positions 216 to 230 in the EU index, CH2 is identified by the amino acid sequence from positions 231 to 340 of the EU index, and CH3 is identified by the amino acid sequence from positions 341 to 447 in the EU index, respectively.

The antibody of the present invention also comprises particularly a human chimeric antibody (hereinbelow, also simply described as a "chimeric antibody"), a humanized antibody (also called "Complementarity Determining Region (CDR)-grafted antibody"), and a recombinant antibody such as a human antibody.

A chimeric antibody refers to an antibody consists of VH and VL of an antibody of an animal other than human beings (non-human animal) and CH and CL of a human antibody. Any type of animals such as a mouse, rat, hamster, and rabbit can be used as the non-human animal as long as a hybridoma can be prepared.

A hybridoma refers to a cell which is formed by fusing a myeloma cell derived from a mouse and the like with a B cell obtained by immunizing a non-human animal with an antigen, and produces a monoclonal antibody having desired antigen specificity. Accordingly, a variable region constituting the antibody produced from the hybridoma consists of an amino acid sequence of a non-human animal antibody.

A human chimeric antibody can be produced in the following manner. That is, cDNA encoding VH and VL is obtained from a hybridoma derived from non-human animal cells producing monoclonal antibodies, the cDNA is inserted to each of expression vectors for animal cells having DNA encoding CH and CL of a human antibody so as to construct a human chimeric antibody expression vector, and this vector is introduced to animal cells to express the human chimeric antibody.

A humanized antibody refers to an antibody which is obtained by grafting the amino acid sequence of CDR of VH and VL of a non-human animal antibody to CDR corresponding to VH and VL of a human antibody. The region other than CDR of VH and VL is called a framework region (hereinbelow, described as "FR").

A humanized antibody can be produced in the following manner. That is, cDNA encoding an amino acid sequence of VH which consists of an amino acid sequence of CDR of VH of a non-human antibody and an amino acid sequence of FR of VH of any human antibody, and cDNA encoding an amino acid sequence of VL which consists of an amino acid sequence of CDR of VL of a non-human animal antibody and an amino acid sequence of FR of VL of any human antibody are constructed, these cDNAs are inserted respectively into expression vectors for animal cells having DNA encoding CH and CL of a human antibody so as to construct a humanized antibody expression vector, and this vector is inserted into animal cells to express the humanized antibody.

A human antibody originally refers to an antibody naturally existing in the human body. However, the human antibody also comprises antibodies obtained from a human antibody phage library and human antibody-producing transgenic animals prepared according to the technical advancement in genetic engineering, cell engineering, and development engineering in recent years.

The human antibody can be obtained by immunizing a mouse human immunoglobulin genes integrated (Tomizuka K. et al., Proc Natl Acad Sci USA. 97, 722-7, 2000) with a desired antigen. In addition, by selecting a human antibody having a desired binding activity by using a phage display library which is formed by antibody gene amplification from human B cells, it is possible to obtain human antibodies without performing immunization (Winter G. et al., Annu Rev Immunol. 12:433-55. 1994). Moreover, by immortalizing human B cells by using an EB virus to prepare human antibody-producing cells having a desired binding activity, it is possible to obtain human antibodies (Rosen A. et al., Nature 267, 52-54. 1977).

The antibody existing in the human body can be purified in the following manner, for example. That is, lymphocytes isolated from the human peripheral blood are immortalized by being infected with the EB virus or the like, followed by cloning, whereby lymphocytes producing the antibody can be cultured and the antibody can be purified from the culture.

The human antibody phage library is a library of phages which are caused to express antibody fragments such as Fab and scFv on the surface thereof by insertion of antibody genes prepared from the human B cells into the gene of the phage. From this library, it is possible to recover phages which express antibody fragments having a desired antigen binding activity, by using binding activity with respect to an antigen-immobilized substrate as an index. The antibody fragments can also be converted into a human antibody molecule consisting of two complete H chains and two complete L chains by genetic engineering technique.

The human antibody-producing transgenic animal refers to an animal obtained by inserting the human antibody gene into chromosomes of a host animal. Specifically, the human antibody gene is introduced to mouse ES cells, the ES cells are grafted to the early embryo of another mouse, and then the embryo is developed, whereby the human antibody-producing transgenic animal can be prepared. As a method of preparing human antibodies from the human antibody-producing transgenic animal, a human antibody-producing hybridoma is obtained by a normal hybridoma preparation method which is implemented using a mammal other than a human being, followed by culture, whereby human antibodies can be produced and accumulated in the culture.

The amino acid sequence of VH and VL of the antibody of the present invention may be any of an amino acid sequence of VH and VL of a human antibody, an amino acid sequence of VH and VL of a non-human animal antibody, and an amino acid sequence of humanized antibody obtained by grafting CDR of a non-human animal antibody to the framework of a human antibody. Specific examples thereof include an amino acid sequence of VH and VL of a non-human animal antibody produced from a hybridoma, an amino acid sequence of VH and VL of a humanized antibody, an amino acid sequence of VH and VL of a human antibody, and the like.

The amino acid sequence of CL of the antibody of the present invention may be any of amino acid sequences of a human antibody and a non-human animal antibody. However, the amino acid sequence is preferably Cκ or Cλ of an amino acid sequence of a human antibody.

Any types of chain may be used as CH of the antibody of the present invention so long as the chain belongs to immunoglobulin. Preferably, any of γ1 (IgG1), γ2 (IgG2), γ3 (IgG3), and γ4 (IgG4) belongs to the IgG class can be used.

Effector activity refers to antibody-dependent activity caused via the Fc region of an antibody. As the effector activity, Antibody-Dependent Cellular Cytotoxicity activity (ADCC activity), Complement-Dependent Cytotoxicity activity (CDC activity), Antibody-Dependent Phagocytosis activity (ADP activity) caused by phagocytic cell such as a macrophage or a dendritic cell, and the like are known. In the present invention, the ADCC and CDC activities can be measured using known measurement methods [Cancer Immunol. Immunother., 36, 373 (1933)].

The ADCC activity refers to an activity in which an antibody having bound to an antigen on a target cell binds to an Fc receptor of an immunocyte via the Fc region of the antibody, thereby activating the immunocyte (a natural killer cell or the like) and damaging the target cell.

The Fc receptor (hereinbelow, described as "FcR" in some cases) refers to a receptor binding to the Fc region of an antibody, and induces various types of effector activity due to the binding of an antibody. FcR corresponds to antibody subclasses, and IgG, IgE, IgA, and IgM specifically bind to FcγR, FcεR, FcαR, and FcµR respectively.

FcγR has subtypes including FcγRI(CD64), FcγRII(CD32), and FcγRIII(CD16), and the subtypes respectively have isoforms including FcγRIA, FcγRIB, FcγRIC, FcγRIIA, FcγRIIB, FcγRIIC, FcγRIIIA, and FcγRIIIB. These different types of FcγR exist on different cells [Annu Rev. Immunol. 9:457-492 (1991)].

In human beings, FcγRIIIB is specifically expressed in neutrophils, and FcγRIIIA is expressed in monocytes, Natural Killer cells (NK cells), and a portion of T cells. The antibody binding caused via FcγRIIIA induces NK cell-dependent ADCC activity.

The CDC activity refers to an activity in which an antibody having bound to an antigen on a target cell activates a series of cascades (complement activation pathways) consisting of a group of complement-related proteins in the blood, thereby damaging the target cell. By the protein fragments generated due to the complement activation, it is possible to induce migration and activation of immunocytes. When C1q having a binding domain for the Fc region of an antibody binds to the Fc region, and C1r and C1s as two serine proteases bind thereto, a C1 complex is formed, whereby the cascade of CDC activity begins Specific examples of the antibody of the present invention include an antibody which comprises VH comprising the amino acid sequence represented by SEQ ID NO:57 and VL comprising the amino acid sequence represented by SEQ ID NO:58, an antibody which comprises VH comprising the amino acid sequence represented by SEQ ID NO:69 and VL comprising the amino acid sequence represented by SEQ ID NO:70, an antibody which comprises VH comprising the amino acid sequence represented by SEQ ID NO:81 and VL comprising the amino acid sequence represented by SEQ ID NO:82, an antibody which comprises VH comprising the amino acid sequence represented by SEQ ID NO:93 and VL comprising the amino acid sequence represented by SEQ ID NO:94, an antibody which comprises H-chain CDRs 1 to 3 comprising the amino acid sequences represented by SEQ ID NOS:59 to 61 respectively and L-chain CDRs 1 to 3 comprising the amino acid sequences represented by SEQ ID NOS:62 to 64 respectively, an antibody which comprises H-chain CDRs 1 to 3 comprising the amino acid sequences represented by SEQ ID NOS:71 to 73 respectively and L-chain CDRs 1 to 3 comprising the amino acid sequences represented by SEQ ID NOS:74 to 76 respectively, an antibody which comprises H-chain CDRs 1 to 3 comprising the amino acid sequences represented by SEQ ID NOS:83 to 85 respectively and L-chain CDRs 1 to 3 comprising the amino acid sequences represented by SEQ ID NOS:86 to 88 respectively, an antibody which comprises H-chain CDRs 1 to 3 comprising the amino acid sequences represented by SEQ ID NOS:95 to 97 respectively and L-chain CDRs 1 to 3 comprising the amino acid sequences represented by SEQ ID NOS:98 to 100 respectively, and the like.

Examples of the antibody of the present invention also include a 1153 antibody clone which comprises H-chain CDRs 1 to 3 comprising the amino acid sequences represented by SEQ ID NOS:59 to 61 respectively and L-chain CDRs 1 to 3 comprising the amino acid sequences represented by SEQ ID NOS:62 to 64 respectively, a 920104 antibody clone which comprises H-chain CDRs 1 to 3 comprising the amino acid sequences represented by SEQ ID NOS:71 to 73 respectively and L-chain CDRs 1 to 3 comprising the amino acid sequences represented by SEQ ID NOS:74 to 76 respectively, a 1126 antibody clone which comprises H-chain CDRs 1 to 3 comprising the amino acid sequences represented by SEQ ID NOS:83 to 85 respectively and L-chain CDRs 1 to 3 comprising the amino acid sequences represented by SEQ ID NOS:86 to 88 respectively, and a 12511 antibody clone which comprises H-chain CDRs 1 to 3 comprising the amino acid sequences represented by SEQ ID NOS:95 to 97 respectively and L-chain CDRs 1 to 3 comprising the amino acid sequences represented by SEQ ID NOS:98 to 100 respectively.

Examples of the recombinant antibody of the present invention include an antibody which comprises H-chain CDRs 1 to 3 comprising the amino acid sequences represented by SEQ ID NOS:59 to 61 respectively and L-chain CDRs 1 to 3 comprising the amino acid sequences represented by SEQ ID NOS:62 to 64 respectively, an antibody which comprises H-chain CDRs 1 to 3 comprising the amino acid sequences represented by SEQ ID NOS:71 to 73 respectively and L-chain CDRs 1 to 3 comprising the amino acid sequences represented by SEQ ID NOS:74 to 76 respectively, an antibody which comprises H-chain CDRs 1 to 3 comprising the amino acid sequences represented by SEQ ID NOS:83 to 85 respectively and L-chain CDRs 1 to 3 comprising the amino acid sequences represented by SEQ ID NOS:86 to 88 respectively, an antibody which comprises H-chain CDRs 1 to 3 comprising the amino acid sequences represented by SEQ ID NOS:95 to 97 respectively and L-chain CDRs 1 to 3 comprising the amino acid sequences represented by SEQ ID NOS:98 to 100 respectively, and the like.

Examples of the antibody of the present invention include the following antibodies (a) to (c).

(a) An antibody or an antibody fragment thereof which competes with any one of antibody clones selected from the 1153 antibody clone, the 12511 antibody clone, the 920104 antibody clone, and the 1126 antibody clone.

(b) An antibody or an antibody fragment thereof which binds with an epitope comprising an epitope bound by any one of antibody clones selected from the 1153 antibody clone, the 12511 antibody clone, the 920104 antibody clone, and the 1126 antibody clone.

(c) An antibody or an antibody fragment thereof which binds with an epitope which is the same as the epitope bound by any one of antibody clones selected from the 1153 antibody clone, the 12511 antibody clone, the 920104 antibody clone, and the 1126 antibody clone.

Examples of the antibody of the present invention also include an antibody which binds to the extracellular domain of erbB3 competed with the antibody described above, an antibody which binds with an epitope comprising an epitope present in the extracellular domain of erbB3 bound by the antibody described above, and an antibody which binds with the same epitope as the epitope present in the extracellular domain of erbB3 bound by the antibody described above.

In the present invention, the "antibody which binds with an epitope comprising an epitope with which any one of antibody clones selected from the 1153 antibody clone, the 12511 antibody clone, the 920104 antibody clone, and the 1126 antibody clone binds" refers to a second antibody bound to a second epitope comprising a first epitope which binds with a first antibody selected from the 1153 antibody clone, the 12511 antibody clone, the 920104 antibody clone, and the 1126 antibody clone.

The antibody of the present invention also comprises an Fc fusion protein which is a combination of Fc and an antibody fragment, an Fc fusion protein (also referred to as an immunoadhesin) which is a combination of Fc and a naturally occurring ligand or receptor, an Fc fusion protein formed by the fusion of a plurality of Fc regions, and the like. Moreover, an amino acid residue-modified Fc region in which amino acid residues are modified to enhance or suppress the effector activity of an antibody, to stabilize an antibody, and to control the half life in blood can be used for the antibody of the present invention.

Examples of the antibody of the present invention also include an antibody or an antibody fragment thereof which binds with at least two domains selected from domains 1 to 4 in the extracellular domain of erbB3 comprising the amino acid sequence represented by SEQ ID NO:3. The examples specifically include an antibody which binds with at least one combination selected from domains 1 and 2, domains 1 and 3, domains 1 and 4, domains 2 and 3, domains 2 and 4, and domains 3 and 4. Among these, an antibody which binds with at least one combination selected from domains 1 and 2, domains 1 and 4, domains 2 and 3, and domains 3 and 4 is preferable, and an antibody which binds with domains 1 and 4 is more preferable.

The antibody binding with two domains in the extracellular domain of erbB3 can be prepared by known techniques of preparing bispecific antibodies and polyvalent (multivalent) antibodies (WO 1998/050431, WO 2001/7734, WO 2002/002773, and WO 2009/131239).

Examples of the antibody fragment of the present invention include Fab, Fab', F(ab')$_2$, scFv, Diabody, dsFv, a peptide including CDR, and the like.

Fab refers to an antibody fragment having about a half H-chain of the N-terminal and a full L-chain which are bound to each other via a disulfide bond (S—S bond), a molecular weight of about 50000 and an antigen binding activity, among fragments (cleaved with an amino acid residue at position 224 of the H-chain) which are obtained by treating the IgG antibody with a protease papain.

F(ab')$_2$ refers to an antibody fragment which is slightly longer than Fab fragments bound to each other via a S—S bond of the hinge region and has a molecular weight of about 100000 and an antigen binding activity, among fragments (cleaved with an amino acid residue at position 234 of the H-chain) which are obtained by treating IgG with a protease pepsin.

Fab' is an antibody fragment which is obtained by cleaving the S—S bond of the hinge region of the F(ab')$_2$ and has a molecular weight of about 50000 and an antigen binding activity.

scFV is an antibody fragment having an antigen binding activity, which is a VH-P-VL or VL-P-VH polypeptide obtained by linking one VH to one VL by using an appropriate peptide linker (P) consisting of 12 or more residues.

Diabody is an antibody fragment as a dimer formed of scFVs showing the same or different antigen binding specificity, and this antibody fragment has a divalent antigen binding activity with respect to the same antigen or has a 2 types of specific antigen binding activity with respect to two different types of antigens.

dsFv refers to a fragment which is obtained by binding polypeptides, which are formed by substituting one amino acid residue of each of VH and VL with a cysteine residue, via the S—S bond between the respective cysteine residues.

The peptide comprising CDR is constituted with at least one or more regions of CDR of VH or VL. In the peptide comprising a plurality of CDRs, the CDRs can be bound to each other directly or via an appropriate peptide linker.

The peptide comprising CDR can be produced in the following manner. That is, DNA encoding CDR of VH and VL of the engineered antibody of the present invention is constructed, the DNA is inserted into an expression vector for prokaryotes or an expression vector for eukaryotes, and the expression vector is introduced into a prokaryote or a eukaryote to express and produce the peptide. Moreover, the peptide comprising CDR can also be produced by chemical synthesis methods such as an Fmoc method and a tBoc method.

Examples of the antibody composition of the present invention include an antibody composition (or mixture) and the like comprising two or more antibodies or the antibody fragments thereof described above. The examples specifically include an antibody composition which comprises a first antibody or an antibody fragment thereof binding with the extracellular domain including at least one domain selected from the domains 1 to 4 in the extracellular domain of erbB3 comprising the amino acid sequence represented by SEQ ID NO:1 and a second antibody or an antibody fragment thereof binding with a domain different from the domain binding with the first antibody, and the like. Among these, an antibody composition is preferable in which the first antibody is an antibody binding with the domain 4 or 2 of erbB3 and the second antibody is an antibody binding with the domain 1 or 3 of erbB3, and an antibody composition or the like is more preferable in which the first antibody is an antibody binding with the domain 4 of erbB3 and the second antibody is an antibody binding with the domain 1 of erbB3.

The first antibody described above is preferably an antibody or an antibody fragment thereof selected from the following (a) to (c).

(a) An antibody or an antibody fragment thereof which competes with the 1126 antibody clone.

(b) An antibody or an antibody fragment thereof which binds with an epitope comprising an epitope bound by the 1126 antibody clone.

(c) An antibody or an antibody fragment thereof which binds with an epitope which is the same as the epitope bound by the 1126 antibody clone.

The second antibody described above is preferably an antibody or an antibody fragment thereof selected from the following (a) to (c).

(a) An antibody or an antibody fragment thereof which competes with the 1153 antibody clone.

(b) An antibody or an antibody fragment thereof which binds with an epitope comprising an epitope bound by the 1153 antibody clone.

(c) An antibody or an antibody fragment thereof which binds with an epitope which is the same as the epitope bound by the 1153 antibody clone.

The antibody composition of the present invention can inhibit a binding of the erbB3-specific ligand to erbB3 and simultaneously dimerization (homodimerization and heterodimerization) caused between erbB3 and erbB family.

The antibody of the present invention includes antibody derivatives wherein the antibody or antibody fragment thereof of the present invention which specifically recognizes the extracellular domain of erbB3 and inhibits EGF-like ligand-dependent phosphorylation of erbB3, is conjugated to a radioisotope, a low-molecular weight drug, a high-molecular weight drug, a protein, or a pharmaceutical antibody in a chemical manner or in a manner of genetic engineering.

The antibody derivatives of the present invention can be produced in the following manner. That is, by chemical techniques [Introduction to antibody engineering, Chijinshokan Co., Ltd. (1994)], a radioisotope, a low-molecular weight drug, a high-molecular weight drug, an immunoactivator, a protein, or an antibody medication is bound to the N- or C-terminal of the H-chain or L-chain of the antibody or the antibody fragment thereof of the present invention which specifically recognizes the extracellular domain of erbB3 and inhibits EGF-like ligand-dependent phosphorylation of erbB3, to an appropriate substituent or side chain of the antibody or the antibody fragment thereof, to a sugar chain of the antibody or the antibody fragment thereof, or the like, whereby the antibody derivatives can be produced.

The antibody derivatives of the present invention can also be produced in a technique of genetic engineering in which a DNA encoding the antibody or the antibody fragment thereof of the present invention which specifically recognizes the extracellular domain of erbB3 and inhibits EGF-like ligand-dependent phosphorylation of erbB3 is fused to a DNA encoding a protein or a pharmaceutical antibody desired to be bound, the fused DNA is inserted into an expression vector, and the expression vector is introduced to an appropriate host cell to express the derivatives.

Examples of the radioisotope include $^{111}$In, $^{131}$I, $^{125}$I, $^{90}$Y, $^{64}$Cu, $^{99}$Tc, $^{77}$Lu, $^{211}$At, and the like. The radioisotope can be directly bound to the antibody by a chloramine-T method and the like. In addition, a substance chelating the radioisotope may be bound to the antibody. Examples of the chelating agent include 1-isocyanatobenzyl-3-methyldiethylenetriamine pentaacetic acid (MX-DTPA) and the like.

Examples of the low-molecular weight drug include anti-cancer agents [Clinical oncology, Cancer & Chemotherapy (1996)] such as an alkylation agent, a nitrosourea agent, a metabolic antagonist, an antibiotic, plant alkaloids, a topoisomerase inhibitor, a hormone therapy agent, a hormone antagonist, an aromatase inhibitor, a P-glycoprotein inhibitor, platinum complex derivatives, an M-phase inhibitor, and a kinase inhibitor; steroid agents such as hydrocortisone and prednisone; non-steroid agents such as aspirin and indomethacin; immunoregulators such as gold thiomalate and penicillamine; immunosuppressants such as cyclophosphamide and azathioprine; anti-inflammatory agents [Inflammation and anti-inflammatory therapy, Ishiyaku Pub, Inc. (1982)] such as an anti-histamines like chlorpheniramine maleate and clemastine, and the like.

Examples of the anti-cancer agent include amifostine (Ethyol), cisplatin, darcarbazine (DTIC), dactinomycin, mechlorethamine (nitrogen mustard), streptozocin, cyclophosphamide, ifosfamide, carmustine (BCNU), lomustine (CCNU), doxorubicin (adriamycin), epirubicin, gemcitabine (Gemzar), daunorubicin, procarbazine, mitomycin, citarabine, etoposide, methotrexate, 5-fluorouracil, fluorouracil, vinblastine, vincristine, bleomycin, daunomycin, peplomycin, estramustine, paclitaxel (Taxol), docetaxel (Texotere), aldesleukin, asparaginase, busulfan, carboplatin, oxaliplatin, nedaplatin, cladribine, camptothecin, 10-hydroxy-7-ethyl-camptothecin (SN38), floxuridine, fludarabine, hydroxyurea, idarubicin, mesna, irinotecan (CPT-11), nogitecan, mitoxantrone, topotecan, leuprolide, megestrol, melphalan, mercaptopurine, hydroxycarbamide, plicamycin, mitotane, pegasparagase, pentostatin, pipobroman, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacytidine, UFT, oxaliplatin, gefitinib (Iressa), imatinib (STI571), erlotinib, an FMS-like tyrosine kinase 3 (Flt3) inhibitor, a vascular endothelial growth factor receptor (VEGFR) inhibitor, a fibroblast growth factor receptor (FGFR) inhibitor, an epidermal growth factor receptor (EGFR) inhibitor such as Iressa or Tarceva, radicicol, 17-allylamino-17-dimethoxygeldanamycin, amsacrine, all-trans-retinoic acid, thalidomide, lenalidomide, anastrozole, fadrozole, letrozole, exemestane, gold thiomalate, D-penicillamine, bucillamine, azathioprine, mizoribine, cyclosporin, rapamycin, hydrocortisone, bexarotene (Targretin), dexamethasone, progestins, estrogens, anastrozole (Arimidex), leuplin, aspirin, indomethacin, celecoxib, azathioprine, penicillamine, chlorophenylamine maleate, chlorophenylamine, clemastine, tretinoin, bexarotene, arsenic, bortezomib, allopurinol, calicheamicin, ibritumomab tiuxetan, Targretin, ozagamicin, clarithromycin, leucovorin, ketoconazole, aminoglutethimide, suramin, maytansinoid or derivatives thereof, and the like.

Examples of the method of binding the low-molecular weight drug to an antibody include a method of binding amino groups of the drug and the antibody to each other via glutaraldehyde, a method of binding amino groups of a drug to carboxyl groups of an antibody via water-soluble carbodiimide, and the like.

Examples of the high-molecular weight drug include polyethylene glycol (hereinbelow, described as "PEG"), albumin, dextran, polyoxyethylene, a styrene-maleic acid copolymer, polyvinyl pyrrolidone, a pyran copolymer, hydroxypropyl methacrylamide, and the like.

By binding these high-molecular weight compounds to an antibody or an antibody fragment thereof, it is expected that effects such as (1) improvement of stability with respect to various factors such as chemical, physical, and biological factors, (2) marked extension of half-life in blood, and (3) suppression of loss of immunogenicity or anti-antibody production will be obtained ["Bioconjugate Drugs", Hirokawa Shoten Ltd. (1993)].

Examples of the method of binding PEG to an antibody include a method of binding the antibody with a PEGylation modification reagent, and the like ["Bioconjugate Drugs", Hirokawa Shoten Ltd. (1993)]. Examples of the PEGylation modification reagent include a modifier (JP-A-61-178926) which modifies lysine to a E-amino group, a modifier (JP-A-56-23587) which modifies aspartic acid or glutamic acid into a carboxyl group, a modifier (JP-A-2-117920) which modifies arginine into a guanidino group, and the like.

The immunoactivator may be a natural substance known as an immunoadjuvant, and specific examples thereof include drugs boost immunity such as $\beta(1\rightarrow3)$glucan (lentinan or sizofuran), $\alpha$-galactosylceramide (KRN 7000), and the like.

Examples of the protein include cytokines or growth factors which activate immunocompetent cells such as NK cells, macrophages, and neutrophils, toxic proteins, and the like.

Examples of the cytokines and growth factors include interferon (hereinbelow, described as "IFN")-$\alpha$, IFN-$\beta$, IFN-$\gamma$, interleukin (hereinbelow, described as "IL")-2, IL-12, IL-15, IL-18, IL-21, IL-23, a granulocyte colony-stimulating factor (G-CSF), a granulocyte/macrophage colony-stimulating factor (GM-CSF), a macrophage colony-stimulating factor (M-CSF), and the like. Examples of the toxic proteins include lysine, diphtheria toxin, ONTAK, and the like. The toxic proteins also include protein toxin which is obtained by introducing mutation to a protein for adjusting toxicity.

Examples of the pharmaceutical antibody include antibodies against an antigen in which apoptosis is induced due to binding of an antibody, an antigen involved in formation of pathological conditions of tumors, an antigen regulating immune function, and an antigen involved in angiogenesis in a lesional site.

Examples of the antigen in which apoptosis is induced due to binding of an antibody include a Cluster of Differentiation (hereinbelow, described as "DS") 19, CD20, CD21, CD22, CD23, CD24, CD37, CD53, CD72, CD73, CD74, CDw75, CDw76, CD77, CDw78, CD79a, CD79b, CD80(B7.1), CD81, CD82, CD83, CDw84, CD85, CD86(B7.2), human leukocyte antigen (HLA)-Class II, Epidermal Growth Factor Receptor (EGFR), and the like.

Examples of the antigen involved in formation of pathological conditions of tumors and the antigen regulating immune function include CD4, CD40, a CD40 ligand, B7 family molecules (CD80, CD86, CD274, B7-DC, B7-H2, B7-H3, and B7-H4), ligands of B7 family molecules (CD28, CTLA-4, ICOS, PD-1, and BTLA), OX-40, lignads of OX-40, CD137, tumor necrosis factor (TNF) receptor family molecules (DR4, DR5, TNFR1, and TNFR2), TNF-related apoptosis-inducing ligand receptor (TRAIL) family molecules, family of TRAIL family molecule receptor (TRAIL-R1, TRAIL-R2, TRAIL-R3, and TRAIL-R4), receptor activator of nuclear factor kappa B ligand (RANK), a RANK ligand, CD25, folate receptors, cytokines (IL-1α, IL-1β, IL-4, IL-5, IL-6, IL-10, IL-13, transforming growth factor (TGF) β, TNF α, and the like), receptors of these cytokines, chemokines (SLC, ELC, I-309, TARC, MDC, CTACK, and the like), and receptors of these chemokines Examples of the antigen to an antibody inhibiting angiogenesis of a lesional site include vascular endothelial growth factor (VEGF), angiopoietin, a fibroblast growth factor (FGF), EGF, a hepatocyte growth factor (HGF), a platelet-derived growth factor (PDGF), an insulin-like growth factor (IGF), erythropoietin (EPO), TGFβ, IL-8, ephrin, SDF-1, receptors thereof, and the like.

The fusion antibody fused with a protein or with a pharmaceutical antibody can be produced in the following manner. That is, cDNA encoding a monoclonal antibody or the antibody fragment is ligated to cDNA encoding a protein to construct a DNA encoding a fusion antibody, the DNA is inserted into an expression vector for prokaryotes or eukaryotes, and then the expression vector is introduced into prokaryotes or eukaryotes to express the fusion antibody.

When the antibody derivatives described above are used for a detection method and quantitation method or used as a reagent for detection, quantitation, or diagnosis, examples of drugs bound to the monoclonal antibody or the antibody fragment thereof of the present invention which specifically recognizes the natural three-dimensional structure in the extracellular domain of erbB3 and binds to the extracellular domain include labeling substances used for general immunological detection and measurement methods.

Examples of the labeling substance include enzymes such as alkaline phosphatase, peroxidase, and luciferase; luminous substances such as acridinium ester and lophine; fluorescent substances such as fluorescein isothiocyanate (FITC) and tetramethyl rhodamine isothiocyanate (RITC); and the like.

In the present invention, examples of a tumor, a malignant tumor, and cancer include at least one kind selected from colon cancer, colorectal cancer, lung cancer, breast cancer, brain tumor, melanoma, renal cell carcinoma, leukemia, lymphoma, T cell lymphoma, gastric cancer, pancreatic cancer, cervical cancer, endometrial cancer, ovarian cancer, esophageal cancer, hepatoma, head and neck squamous cell carcinoma, skin cancer, urinary tract cancer, prostate cancer, choriocarcinoma, pharyngeal cancer, laryngeal cancer, pleural tumor, arrhenoblastoma, endometrial hyperplasia, endometriosis, embryoma, fibrosarcoma, Kaposi's sarcoma, hemangioma, cavernous hemangioma, angioblastoma, retinoblastoma, astrocytoma, neurofibromatosis, oligodendrogligoma, medulloblastoma, neuroblastoma, neuroglioma, rhabdomyosarcoma, glioblastoma, osteosarcoma, leiomyosarcoma, thyroid sarcoma, and Wilms tumor.

Hereinbelow, the method of preparing the antibody of the present invention and the erbB3 measurement method, diagnosis method, and treatment method using the antibody will be described in detail.

1. Method of Preparing Antibody

In the present invention, production of a monoclonal antibody comprises the following steps.

That is, the steps are (1) purifying biopolymers and/or preparing cells overexpressing an antigen protein on the surface thereof so as to obtain an immunogen to be used, (2) immunizing an animal by injection of the antigen, subsequently testing antibody titer by collecting blood so as to determine time to extract spleen or the like, and then preparing antibody-producing cells, (3) preparing myeloma cells (hereinbelow, referred to as "myeloma"), (4) performing cell fusion to fuse the antibody-producing cell with myeloma, (5) selecting a hybridoma group producing the target antibody, (6) dividing into single cell clone (cloning), (7) culturing a hybridoma for producing monoclonal antibodies in large quantities or raising the hybridoma-grafted animal in some cases, (8) investigating bioactivity and recognition specificity of the monoclonal antibodies produced in this manner or testing characteristics of the antibodies as a labeling reagent, and the like.

Hereinbelow, the method of preparing the anti-erbB3 antibody of the present invention will be described in detail according to the above steps. However, the antibody preparation method is not limited thereto, and for example, antibody-producing cells and myelomas other than splenocytes can also be used. It is also possible to use antibodies derived from serum of an antibody-producing transgenic animal.

(1) Purification of Antigen

The erbB3 to be an antigen or cells expressing erbB3 can be obtained by introducing an expression vector comprising cDNA encoding full length or partial length of erbB3 into *Escherichia coli*, yeast, insect cells, animal cells, or the like. Moreover, they can also be obtained by purifying erbB3 from various human tumor culture cells, human tissues, and the like; expressing a large amount of erbB3. The tumor culture cells, tissues, or the like can also be used as an antigen as they are. In addition, a synthetic peptide comprising the partial sequence of erbB3 can be prepared by a chemical synthesis method such as an Fmoc method or a tBOC method so as to be used as an antigen.

The erbB3 used in the present invention can be produced by expressing DNA encoding the erbB3 in host cells by, for example, the following method by using methods disclosed in Molecular Cloning, A Laboratory Manual, Second Edition, Cold Spring Harbor Laboratory Press (1989), Current Protocols In Molecular Biology, John Wiley & Sons (1987-1999), and the like.

Full length cDNA encoding erbB3 is inserted into the downstream of a promoter of an appropriate expression vector, thereby preparing a recombinant vector. Instead of the full length cDNA, a DNA fragment having an appropriate length which is prepared based on full length cDNA and encodes a partial polypeptide may be used. Subsequently, the obtained recombinant vector is introduced into host cells suitable for the expression vector, whereby an erbB3-producing transformant can be obtained.

Any type of vector can be used as the expression vector so long as it can be replicated autonomously in the host cell used or incorporated into chromosomes and comprises an appropriate promoter in a position where DNA encoding erbB3 can be transcribed.

Any type of cell such as microorganism like *Escherichia coli* which belongs to genus *Escherichia*, yeast, insect cells, and animal cells can be used as the host cell so long as it can express the target genes.

When a prokaryote such as *Escherichia coli* is used as a host cell, the recombinant vector is preferably a vector which enables autonomous replication in the prokaryote and comprises a promoter, a ribosome binding sequence, DNA encoding erbB3, and a transcription termination sequence. The transcription termination sequence is not definitely necessary for the recombinant vector, but it is preferable that the transcription termination sequence be arranged right after the structural gene. In addition, the recombinant vector may comprise a gene controlling the promoter.

As the recombinant vector, it is preferable to use a plasmid in which the distance between Shine-Dalgarno sequence as the ribosome binding sequence and a start codon is appropriately (for example 6 to 18 nucleotides) adjusted.

In the nucleotide sequence of a DNA encoding erbB3, nucleotide substitution can be carried out so as to create a codon optimal for expression in the host, and by doing this, a production rate of the desired erbB3 can be increased.

Any type of vector can be used as the expression vector as long as it can function in the host cell used, and examples thereof include pBTrp2, pBTac1, and pBTac2 (all manufactured by Roche Diagnostics Corporation), pKK233-2 (manufactured by Amersham Pharmaca Biotech), pSE280 (manufactured by Invitrogen), pGEMEX-1 (manufactured by Promega Corporation), pQE-8 (manufactured by QIAGEN), pKYP10 (JP-A-58-110600), pKYP200 [Agricultural Biological Chemistry, 48, 669 (1984)], pLSA1 [Agric. Biol. Chem., 53, 277 (1989)], pGEL1(Proc. Natl. Acad. Sci. USA, 82, 4306 (1985)), pBluescript II SK(−) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM BP-400), JP-A-60-221091], pGKA2 [prepared from *Escherichia coli* IGKA2 (FERM BP-6798), JP-A-60-221091], pTerm2 (Specification of U.S. Pat. No. 4,686,191, Specification of U.S. Pat. No. 4,939,094, Specification of U.S. Pat. No. 5,160,735), pSupex, pUB110, pTP5, pC194, and pEG400 [J. Bacteriol., 172, 2392 (1990)], pGEX (manufactured by Amersham Pharmacia Biotech), pET system (manufactured by Novagen), pME18SFL3, and the like.

Any type of promoter can be used as long as it can function in the host cell used, and examples thereof include promoters derived from *Escherichia coli* or phage, such as a tip promoter (Ptrp), a lac promoter, a PL promoter, a PR promoter, and a T7 promoter. It is also possible to use promoters obtained by artificially changing design, such as a tandem promoter in which two Ptrps are arranged in series, a tac promoter, a lac T7 promoter, and a letI promoter.

Examples of the host cell include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* DH5α, and the like.

Any method can be used as the method of introducing the recombinant vector into the host cell as long as the method can introduce a DNA into a host cell used. Examples of the method include a method of using calcium ions [Proc. Natl. Acad. Sci. USA, 69, 2110 (1972), Gene, 17, 107 (1982), Molecular & General Genetics, 168, 111 (1979)].

When an animal cell is used as a host, any type vector can be used as the expression vector as long as it can function in the animal cell. Examples of the expression vector include pcDNAI and pcDM8 (manufactured by Funakoshi Corporation), pAGE107 [JP-A-3-22979; Cytotechnology, 3, 133 (1990)], pAS3-3 (JP-A-2-227075), pCDM8 [Nature, 329, 840 (1987)], pcDNAI/Amp (manufactured by Invitrogen), pcDNA3.1 (manufactured by Invitrogen), pREP4 (manufactured by Invitrogen), pAGE103 [J. Biochemistry, 101, 1307 (1987)], pAGE210, pME18SFL3, pKANTEX93 (WO 97/10354), and the like.

Any type of promoter can be used as long as it can function in the animal cell, and examples thereof include a promoter of immediate early (IE) gene of cytomegalovirus (CMV), an early promoter of SV40, a promoter of a retrovirus, a methalothionein promoter, a heat shock promoter, an SRα promoter, and a promoter or enhancer of Moloney mouse leukemia virus. An enhancer of IE gene of human CMV may be used in combination with a promoter.

Examples of the host cell include Namalwa cell as a human cell, COS cell as a cell of a monkey, CHO cell as a cell of a Chinese hamster, HBT5637 (JP-A-63-000299), and the like.

Any method can be used as the method of introducing the recombinant vector into the host cell so long as the method introduces a DNA into animal cells. Examples of the method include electroporation [Cytotechnology, 3, 133 (1990)], a calcium phosphate method (JP-A-2-227075), lipofection [Proc. Natl. Acad. Sci. USA, 84, 7413 (1987)], and the like.

A transformant derived from a microorganism or an animal cell obtained as above and integrated the recombinant vector in which the DNA encoding erbB3 is inserted is cultured in a medium so as to produce and accumulate erbB3 in the culture, and the erbB3 is collected from the culture, whereby the erbB3 can be produced. The method of culturing the transformant in a medium can be implemented according to a method generally used for culturing a host.

When erbB3 is expressed in eukaryote-derived cells, it is possible to obtain erbB3 supplemented with sugar or a sugar chain. When a microorganism transformed with a recombinant vector using an inductive promoter is cultured, an inducer may optionally be added to the medium. For example, when a microorganism transformed with a recombinant vector using a lac promoter is cultured, isopropyl-β-D-thiogalactopyranoside or the like may be added to the medium, and when a microorganism transformed with a recombinant vector using a trp promoter is cultured, indole acrylic acid or the like may be added to the medium.

Examples of the medium for culturing the transformant obtained from animal cells as a host include the generally used RPMI1640 medium [The Journal of the American Medical Association, 199, 519 (1967)], Eagle's MEM [Science, 122, 501 (1952)], Dulbecoo's modified MEM [Virology, 8, 396 (1959)], a 199 medium [Proc. Soc. Exp. Biol. Med., 73, 1 (1950)], Iscove's Modified Dulbecco's Medium (IMDM), media supplemented with fetal bovine serum (FBS) or the like to the above media, and the like. Culturing is performed for 1 to 7 days under conditions of pH of 6 to 8, a temperature of 30° C. to 40° C. in the presence of 5% $CO_2$ in general. During culturing, antibiotic such as kanamycin or penicillin may be optionally supplemented.

Examples of the method of expressing the gene encoding the erbB3 include methods such as secretory production and fusion protein expression [Molecular Cloning, A Laboratory Manual, Second Edition, Cold Spring Harbor Laboratory Press (1989)], in addition to the direct expression method.

Examples of the erbB3 production method include a method of producing erbB3 intracellulaly, method of causing the host cell to secrete erbB3 extracellularly, and a method of producing erbB3 on the outer membrane of the host cell. By varying the host cell used and the structure of the erbB3 produced, it is possible to select an appropriate method.

For example, DNA is prepared which is obtained by ligating DNA encoding the amino acid sequence of the extracellular domain to a DNA encoding the Fc region of an antibody, DNA encoding glutathione S-transferase (GST), a DNA encoding FLAG-tag, DNA encoding a histidine tag, or the like, followed by expression and purification, whereby an antigen fusion protein can be prepared.

Specific examples of the antigen fusion protein include an Fc fusion protein wherein the extracellular domain of the erbB3 is fused to the Fc region of human IgG (hereinbelow, described as "erbB3-hFc"), and a fusion protein wherein the extracellular domain of erbB3 is fused with glutathione S-transferase (GST) (hereinbelow, described as "erbB3-GST").

When erbB3 is produced in a host cell or on the outer membrane of a host cell, it is possible to cause the host cell to actively secrete the erbB3 extracellularly by using the method of Paulson et al [J. Biol. Chem., 264, 17619 (1989)], the method of Lowe et al. [Proc. Natl. Acad. Sci. USA, 86, 8227 (1989), Genes Develop., 4, 1288 (1990)], and the methods disclosed in JP-A-05-3369363, WO 94/23021, and the like.

The amount of erbB3 produced can be increased using a gene amplification system (JP-A-2-227075) which uses a dihydrofolate reductase gene and the like.

The obtained erbB3 can be isolated and purified in the following manner, for example.

When erbB3 is intracellularly expressed as soluble protein, the cells are recovered by centrifugation after culturing is completed. Thereafter, the cells are suspended in an aqueous buffer and destroyed using an ultrasonicator, French press, Manton-Gaulin homogenizer, a dynomill, or the like, thereby obtaining a cell lysate. The cell lysate is centrifuged to obtain supernatant, and from this supernatant, a purified preparation can be obtained by general protein isolation and purification techniques such as solvent extraction, salting-out using ammonium sulfate or the like, desalting, precipitation using an organic solvent, anion exchange chromatography using a resin such as diethylaminoethyl (DEAE) sepharose or DIAION HPA-75 (manufactured by Mitsubishi Chemical Corporation), cation exchange chromatography using a resin such as S-Sepharose FF (manufactured by Amersham Pharmacia Biotech), hydrophobic chromatography using a resin such as butyl-sepharose or phenyl-sepharose, gel filtration using a molecular sieve, affinity chromatography, chromatofocusing, electrophoresis such as isoelectric focusing, and the like which may be used alone or used in combination.

When erbB3 is expressed intracellularly as an inclusion body, the cells are recovered in the same manner as described above and destroyed, followed by centrifugation, thereby recovering the inclusion body of erbB3 as a sedimentation fraction. The recovered inclusion body of erbB3 is solubilized using a protein denaturant. The solubilized liquid is diluted or dialyzed to restore the normal three-dimensional structure of erbB3, followed by the same isolation and purification as described above, whereby a purified preparation of polypeptide can be obtained.

When erbB3 or the derivative such as a glycosylated product thereof is secreted extracellularly, erbB3 or the derivative such as a glycosylated product thereof can be recovered from the culture supernatant. The culture is treated with a technique such as centrifugation as described above so as to obtain a soluble fraction, and then a purified preparation can be obtained from the soluble fraction by using the same isolation and purification as described above.

erbB3 used in the present invention can also be produced by a chemical synthesis method such as the Fmoc method or tBoc method. In addition, since the primary structure of erbB3 is already known (Kraus, M. H. et al., Proc. Natl. Acad. Sci. 86, 9193-9197, 1989), the peptide can be prepared by methods known to a person in the related art. The erbB3 can be chemically synthesized using a peptide synthesizer manufactured by Advanced ChemTech, PerkinElmer Inc, Amersham Pharmacia Biotech, Protein Technology Instrument, SynthecellNega Biomolecules Corporation, Perceptive, Shimadzu Corporation, or the like.

(2) Step of Preparing Antibody-Producing Cell

A mouse, rat, hamster, or the like which is 3 to 20-week-old is immunized with the antigen obtained in the section (1), and antibody-producing cells in the spleen, lymph node, or peripheral blood of the animal are collected. As the animal, a transgenic mouse having an ability of producing antibodies derived from a human being, which is disclosed in the document of Tomizuka et al. (Tomizuka et al., Proc. Natl. Acad. Sci. USA., Vol 97:722, 2000) can be used. Alternatively, in order to enhance immunogenicity, an erbB3 conditional knockout mouse can be used as an animal to be immunized.

The immunization is performed by administering the antigen together with an appropriate adjuvant such as a complete Freund's adjuvant or a combination of aluminum hydroxide with pertussis vaccine. The immunogen administration at the time of mouse immunization can be performed by any method such as subcutaneous injection, intraperitoneal injection, intravenous injection, intradermal injection, intramuscular injection, or plantar injection, but intraperitoneal injection, plantar injection, or intravenous injection is preferable. When the antigen is a partial peptide, a conjugate is prepared with a carrier protein such as bovine serum albumin (BSA) or Keyhole Limpet Hemocyanin (KLH) so as to be used as an immunogen.

The antigen is administered 5 to 10 times every one week or every two weeks after the first administration. Three to seven days after each administration, blood is collected from the venous plexus of fundus, and the antibody titer of the serum is measured using enzyme immunoassay [Antibodies—A Laboratory Manual, Cold Spring Harbor Laboratory (1988)] or the like. If an animal showing a sufficient antibody titer in its serum against the antigen used for immunization is used as a source of antibody-producing cells for fusion, it is possible to further enhance the effect of the subsequent operations.

Three to seven days after the final administration of the antigen, a tissue including antibody-producing cells, such as spleen, is resected from the immunized animal to collect the antibody-producing cells. The antibody-producing cells are plasmocytes and lymphocytes which are precursor cells of the plasmocytes. These cells may be obtained from any site of an individual. Generally, they can be obtained from spleen, lymph nodes, bone marrow, tonsil, peripheral blood, or from an appropriate combination thereof, but splenocytes are most commonly used. When splenocytes are used, the spleen is minced and loosened and then subjected to centrifugation, and erythrocytes are removed, thereby obtaining antibody-producing cells for fusion.

(3) Step of Preparing Myeloma

As myelomas, it is possible to use cells not having an ability of producing autoantibodies and derived from a mammal such as a mouse, a rat, a guinea pig, a hamster, a rabbit, or a human being. In general, for example, an established cell line obtained from a mouse is used as a myeloma cell, and examples thereof include a 8-azaguanine-resistant mouse (derived from BALB/c) myeloma cell line P3-X63Ag8-U1 (P3-U1) [Current Topics in Microbiology and Immunology, 18, 1 (1978)], P3-NS1/1-Ag41 (NS-1) [European J. Immunology, 6, 511 (1976)], SP2/0-Ag14 (SP-2) [Nature, 276, 269 (1978)], P3-X63-Ag8653 (653) [J. Immunology, 123, 1548 (1979)], P3-X63-Ag8 (X63) [Nature, 256, 495 (1975)], and the like.

These cells lines are subcultured in an appropriate medium such as a 8-azaguanine medium [a medium obtained by adding 8-azaguanine to an RPMI-1640 medium supplemented with glutamine, 2-mercaptoethanol, gentamycin, and fetal calf serum (hereinbelow, referred to as "FCS")], the Iscove's Modified Dulbecco's Medium (hereinbelow, referred to as "IMDM"), or the Dulbecco's Modified Eagle Medium (hereinbelow, referred to as "DMEM"). The cells are subcultured 3 to 4 days before cell fusion in a normal medium (for example, a DMEM containing 10% FCS) to secure cells in number of $2 \times 10^7$ or more on the day of fusion.

(4) Cell Fusion

The antibody-producing cells for fusion obtained in the section (2) and the myeloma cells obtained in the section (3) are sufficiently washed with a Minimum Essential Medium (MEM) or PBS (1.83 g of disodium phosphate, 0.21 g of potassium phosphate, 7.65 g of salt, 1 L of distilled water, pH 7.2) and mixed with each other so as to yield cell number of antibody-producing cells for fusion:myeloma cells=5:1 to 10:1, followed by centrifugation, and then the supernatant is removed.

The precipitated cell group is sufficiently loosened, and then a mixture of polyethylene glycol-1000 (PEG-1000), MEM, and dimethylsulfoxide is added to the cell under stirring at 37° C. In addition, 1 mL to 2 mL of MEM is added thereto several time every one or two minutes, and then MEM is added thereto yield a total amount of 50 mL. After centrifugation, the supernatant is removed. The precipitated cell group is gently loosened and then gently suspended in a normal medium (HAT medium) formed by adding hypoxanthine, thymidine, and aminopterin to the antibody-producing cells for fusion. This suspension is cultured for 7 to 14 days in a 5% $CO_2$ incubator at 37° C.

Cell fusion can also be performed in the following method. The splenocytes and myelomas are sufficiently washed with a serum-free medium (for example, DMEM) or with phosphate buffer saline (hereinbelow, referred to as a "phosphate buffer"), and mixed with each other such that a cell number ratio between the splenocytes and the myelomas becomes about 5:1 to 10:1, followed by centrifugation.

The supernatant is removed, the precipitated cell group is sufficiently loosened, and then the cells are added dropwise to a serum-free medium containing 1 mL of 50% (w/v) polyethylene glycol (molecular weight of 1000 to 4000) under stirring. Thereafter, 10 mL of a serum-free medium is slowly added thereto, followed by centrifugation.

The supernatant is discarded again, and the precipitated cells are suspended in a HAT medium containing an appropriate amount of HAT solution and human interleukin-2 (hereinbelow, referred to as "IL-2") and then dispensed to the respective wells of a culture plate (hereinbelow, referred to as a "plate"), followed by culture for about 2 weeks at 37° C. in the presence of 5% $CO_2$. During culturing, a HAT medium is supplemented appropriately.

(5) Selection of Hybridoma Group

When the myeloma cells described above are a 8-azaguanine-resistant line, that is, a hypoxanthine/guanine/phosphoribosyltransferase (HGPRT)-deficient line, the myeloma cells not fused and the fusion cells of the myeloma cells cannot survive in the HAT-containing medium. On the other hand, the fusion cells of the antibody-producing cells each other and the hybridoma of the antibody-producing cells and the myeloma cells can survive, but life of the fusion cells of the antibody-producing cells is limited. Accordingly, if these cells are continuously cultured in the HAT-containing medium, only the hybridoma of the antibody-producing cells and the myeloma cells can survive, and as a result, it is possible to select the hybridoma.

The medium of the hybridoma grown in a colony shape is replaced with a medium (hereinbelow, referred to as an "HT medium") obtained by removing aminopterin from the HAT medium. Thereafter, a portion of the supernatant is collected, and then an antibody-producing hybridoma can be selected using the antibody titer measurement method described later.

Examples of the method of measuring antibody titer include various known techniques such as radioimmunoassay (hereinbelow, referred to as an "RIA"), enzyme-linked immunosorbent assay (hereinbelow, referred to as an "ELISA"), a fluorescent antibody method, and passive hemagglutination. Among these, in view of detection sensitivity, rapidity, accuracy, possibility of operation automation, and the like, the RIA or ELISA is preferable.

The hybridoma which is confirmed to produce specific antibodies by the antibody titer measurement is transferred to another plate and cloned. Examples of the cloning method include limiting dilution method in which the hybridoma is cultured by being diluted such that one hybridoma is contained in each well of the plate, a soft agar method in which the hybridoma is cultured in a soft agar medium to recover the colony, a method of taking out cells one by one by using a micromanipulator and culturing the cells, and "sorter cloning" in which a single cell is separated by a cell sorter, and the like. Limiting dilution method is widely used due to its simplicity.

Cloning is repeated 2 to 4 times by, for example, limiting dilution for the wells in which the antibody titer is confirmed, and a hybridoma in which the antibody titer is stably confirmed is selected as an anti-human erbB monoclonal antibody-producing hybridoma line.

(6) Preparation of Monoclonal Antibody

The monoclonal antibody-producing hybridoma obtained in the section (5) is intraperitoneally injected to 8- to 10-week-old mice or nude mice treated with pristane [0.5 mL of 2,6,10,14-tetramethylpentadecane (pristane) is administered intraperitoneally, and the animals are raised for 2 weeks]. The hybridoma develops ascites carcinoma in 10 to 21 days.

The ascite is collected from the mice and centrifuged to remove solid contents, followed by salting-out using 40% to 50% ammonium sulfate, and purified by precipitation using caprylic acid, a DEAE-sepharose column, a Protein A column, or a gel filtration column, whereby an IgG or IgM fraction is collected as a purified monoclonal antibody. In addition, by causing the hybridoma to grow inside the abdominal cavity of the same type of mice (for example, BALB/c) or Nu/Nu mice, rats, guinea pigs, hamsters, and rabbits, it is possible to obtain the ascite containing a large amount of the anti-erbB3 antibody of the present invention.

The monoclonal-antibody producing hybridoma obtained in the section (5) is cultured in RPMI1640 medium or the like supplemented with 10% FBS, followed by centrifugation to remove the supernatant. The cells are suspended in a GIT medium, Hybridoma SFM supplemented with 5% Daigo's GF21, or the like, and cultured for 3 to 7 days by flask culturing, spinner culturing, bag culturing, or the like.

The obtained cell suspension is centrifuged, and purification is performed from the obtained supernatant by using Protein A column or protein G column to collect thereby an IgG fraction, whereby it is possible to obtain the purified monoclonal antibody. As a simple purification method, it is also possible to use a commercially available monoclonal antibody purification kit (for example, MAbTrap GII kit; manufactured by Amersham Pharmacia Biotech).

The subclass of antibody is determined by enzyme immunoassay using a subclass typing kit. Quantitation of the protein can be carried out by the Lowry method and a method of calculating the protein amount by an absorbance at 280 nm [1.4 ($OD_{280}$)=immunoglobulin 1 mg/mL].

(7) Binding Assay of Anti-erbB3 Monoclonal Antibody

Binding activity of the anti-erbB3 monoclonal antibody of the present invention can be confirmed by a binding assay system such as the Ouchterlony method, ELISA, RIA, a flow cytometry (FCM), or a surface plasmon resonance (SPR) method. Though simple, the Ouchterlony method requires concentration operation when antibody concentration is low.

When the ELISA or RIA is used, the culture supernatant is bound with an antigen-adsorbed solid phase as is, and an antibody corresponding to various immunoglobulin isotypes and subclasses is used as a second antibody, whereby the isotype and subclass of the antibody can be identified.

The purified or partially purified recombinant human erbB3 is adsorbed onto a solid phase surface of a 96-well plate for ELISA or the like, and a solid phase surface onto which an antigen is not adsorbed is blocked with a protein irrelevant with an antigen, such as bovine serum albumin (hereinbelow, described as "BSA").

The ELISA plate is washed with phosphate buffer saline (hereinbelow, described as "PBS") containing 0.05% Tween 20 (hereinbelow, abbreviated to Tween-PBS) or the like and then bound with a serially diluted first antibody (for example, mouse serum, culture supernatant, or the like), thereby binding the antibody to the antigen immobilized onto the plate.

Thereafter, as a second antibody, an anti-immunoglobulin antibody labeled with biotin, an enzyme (horse radish peroxidase; HRP, alkaline phosphatase; ALP, or the like), a chemiluminescent substance, a radioisotope, or the like is dispensed to the plate, thereby reacting the second antibody with the first antibody having bound to the plate. After the plate is sufficiently washed with Tween-PBS, a reaction caused by the labeling substance of the second antibody is performed, thereby selecting a monoclonal antibody binding specifically with the immunogen.

Binding activity of a target antibody with respect to an antigen-expressing cell can be measured by the FCM [Cancer Immunol. Immunother., 36, 373 (1993)]. If a target antibody binds to a membrane protein expressed on a cell membrane, this can be mentioned that the target antibody is an antibody which recognizes the three-dimensional structure of a naturally occurring antigen.

Examples of the SPR include kinetics analysis using Biacore®. For example, by using Biacore® T100, kinetics in binding of an antigen to a subject substance is measured, and the resultant thereof is analyzed by analysis software attached to the instrument.

After the anti-mouse IgG antibody is immobilized onto a sensor chip CM5 by an amine coupling method, a subject substance such as hybridoma culture supernatant or a purified monoclonal antibody is allowed to flow such that an appropriate amount of the substance binds to the antibody, and then an antigen of different levels of known concentration is allowed to flow, thereby measuring binding and dissociation. The kinetics analysis is performed on the obtained data by using software attached to the instrument by a 1:1 binding model, thereby obtaining various parameters.

Alternatively, the human erbB3 protein is immobilized onto a sensor chip by, for example, the amine coupling method, and then a purified monoclonal antibody with different levels of known concentration is allowed to flow, thereby measuring binding and dissociation. The kinetic analysis is performed on the obtained data by using software attached to the instrument by a bivalent binding model, thereby obtaining various parameters.

The antibody which competes with the anti-erbB3 antibody of the present invention to bind to erbB3 can be obtained by adding a subject antibody to the above binding assay system and binding the antibody. That is, by screening an antibody of which the binding activity is inhibited when the subject antibody is added, it is possible to obtain an antibody which competes with the obtained antibody to bind to the extracellular domain of erbB3.

(8) Identification of Epitope of anti-erbB3 Monoclonal Antibody

In the present invention, a recognition epitope of an antibody can be identified in the following manner. For example, a partially deficient antigen, an amino-acid modified antigen obtained by modification using different heterogeneous amino acid residues, or a modified antigen obtained by modifying domains is prepared, and when the reactivity of the target antibody with respect to the deficient antigen or the amino acid-modified antigen is lowered, this clearly shows that the deficient site and the amino acid-modified site is the epitope of the target antibody. The partially deficient antigen or the amino acid-modified antigen may be obtained as a protein secreted from an appropriate host cell (*Escherichia coli*, yeast, a plant cell, a mammal cell, or the like), and it is also possible to prepare an antigen-expressing cell by expressing the antigen on the membrane of the host cell. In a case of a membrane-type antigen, it is preferable to express the antigen on the membrane of the host cell so as to express the antigen while maintaining the three-dimensional structure of the antigen. It is also possible to confirm the reactivity of the target antibody by preparing a synthetic peptide which mimics the primary structure or three-dimensional structure of the antigen. Examples of methods of preparing the synthetic peptide include a method of preparing partial peptides having various molecules by using a known peptide synthesis technique.

Regarding the anti-erbB3 antibody of the present invention, chimeric proteins obtained by combining the respective domains 1 to 4 of the extracellular domain of the human and mouse erbB3 are prepared so as to confirm the reactivity of the target antibody, whereby the epitope of the antibody can be identified.

Thereafter, various oligopeptides of the corresponding portions, mutants of the peptides, and the like are synthesized in more detail by using an oligopeptide synthesis technique known to a skilled person in the art, and the reactivity of the target antibody with respect to the peptide is confirmed to identify the epitope. As a simple method of obtaining various oligopeptides, it is possible to use a commercially available kit [for example, SPOTs kit (manufactured by Genosys Biotechnologies), a series of multipin/peptide synthesis kit (manufactured by Chiron) using a multipin synthesis method, or the like].

The antibody which binds to an epitope which is the same as the epitope which the antibody of the present invention binding to the extracellular domain of erbB3 recognizes can be obtained by identifying the epitope of the antibody obtained in the binding assay system described above; preparing a partial synthetic peptide, a synthetic peptide which has a three-dimensional structure which mimics that of the epitope, a recombinant protein, or the like of the identified epitope; and performing immunization.

For example, in a case of a membrane protein, a recombinant protein which the entire extracellular domain or a portion of the extracellular domain is fused to an appropriate tag (FLAG tag, Histidine tag, GST protein, antibody Fc region, or the like) is prepared, and the recombinant protein is immunized, whereby an epitope-specific antibody can be prepared more efficiently.

2. Preparation of Recombinant Antibody

Examples of the preparation of a recombinant antibody are roughly described in P. J. Delves, ANTIBODY PRODUCTION ESSENTIAL TECHNIQUES., 1997 WILEY, P. Shepherd and C. Dean. Monoclonal Antibodies., 2000 OXFORD UNIVERSITY PRESS, J. W. Goding., Monoclonal Antibodies: principles and practice., 1993 ACADEMIC PRESS, and the like. Hereinbelow, methods of preparing a human chimeric antibody, a humanized antibody, and a human antibody will be described.

(1) Construction of Vector for Expressing Recombinant Antibody.

A vector for expressing a recombinant antibody is an expression vector for animal cell into which a DNA encoding CH and CL of a human antibody has been inserted. This vector can be constructed by cloning DNAs encoding CH and CL of a human antibody respectively to the expression vector for animal cell.

For the C region of a human antibody, CH and CL of any human antibody can be used. For example, CH of the γ1 subclass and CL of the κ class of a human antibody are used. Though cDNA is used as the DNA encoding CH and CL of a human antibody, chromosome DNA consisting of exon and intron can also be used. Any type of expression vector can be used as the expression vector for animal cell so long as a gene encoding the C region of a human antibody can be inserted into the vector and expressed in the vector.

For examples, as the expression vector, pAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], pSE1UK1Sed1-3 [Cytotechnol., 13, 79 (1993)], INPEP4 (manufactured by Biogen-IDEC), N5KG1val (specification of U.S. Pat. No. 6,001,358), a transposon vector (WO 2010/143698), or the like is used. As a promoter or an enhancer in the expression vector for animal cell, an early promoter of SV40 [J. Biochem., 101, 1307 (1987)], Moloney mouse leukemia virus LTR [Biochem. Biophys. Res. Commun., 149, 960 (1987)], a CMV promoter (specification of U.S. Pat. No. 5,168,062), an immunoglobulin H-chain promoter [Cell, 41, 479 (1985)], and an enhancer [Cell, 33, 717 (1983)], or the like is used.

As the vector for expressing a recombinant antibody, a type (tandem type) of vector for expressing recombinant antibody in which both the H and L chains of the antibody exist on the same vector [J. Immunol. Methods, 167, 271 (1994)] is used in view of the easiness of construction of the recombinant antibody expression vector, easiness of introduction of the vector into animal cells, and balanced amount of the H and L chains of the antibody in animal cells. However, a type in which the H and L chains of an antibody exist on different vectors can also be used. As the tandem type vector for expressing a recombinant antibody, pKANTEX93 (WO 97/10354), pEE18 [Hybridoma, 17, 559 (1998)], N5KG1val (specification of U.S. Pat. No. 6,001,358), a transposon vector (WO 2010/143698), or the like is used.

(2) Obtaining cDNA Encoding V Region of Antibody Derived from Non-Human Animal and Analysis of Amino Acid Sequence.

Obtaining of cDNA encoding VH and VL of a non-human antibody and analysis of amino acid sequence can be performed as follows.

mRNA is extracted from a hybridoma cell producing a non-human antibody, thereby synthesizing cDNA. The synthesized cDNA is cloned to a vector such as a phage or a plasmid, thereby preparing a cDNA library. From the library, a recombinant phage or a recombinant plasmid having cDNA encoding VH or VL is isolated respectively by using DNA encoding the C region or V region of a mouse antibody as a probe. The full length nucleotide sequences of VH or VL of a target mouse antibody on the recombinant phage or the recombinant plasmid are determined respectively, thereby deducing the full length amino acid sequence of VH or VL respectively from the nucleotide sequence.

As the non-human animal for preparing a hybridoma cell producing a non-human antibody, a mouse, rat, hamster, rabbit, or the like is used. However, any animal can be used as long as it can produce a hybridoma cell.

For preparing total RNA from a hybridoma cell, a guanidine thiocyanate-cesium trifluoroacetate method [Methods in Enzymol., 154, 3 (1987)] or a kit such as RNA Easy® kit (manufactured by QIAGEN) is used.

For preparing mRNA from total RNA, an oligo (dT) immobilized cellulose column method [Molecular Cloning, A Laboratory Manual, Second Edition, Cold Spring Harbor Laboratory Press (1989)] or a kit such as Oligo-dT30<Super>® mRNA Purification Kit (manufactured by TAKARA BIO INC) is used. It is also possible to prepare mRNA from a hybridoma cell by using a kit such as Fast Track® mRNA Isolation Kit (manufactured by Invitrogen) or QuickPrep® mRNA Purification Kit (manufactured by Amersham Pharmacia Biotech).

For synthesizing cDNA or preparing a cDNA library, a known method [Molecular Cloning, A Laboratory Manual, Second Edition, Cold Spring Harbor Laboratory Press (1989), Current Protocols in Molecular Biology, Supplement 1, John Wiley & Sons (1987-1997)], SuperScript Plasmid System for cDNA Synthesis and Plasmid Cloning (manufactured by Invitrogen), a kit such as ZAP-cDNA Synthesis Kit (manufactured by Stratagene), or the like is used.

In preparing a cDNA library, any type of vector can be used as a vector into which cDNA synthesized using mRNA extracted from a hybridoma cell as a template is inserted, as long as the cDNA can be inserted into the vector. Examples of the vector include ZAP Express [Strategies, 5, 58 (1992)], pBluescript II SK(+) [Nucleic Acids Research, 17, 9494 (1989)], λZAPII (manufactured by Stratagene), λgt10 and λgt11 [DNA Cloning: A Practical Approach, I, 49 (1985)], Lambda BlueMid (manufactured by Clontech), λExCell, pT7T3-18U (manufactured by Amersham Pharmacia Biotech), pcD2 [Mol. Cell. Biol., 3, 280 (1983)], pUC18 [Gene, 33, 103 (1985)], and the like.

Any type of *Escherichia coli* can be used as the *Escherichia coli* into which cDNA library constructed by a phage or a plasmid vector is introduced, as long as the cDNA library can be introduced into the *Escherichia coli* and can be expressed and maintained. Examples thereof include XL-1 Blue MRF' [Strategies, 5, 81 (1992)], C600 [Genetics, 39, 440 (1954)], Y1088 and Y1090 [Science, 222, 778 (1983)], NM522 [J. Mol. Biol., 166, 1 (1983)], K802 [J. Mol. Biol., 16, 118 (1966)], JM105 [Gene, 38, 275 (1985)], and the like.

For selecting cDNA clones encoding VH or VL of a non-human antibody from the cDNA library, a colony/hybridization method using an isotope- or fluorescence-labeled probe, a plaque/hybridization method [Molecular Cloning, A Laboratory Manual, Second Edition, Cold Spring Harbor Laboratory Press (1989)], or the like is used.

In addition, the cDNA encoding VH or VL can be prepared by preparing a primer and performing Polymerase Chain Reaction [hereinbelow, described as "PCR", Molecular Cloning, A Laboratory Manual, Second Edition, Cold Spring Harbor Laboratory Press (1989), Current Protocols in Molecular Biology, Supplement 1, John Wiley & Sons (1987-1997)] by using cDNA synthesized from mRNA or the cDNA library as a template.

The selected cDNA is cleaved with an appropriate restriction enzyme or the like and then cloned into a plasmid such as pBluescript SK(–) (manufactured by Stratagene), and the nucleotide sequence of the cDNA is determined by an analysis method which is generally used for nucleotide sequence analysis. As the nucleotide sequence analysis method, for example, a reaction such as a dideoxy method [Proc. Natl. Acad. Sci. USA, 74, 5463 (1977)] is performed, and then an automatic nucleotide sequence analyzer such as A.L.F.DNA sequencer (manufactured by Amersham Pharmacia Biotech) is used.

The full amino acid sequences of VH and VL are deduced respectively from the determined nucleotide sequence and compared with the full amino acid sequences of VH and VL of known antibodies [Sequences of Proteins of Immunological Interest, US Dept. Health and Human Services (1991)], whereby whether the obtained cDNA encodes the full amino acid sequences of VH and VL of the antibody comprising a secretory signal sequence is confirmed respectively.

Regarding the full amino acid sequences of VH and VL of the antibody comprising the secretory signal sequence, by comparing these amino acid sequences with the full amino acid sequences of VH and VL of known antibodies [Sequences of Proteins of Immunological Interest, US Dept. Health and Human Services (1991)], it is possible to deduce the length of the secretory signal sequence and the N-terminal amino acid sequence and to know the subgroup to which theses sequences belong.

In addition, regarding the amino acid sequence of each CDR of VH and VL, by comparing the sequence with the amino acid sequences of VH and VL of the known antibodies [Sequences of Proteins of Immunological Interest, US Dept. Health and Human Services (1991)], it is possible to determine the amino acid sequence.

Moreover, if homology search such as the BLAST method [J. Mol. Biol., 215, 403 (1990)] is performed on any database such as SWISS-PROT or PIR-Protein by using the obtained full amino acid sequence of VH and VL, it is possible to confirm the novelty of the full amino acid sequence of VH and VL.

(3) Construction of Human Chimeric Antibody Expression Vector cDNAs encoding VH or VL of a non-human antibody are cloned respectively to the upstream of the respective genes encoding CH or CL of a human antibody of the vector for expressing recombinant antibody obtained in the section (1), whereby a human chimeric antibody expression vector can be constructed.

In order to link the 3'-terminal of cDNA encoding VH or VL of a non-human antibody to the 5'-terminal of CH or CL of a human antibody, cDNA of VH and VL is prepared which is designed such that the nucleotide sequence of the linkage site encodes appropriate amino acid and that the cDNA has an appropriate recognition sequence for a restriction enzyme. The prepared cDNAs of VH and VL are cloned respectively such that they are expressed in an appropriate form in the upstream of the respective genes encoding CH or CL of a human antibody of the vector for expressing humanized antibody obtained in the section (1), thereby constructing a human chimeric antibody expression vector.

In addition, it is also possible to amplify the cDNA encoding VH or VL of the non-human antibody respectively by PCR by using synthetic DNA which has a recognition sequence for an appropriate restriction enzyme at both ends, and to clone the cDNA to the vector for expressing recombinant antibody obtained in the section (1).

(4) Construction of cDNA Encoding V Region of Humanized Antibody cDNA encoding VH or VL of a humanized antibody can be constructed in the following manner.

Amino acid sequences of the framework region (hereinbelow, described as "FR") of VH or VL of a human antibody to which the amino acid sequence of CDR of VH or VL of a non-human antibody is grafted are selected respectively. Any type of amino acid sequence can be used as the amino acid sequence of FR selected, as long as they are derived from a human antibody.

For example, amino acid sequences of FR of human antibodies registered in a database such as Protein Data Bank, amino acid sequences common to the respective subgroups of FR of human antibodies [Sequences of Proteins of Immunological Interest, US Dept. Health and Human Services (1991)], or the like are used. In order to inhibit decrease of the binding activity of the antibody, amino acid sequences of FR highly homologous (at least 60% or higher) to the amino acid sequence of FR of VH or VL of the original antibody as far as possible are selected.

Subsequently, amino acid sequences of CDRs of the original antibody are grafted respectively to the selected amino acid sequence of FR of VH or VL of the human antibody so as to design the respective amino acid sequences of VH or VL of a humanized antibody. The designed amino acid sequences are converted into DNA sequences in consideration of the frequency of usage of codons found in the nucleotide sequence of the genes of the antibody [Sequences of Proteins of Immunological Interest, US Dept. Health and Human Services (1991)], thereby designing the respective DNA sequences encoding amino acid sequences of VH or VL of a humanized antibody.

Based on the DNA sequences designed, several strands of synthetic DNAs having a length consisting of about 100 to 150 nucleotides are synthesized to perform PCR using the DNA sequences. In this case, in view of the reaction efficiency of PCR and the length of DNA which can be synthesized, it is preferable to design 4 to 6 strands of synthetic DNAs for both the H and L chains. It is also possible to synthesize a synthetic DNA of a full length of variable region to use this DNA.

In addition, by introducing a recognition sequence for an appropriate restriction enzyme into the 5'-terminal of the synthetic DNA positioned on the both ends, it is possible to easily clone the cDNA encoding VH or VL of a humanized antibody to the vector for expressing a humanized antibody obtained in the section (1).

After PCR, the amplified products are cloned respectively to a plasmid such as pBluescript SK(−) (manufactured by Stratagene) or the like, and the nucleotide sequence is determined by the same method as the method described in the section (2), thereby obtaining a plasmid having a DNA sequence encoding the amino acid sequence of VH or VL of a desired humanized antibody.

(5) Modification of Amino Acid Sequence of V Region of Humanized Antibody

If a humanized antibody is obtained by simply grafting CDR of VH and VL of a non-human antibody to FR of VH and VL of a human antibody, the antigen binding activity of the humanized antibody is lower than that of the original non-human antibody [BIO/TECHNOLOGY, 9, 266 (1991)]. For the humanized antibody, an amino acid residue directly involved in binding to an antigen, an amino acid residue which interacts with the amino acid residue of CDR, and an amino acid residue which maintains the three-dimensional structure of the V region of the antibody and is indirectly involved in binding to an antigen are identified from among amino acid sequences of FR of VH and VL of a human antibody, and these amino acid residues are substituted with the amino acid residues of the original non-human antibody, whereby the decreased antigen binding activity can be recovered.

In order to identify the amino acid residues of FR involved in the antigen binding activity, X-ray crystallography [J. Mol. Biol., 112, 535 (1977)], computer modeling [Protein Engineering, 7, 1501 (1994)] or the like is used, whereby the three-dimensional structure of the antibody can be constructed and analyzed. In addition, several types of modified antibodies are prepared for the respective antibodies, and correlation between these antibodies and the antigen binding activity is repeatedly examined, whereby it is possible to obtain modified humanized antibodies having required antigen binding activity.

The amino acid residues of FR of VH and VL of a human antibody can be modified by PCR described in the section (4) by using synthetic DNA for modification. Nucleotide sequences are determined for the amplified product obtained after PCR by the method described in the section (2), thereby confirming the state where the modification has been completed as desired.

(6) Construction of Humanized Antibody Expression Vector cDNAs encoding VH or VL of the constructed recombinant antibody are cloned respectively to the upstream of the respective genes encoding CH or CL of the human antibody of the vector for expressing a recombinant antibody obtained in the section (1), whereby a humanized antibody expression vector can be constructed.

For example, among the synthetic DNAs used for constructing VH or VL of a humanized antibody obtained in the sections (4) and (5), a recognition sequence for an appropriate restriction enzyme is introduced to the 5'-terminal of the synthetic DNA positioned in both ends, whereby the DNAs are cloned respectively such that they are expressed in an appropriate form in the upstream of the respective genes encoding CH or CL of the human antibody of the vector for expressing a humanized antibody obtained in the section (1).

(7) Transient Expression of Recombinant Antibody

The recombinant antibody expression vectors obtained in the sections (3) and (6) or expression vectors obtained by modifying those vectors are used to cause transient expression of the recombinant antibody. In this manner, it is possible to efficiently evaluate the antigen binding activity of the prepared various types of humanized antibodies.

Any type of cell can be used as the host cell to which the expression vector is introduced, as long as it is a host cell which can express a recombinant antibody, and for example, COS-7 cell [American Type Culture Collection (ATCC) No. CRL1651] is used [Methods in Nucleic Acids Res., CRC press, 283 (1991)]. For introducing an expression vector to COS-7 cell, a DEAE dextran method [Methods in Nucleic Acids Res., CRC press, (1991)], lipofection [Proc. Natl. Acad. Sci. USA, 84, 7413 (1987)], or the like is used.

After the introduction of an expression vector, the expression amount and the antigen binding activity of the recombinant antibody in the culture supernatant are measured by ELISA [Monoclonal Antibodies—Principles and practice, Third edition, Academic Press (1996), Antibodies—A Laboratory Manual, Cold Spring Harbor Laboratory (1988), Manual for Monoclonal Antibody Experiment, Kodansha Scientific Ltd. (1987)] or the like.

(8) Obtaining Transformant which Stably Expresses Recombinant Antibody and Preparation of Recombinant Antibody By introducing the recombinant antibody expression vectors obtained in the sections (3) and (6) into an appropriate host cell, it is possible to obtain a transformant which stably expresses a recombinant antibody. For introduction of an expression vector into a host cell, for example, electroporation [JP-A-2-257891, Cytotechnology, 3, 133 (1990)], a calcium ion method, a spheroplast method, a lithium acetate method, a calcium phosphate method, lipofection, or the like is used. Moreover, examples of the method of introducing a gene into an animal described later include microinjection, a method of introducing a gene into ES cell by using electroporation or a lipofection, nuclear graft, and the like.

Any type of cell can be used as a host cell to which the recombinant antibody expression vector is introduced, as long as the cell can express the recombinant antibody. For example, mouse SP2/0-Ag14 cell (ATCC No. CRL1581), mouse P3X63-Ag8.653 cell (ATCC No. CRL1580), dihydrofolate reductase gene (hereinbelow, described as "dhfr")-deficient CHO cell [Proc. Natl. Acad. Sci. USA, 77, 4216 (1980)], lectin resistance-acquired Lec13 [Somatic Cell and Molecular genetics, 12, 55 (1986)], α1,6-fucosyltransferase gene-knockout CHO cell (WO 2005/035586 and WO 02/31140), rat YB2/3HL.P2.G11.16Ag.20 cell (ATCC No. CRL1662), or the like is used.

It is also possible to use host cells (WO 2003/85102) in which a protein such as an enzyme involved in synthesis of intracellular sugar nucleotide GDP-fucose, a protein such as an enzyme involved in the modification of a sugar chain in which 1-position of fucose is bound to 6-position of N-acetylglucosamine in the reducing end through α-bond in the complex N-glycoside-linked sugar chain. or a protein involved in transporting an intracellular sugar nucleotide GDP-fucose to the Golgi body exhibits lowered activity or is deficient, for example, α1,6-fucosetransferase gene-knockout CHO cell (WO 2005/035586 and WO 02/31140) or the like.

After introduction of the expression vector, transformants which stably express the recombinant antibody are selected by being cultured in a medium for culturing animal cells which contain a drug such as G418 sulfate (hereinbelow, described as G418) (JP-A-2-257891).

Examples of the medium for culturing animal cells include RPMI1640 medium (manufactured by Invitrogen), GIT medium (manufactured by NIHON PHARMACEUTICAL CO., LTD), EX-CELL301 medium, EX-CELL302 medium, and EX-CELL325 medium (manufactured by JRH Biosciences), IMDM (manufactured by Invitrogen), Hybridoma-SFM (manufactured by Invitrogen), these media supplemented with various additives such as FBS and the like.

The obtained transformant is cultured in the medium, thereby expressing and accumulating recombinant antibody in the culture supernatant. The expression amount and the antigen binding activity of the recombinant antibody in the culture supernatant can be measured by ELISA or the like. For the transformant, the expression amount of the recombinant antibody can be increased by using DHFR amplification system (JP-A-2-257891) or the like.

The recombinant antibody is purified from the culture supernatant of the transformant by using a Protein A column [Monoclonal Antibodies-Principles and practice, Third edition, Academic Press (1996), Antibodies—A Laboratory Manual, Cold Spring Harbor Laboratory (1988)]. It is also possible to combine methods used for protein purification, such as gel filtration, ion-exchange chromatography, and ultrafiltration.

The molecular weight of the H- and L-chains or the total antibody molecules of the purified recombinant antibody can be measured by polyacrylamide gel electrophoresis [Nature, 227, 680 (1970)], Western blotting [Monoclonal Antibodies-Principles and practice, Third edition, Academic Press (1996), Antibodies—A Laboratory Manual, Cold Spring Harbor Laboratory (1988)], or the like.

3. Evaluation of Activity of Purified Monoclonal Antibody or the Antibody Fragment Thereof The activity of the purified monoclonal antibody of the present invention or the antibody fragment thereof can be evaluated in the following manner.

The binding activity with respect to the erbB3-expressing cell line can be measured using the binding assay system described in the above section 1-(7). The CDC activity or the ADCC activity with respect to an antigen positive cell line can be measured by known measurement methods [Cancer Immunol. Immunother., 36, 373 (1993)].

The EGF-like ligand-dependent phosphorylation of erbB3 and the erbB3-specific ligand-independent phosphorylation of erbB3 can be measured in the following manner.

erbB3-expressing cells are washed with PBS, a serum-free medium, or the like, and then cultured for about 24 hours in a serum-free medium. Subsequently, the erbB3-expressing cells are cultured for several minutes to several tens of minutes using a medium supplemented with a target antibody and several ng/mL to several tens of ng/mL of erbB3 receptor ligand. Subsequently extract of the cell is prepared, and the respective proteins are immunoprecipitated using an erbB3-specific antibody and a house keeping gene (actin or the like)-specific antibody.

The precipitated proteins are subjected to electrophoresis using SDS-PAGE, followed by Western blotting by using the erbB3-specific antibody and the phosphorylated tyrosine-specific antibody, whereby it is possible to measure the inhibitory activity against phosphorylation of erbB3.

Alternatively, the cultured cells to which the antibodies have been added are subjected to protein immobilization and cell membrane permeation treatment by using formaldehyde and saponine, and FCM analysis is carried out using the erbB3-specific antibody or the phosphorylated tyrosine-specific antibody. The phosphorylation of erbB3 can also be confirmed in this manner.

In addition, regarding dimerization of erbB3, culturing and preparation of cell lysate are performed in the same manner as in the test for detecting phosphorylation described above, and then the erbB3 proteins are immunoprecipitated using the anti-erbB3 antibody so as to detect the precipitated proteins by antibodies against the each erbB family protein, whereby it is possible to detect dimerization or heterodimerization of erbB3.

4. Method of Regulating Effector Activity of Antibody

Examples of methods of regulating the effector activity of the anti-erbB3 antibody of the present invention include a method of regulating the amount of fucose (also referred to as "core fucose") which forms $\alpha 1,6$-bound to N-acetylglucosamine (GlcNAc) present in a reducing end of a complex type N-linked sugar chain bound to asparagine (Asn) at position 297 of the Fc region of the antibody (WO 2005/035586, SO 2003/85102, WO 2002/31140, WO 00/61739), a method of modifying amino acid residues in the Fc region of the antibody, and the like. The effector activity of the anti-erbB3 antibody of the present invention can be regulated by using any of these methods.

The "effector activity" refers to an antibody-dependent activity induced via the Fc region of an antibody. As the effector activity, Antibody-Dependent Cellular Cytotoxicity activity (ADCC activity), Complement-Dependent Cytotoxicity activity (CDC activity), antibody-dependent phagocytosis (ADP activity) caused by a phagocyte such as a macrophage or a dendritic cell, and the like are known.

The effector activity of an antibody can be increased or decreased by regulating the content of the core fucose in the complex type N-linked sugar chain of Fc of the antibody. As a method of decreasing the content of fucose binding to the complex type N-liked sugar chain bound to Fc of the antibody, the antibody is expressed using $\alpha 1,6$-fucosetransferase gene-deficient CHO cell, whereby an antibody to which fucose has not bound can be obtained. The defucosylated antibody has a higher ADCC activity than that of the fucosylated antibody.

On the other hand, as a method of increasing the content of fucose binding to the complex type N-linked sugar chain bound to Fc of an antibody, an antibody is expressed using a host cell to which $\alpha 1,6$-fucosetransferase gene has been introduced, whereby an fucosylated antibody can be obtained. The ADCC activity of the fucosylated antibody is lower than that of the defucosylated antibody.

Modifying amino acid residues of the Fc region of an antibody makes it possible to increase or decrease the ADCC or CDC activity. If amino acid residues of the Fc region are modified, binding activity to FcγR is enhanced or lowered, whereby the ADCC activity can be regulated. In addition, if amino acid residues of the Fc region are modified, the binding activity of a complement is increased or decreased, whereby the CDC activity can be regulated.

For example, the CDC activity of an antibody can be enhanced using the amino acid sequence of the Fc region disclosed in the specification of US Patent Application Publication No. 2007/0148165. In addition, the ADCC activity or CDC activity can also be enhanced or lowered by performing amino acid modification described in the specification of U.S. Pat. No. 6,737,056, the specification of U.S. Pat. No. 7,297,775, the specification of U.S. Pat. No. 7,317,091, or WO 2005/070963.

Furthermore, by using a combination of the method of regulating a sugar chain described above and the method of modifying amino acid residues of the Fc region, it is possible to obtain an antibody of which the effector activity has been regulated.

5. Method of Treating Diseases by Using Anti-erbB3 Antibody or an Antibody Fragment Thereof of the Present Invention The antibody or the antibody fragment thereof of the present invention, which specifically recognizes the extracellular domain of erbB3 and inhibits EGF-like ligand-dependent phosphorylation of erbB3, can be used for treating erbB3-related hyper proliferative diseases such as cancer.

Examples of erbB3-related diseases include colon cancer, colorectal cancer, lung cancer, breast cancer, glioma, malignant melanoma, thyroid cancer, renal cell carcinoma, leukemia, lymphoma, T cell lymphoma, gastric cancer, pancreatic cancer, cervical cancer, endometrial cancer, ovarian cancer, esophageal cancer, hepatoma, head and neck squamous cell carcinoma, skin cancer, urinary tract cancer, bladder cancer, prostate cancer, choriocarcinoma, pharyngeal cancer, laryngeal cancer, pleural tumor, arrhenoblastoma, endometrial hyperplasia, endometriosis, embryoma, fibrosarcoma, Kaposi's sarcoma, hemangioma, cavernous hemangioma, angioblastoma, retinoblastoma, astrocytoma, neurofibromatosis, oligodendrogligoma, medulloblastoma, neuroblastoma, neuroglioma, rhabdomyosarcoma, glioblastoma, osteosarcoma, leiomyosarcoma, thyroid sarcoma, Wilms tumor, and the like.

Further the above diseases also can be treated using two or more anti-erbB3 antibodies of the present invention. Specifically, for example, antibodies of the respective domains including domains 1 to 4 of erbB3 can be used in combination. Examples of the treatment method preferably include a treatment method comprising administering an antibody binding to the domain 1 or 3 of erbB3 and an antibody binding to the domain 2 or 4 of erbB3, and most preferably include a treatment method comprising administering an antibody binding to the domain 1 of erbB3 and an antibody binding to the domain 4 of erbB3.

A therapeutic agent comprising the antibody or the antibody fragment thereof of the present invention or comprising these derivatives may contain only the antibody or the antibody fragment thereof of the present invention, or the these derivatives, as an active ingredient. Generally, the therapeutic agent is provided as a pharmaceutical preparation which is mixed with one or more pharmaceutically acceptable carriers and produced by a method known in the technical field of pharmaceutics.

Examples of the route of administration include oral administration and non-oral administration such as buccal, intratracheal, intrarectal, subcutaneous, intramuscular, or intravenous administration. Examples of form of administration include sprays, capsules, tablets, powder, granules, syrups, emulsions, suppositories, injections, ointments, tapes, and the like.

Various preparations can be produced by common methods by using an excipient, an extender, a binder, a wetting-out agent, a disintegrating agent, a surfactant, a lubricant, a dispersant, a buffering agent, a preservative, a dissolution adjuvant, an antiseptic, a colorant, a flavoring agent, a stabilizing agent, and the like which are generally used.

Examples of the excipient include lactose, fructose, glucose, corn starch, sorbitol, crystalline cellulose, sterilized water, ethanol, glycerol, physiological saline, a buffer, and the like. Examples of the disintegrating agent include starch, sodium alginate, gelatin, calcium carbonate, calcium citrate, dextrin, magnesium carbonate, synthetic magnesium silicate, and the like.

Examples of the binder include methyl cellulose or a salt thereof, ethyl cellulose, gum Arabic, gelatin, hydroxypropyl cellulose, polyvinyl pyrrolidone, and the like. Examples of the lubricant include talc, magnesium stearate, polyethylene glycol, hardened plant oil, and the like.

Examples of the stabilizing agent include amino acids such as arginine, histidine, lysine, and methionine, human serum albumin, gelatin, dextran-40, methyl cellulose, sodium sulfite, sodium metabisulfite, and the like.

Examples of other additives include a syrup, vaseline, glycerin, ethanol, propylene glycol, citric acid, sodium chloride, sodium nitrite, sodium phosphate, and the like.

Preparations suitable for oral administration include an emulsion, a syrup, a capsule, a tablet, powder, granules, and the like.

Liquid preparations such as an emulsion and a syrup are produced using additives including water, saccharides such as sucrose, sorbitol, and fructose, glycols such as polyethylene glycol and propylene glycol, oils such as sesame oil, olive oil, and soy bean oil, antiseptics such as p-hydroxybenzoic acid ester, and flavors such as a strawberry flavor and peppermint.

Capsules, tablets, powder, granules, and the like are produced using additives including an excipient such as lactose, glucose, sucrose, or mannitol, a disintegrating agent such as starch or sodium alginate, a lubricant such as magnesium stearate or talc, a binder such as a polyvinyl alcohol, hydroxypropyl cellulose, or gelatin, a surfactant such as fatty acid ester, and a plasticizer such as glycerin.

Examples of preparations suitable for non-oral administration include an injection, a suppository, a spray, and the like.

The injection is produced using a carrier such as a salt solution, a glucose solution, or a mixture of both of them.

The suppository is produced using a carrier such as cacao butter, hydrogenated fat, or carboxylic acid.

The spray is produced using a carrier or the like which does not irritate the oral cavity and airway mucosa of a user, disperse the monoclonal antibody or the antibody fragment thereof of the present invention as fine particles, and facilitates absorption. As the carrier, lactose or glycerin is used. An aerosol or dry powder can also be produced.

In addition, the components exemplified above as additives for preparations suitable for oral administration can also be added to the above preparation for non-oral administration.

The effective dose administered as a combination of the effective does of the antibody of the present invention and an appropriate diluent with a pharmaceutically usable carrier is 0.0001 mg to 100 mg/kg (body weight) per administration, and is administered in a term of 2 days to 8 weeks.

6. Method of Diagnosing Diseases by Using Anti-erbB3 Monoclonal Antibody or the Antibody Fragment Thereof of the Present Invention erbB3 or a cell expressing erbB3 is detected or measured using the antibody or the antibody fragment thereof of the present invention, whereby it is possible to diagnosing erbB3-related diseases.

Cancer which is one of the erbB3-related diseases can be diagnosed by, for example, detecting or measuring erbB3 in the following manner.

First, regarding biological samples resected from the body of a plurality of healthy individuals, detection or measurement of erbB3 is performed using the following immunological technique by using the monoclonal antibody or the antibody fragment thereof of the present invention or derivatives thereof, thereby investigating the amount of erbB3 present in the biological samples of healthy individuals. Thereafter, the amount of erbB3 present in biological samples of subjects is also detected, and the amount of erbB3 present in subject is compared with the amount of erbB3 present in healthy individuals. When the amount of the polypeptide in the subjects is larger than that in the healthy individuals, cancer is diagnosed as positive.

The immunological technique is a method of detecting or measuring the amount of an antibody or an antigen by using a labeled antigen or antibody. Examples of the technique include a radioactive substance-labeled immunoantibody method, enzyme immunoassay, fluorescence immunoassay, luminescence immunoassay, Western blotting, a physicochemical technique, and the like.

In the radioisotope-labeled immunoantibody method, for example, the antibody or the antibody fragment thereof of the present invention is bound with an antigen, a cell expressing the antigen, or the like, and further bound with an anti-immunoglobulin antibody having undergone radioisotope labeling or with a binding fragment, followed by measurement by using a scintillation counter or the like.

In the enzyme immunoassay, for example, the antibody or the antibody fragment thereof of the present invention is bound with an antigen, a cell expressing the antigen, or the like, and further bound with a labeled anti-immunoglobulin antibody or with a binding fragment, and then the developed color is measured using an absorptiometer. Examples of this method include sandwich ELISA and the like.

As a label used in the enzyme immunoassay, known enzyme labels [Enzyme immunoassay, Igaku-Shoin, Ltd (1987)] can be used. Examples of the label include an alkaline phosphatase label, a peroxidase label, a luciferase label, a biotin label, and the like.

The sandwich ELISA is a method in which an antibody is bound to a solid phase, an antigen to be detected or measured is then trapped, and the trapped antigen is bound with a second antibody. In this ELISA, two kinds of antibodies each of which is an antibody or an antibody fragment recognizing an antigen desired to be detected or measured and has different antigen recognition site are prepared. Among the antibodies, a first antibody or the antibody fragment is adsorbed onto a plate (for example, a 96-well plate) in advance, and then a second antibody or the antibody fragment is labeled with a fluorescent substance such as FITC, an enzyme such as peroxidase, or biotin.

The plate to which the antibody has been adsorbed is bound with a cell or a homogenate thereof, a tissue or a homogenate thereof, a cell culture supernatant, serum, pleural effusion, ascites fluid, ocular fluid, or the like isolated from the body and then bound with a labeled monoclonal antibody or the antibody fragment, thereby causing a detection reaction according to the labeling substance. The antigen concentration in the subject sample is calculated from a calibration curve which is created by stepwise dilution of an antigen of known concentration.

Any of polyclonal and monoclonal antibodies may be used as the antibody used in the sandwich ELISA, and antibody fragments such as Fab, Fab', and F(ab)$_2$ may also be used. The combination of two kinds of antibodies used in the sandwich ELISA may be a combination of monoclonal antibodies or antibody fragments recognizing different epitopes or may be a combination of a polyclonal antibody and a monoclonal antibody or the antibody fragment.

The fluorescence immunoassay is carried out by methods described in a documents [Monoclonal Antibodies-Principles and practice, Third edition, Academic Press (1996), Manual for Monoclonal Antibody Experiment, Kodansha Scientific (1987)] and the like. As a label used in the fluorescence immunoassay, a known fluorescent label [Fluorescent Antibody Method, Soft Science (1983)] can be used, and examples thereof include FITC, RITC, and the like.

The luminescence immunoassay can be carried out by methods described in a document [Bioluminescence and Chemical luminescence-Clinical Test 42, Hirokawa Shoten (1998)] and the like. Examples of labels used in the luminescence immunoassay include known luminescent labels such as acrydinium ester and lophine.

In the Western blotting, an antigen, a cell expressing the antigen, or the like is fractionated by SDS (sodium dodecyl sulfate)-PAGE (Antibodies—A Laboratory Manual Cold Spring Harbor Laboratory (1988)], the gel is then blotted onto a polyvinylidene fluoride (PVDF) membrane or a nitrocellulose membrane. Thereafter, the membrane is bound with an antibody recognizing an antigen or the antibody fragment and further bound with an anti-mouse IgG antibody or the binding fragment labeled with a fluorescent substance such as FITC, an enzyme such as peroxidase, or biotin, and then the label is visualized to perform measurement. An example of the Western blotting will be shown below.

A cell or a tissue expressing a polypeptide having the amino acid sequence represented by SEQ ID NO:2 is dissolved, and electrophoresis is performed on the protein in an amount of 0.1 μg to 30 μg/lane under reducing conditions based on the SDS-PAGE method. The protein having undergone electrophoresis is transferred to a PVDF membrane and reacted with PBS containing 1% to 10% BSA (hereinbelow, described as "BSA-PBS") for 30 minutes at room temperature to perform blocking.

The monoclonal antibody of the present invention is bound with the resultant, washed with PBS containing 0.05% to 0.1% Tween-20 (hereinbelow, described as "Tween-PBS"), and bound with goat anti-mouse IgG labeled with peroxidase for 2 hours. The resultant is washed with Tween-PBS, and a band to which the monoclonal antibody has bound is detected using ECL® Western Blotting Detection Reagents (manufactured by Amersham Pharmacia Biotech) or the like, thereby detecting a polypeptide having the amino acid sequence represented by SEQ ID NO:2.

As the antibody used for detection in the Western blotting, an antibody which can be bound to a polypeptide which does not have a natural three-dimensional structure is used.

The physicochemical technique is performed by, for example, a method in which erbB3 as an antigen is bound to the monoclonal antibody or the antibody fragment thereof of the present invention to form an aggregate, and the aggregate is detected. Other example of the physicochemical technique include a capillary method, one-dimensional immunodiffusion, immunoturbidimetry, latex immunoturbidimetry [Handbook of Clinical Test Methods, KANEHARA & Co., LTD (1998)], and the like.

In the latex immunoturbidimetry, a carrier such as polystyrene latex having a particle size of about 0.1 μm to 1 μm sensitized with an antibody or an antigen is used to cause an antigen-antibody reaction by using the corresponding antigen or antibody. At this time, scattered light in the reaction solution increases while transmitted light decreases. This change is detected as absorbance or integral sphere turbidity, whereby antigen concentration or the like in the subject sample is measured.

Meanwhile, known immunological detection methods can be used for detecting or measuring the cell expressing erbB3, and preferably, immunoprecipitation, immunocellular staining, immunohistochemical staining, immunofluorescence staining, and the like are used.

In the immunoprecipitation, a cell or the like expressing erbB3 is bound with the monoclonal antibody or the antibody fragment thereof of the present invention, and then a carrier having an ability of binding specifically to immunoglobulin, such as protein G-sepharose, is added thereto to precipitate an antigen-antibody complex.

In addition, the following method can also be used. The monoclonal antibody or the antibody fragment thereof of the present invention described above is immobilized onto a 96-well plate for ELISA, followed by blocking using BSA-PBS.

When the antibody is crude such as culture supernatant of hybridoma, anti-mouse immunoglobulin, anti-rat immunoglobulin, protein A, protein G, or the like is immobilized onto the 96-well plate for ELISA in advance, followed by blocking by using BSA-PBS, and then the culture supernatant of hybridoma is dispensed thereto for binding.

Subsequently, BSA-PBS is discarded, the plate is sufficiently washed with PBS, and then a solution of a cell or tissue expressing erbB3 is bound with the antibody. After the plate is sufficiently washed, immunoprecipitate is extracted from the plate by using a sample buffer for SDS-PAGE, and Western blotting is carried out for detection.

The immunocellular staining or the immunohistochemical staining is a method that a cell, tissue, or the like expressing an antigen is bound with the monoclonal antibody of the present invention, and further bound with an anti-immunoglobulin antibody or the binding fragment thereof labeled with a fluorescent label such as FIT, an enzyme such as peroxidase, biotin, or the like, and the label is visualized and observed with a microscope. The method is optionally treated with a surfactant or methanol so as to make an antibody permeate easily before antibody reaction.

Cells can also be detected by the immunofluorescence staining in which the cells are bound with a fluorescence-labeled antibody and analyzed by flow cytometer [Monoclonal Antibodies-Principle and practice, Third edition, Academic Press (1996), Manual for Monoclonal Antibody Experiment, Kodansha Scientific (1987)]. Particularly, the antibody or the antibody fragment thereof of the present invention which binds to the extracellular domain of erbB3 makes it possible to detect erbB3 expressed on a cell membrane by the immunofluorescence staining.

When FMAT8100HTS system (manufactured by Applied Biosystems) is used in the immunofluorescence staining, it is possible to measure the amount of an antigen or antibody without separating a free antibody or a free antigen not involved in the formation of the antibody-antigen complex from the formed antigen-antibody complex.

EXAMPLES

Hereinbelow, the present invention will be described in more detail by using examples, but the present invention is not limited to the following examples.

Example 1

Preparation of erbB3 Antigen

1. Human erbB3-Fc Protein Expression Vector

A cDNA fragment of Fc fusion protein wherein the extracellular domain (SEQ ID NO:3) of human erbB3 is fused with human IgG1-Fc region (hereinbelow, described as "erbB3-Fc") was prepared in the following manner. A DNA fragment encoding the amino acid sequence in the extracellular domain of erbB3 was amplified using a primer of SEQ ID NO: 7 and a primer of SEQ ID NO:8, Human lung Marathon Ready cDNA (manufactured by Clontech) as a template, and KOD Plus® DNA polymerase (manufactured by TOYOBO Co., Ltd.), by PCR performed for 35 cycles each consisting of 94° C. for 15 seconds, 60° C. for 30 seconds, and 68° C. for 2 minutes. This erbB3 gene fragment was digested with restriction enzymes KpnI and XbaI and inserted into an appropriate site of INPEP4 vector (manufactured by Biogen-IDEC) comprising the Fc region of human IgG, thereby preparing erbB3-Fc expression vector.

2. Preparation of Human-erbB3-GST Protein Expression Vector

The respective expression vectors were prepared in the following experiment using PCR condition and treatment by restriction enzyme described in the section 1, unless otherwise specified.

A cDNA fragment of a GST fusion protein wherein the extracellular domain (SEQ ID NO:3) of human erbB3 is fused to glutathione S-transferase (hereinbelow, described as "GST") (hereinbelow, described as "herbB3-GST") was prepared in the following manner.

A cDNA fragment of the extracellular domain of human erbB3 was amplified using a primer of SEQ ID NO:9, a primer of SEQ ID NO:10, and Human lung Marathon Ready cDNA (manufactured by Clontech) as a template, by PCR performed for 35 cycles consisting of 94° C. for 15 seconds, 60° C. for 15 seconds, and 68° C. for 2 minutes. This gene fragment was digested with restriction enzymes KpnI and BglII and inserted into an appropriate site of INPEP4 vector (manufactured by Biogen-IDEC) comprising GST, thereby preparing a herbB3-GST expression vector.

3. Preparation of Mouse erbB3-GST Protein Expression Vector

A cDNA fragment of a GST fusion protein wherein the extracellular domain (SEQ ID NO:6) of mouse erbB3 is fused to GST (hereinbelow, described as "merbB3-GST") was amplified using Mouse lung Marathon Ready cDNA (manufactured by Clontech) as a template, a primer of SEQ ID NO:11, and a primer of SEQ ID NO:12, by PCR performed for 35 cycles consisting of 94° C. for 30 seconds, 65° C. for 15 seconds, and 68° C. for 2 minutes. The amplified cDNA fragment was digested with restriction enzymes MuI and BglII. In the following operation, a mouse erbB3-GST expression vector was prepared in the same manner as in the section 1 of [Example 1].

4. Preparation of Human-Mouse Chimeric erbB3-Fc Protein Expression Vector

In order to investigate the binding region of the anti-erbB3 antibody, expression vectors for a chimeric protein wherein the domains 2 to 4 of the extracellular domain of human erbB3 is fused with the domains 2 to 4 of mouse erbB3 (hereinbelow, described as "hD1/mD234"), a chimeric protein wherein the domains 3 and 4 of the extracellular domain of human erbB3 is fused with the domains 3 and 4 of mouse erbB3 (hereinbelow, described as "hD12/mD34") and a chimeric protein wherein the domain 4 of the extracellular domain of human erbB3 is fused with the domain 4 of mouse erbB3 (hereinbelow, described as "hD123/mD4") were prepared in the following manner.

(1) Preparation of hD1/mD234 Expression Vector

A cDNA fragment of human erbB3-D1 was amplified using human erbB3 cDNA as a template, a primer of SEQ ID NO:13, and a primer of SEQ ID NO:14, by PCR performed for 35 cycles consisting of 94° C. for 30 seconds, 65° C. for 15 seconds, and 68° C. for 30 seconds. On the other hand, a cDNA fragment of mouse erbB3-D234 was amplified using mouse erbB3 cDNA as a template, a primer of SEQ ID NO:15, and a primer of SEQ ID NO:16, by PCR performed for 35 cycles consisting of 94° C. for 30 seconds, 65° C. for 15 seconds, and 68° C. for 90 seconds.

PCR was performed for 5 cycles consisting of 94° C. for 30 seconds, 65° C. for 15 seconds, and 68° C. for 2 minutes, by using a template which was a mixture of a purified cDNA fragment of human erbB3-D1 and a purified cDNA fragment of mouse erbB3-D234, and then a primer of SEQ ID NO:17 and a primer of SEQ ID NO:18 were added to reaction mixture, PCR was performed for 35 cycles consisting of 94° C. for 30 seconds, 65° C. for 15 seconds and 68° C. for 2 minutes, thereby amplifying a cDNA fragment of hD1/mD234. This gene fragment was digested with restriction enzymes MluI and BglII and inserted into GST-containing INPEP4 vector (manufactured by Biogen-IDEC), thereby preparing a hD1/mD234 expression vector.

(2) Preparation of hD12/mD34 Expression Vector

A cDNA fragment of human erbB3-D12 was amplified using human erbB3 cDNA as a template, a primer of SEQ ID NO:19 and a primer of SEQ ID NO:20, by PCR performed for 35 cycles consisting of 94° C. for 30 seconds, 65° C. for 15 seconds and 68° C. for 1 minute.

On the other hand, a cDNA fragment of mouse erbB3-D34 was amplified using mouse erbB3 cDNA as a template, a primer of SEQ ID NO:21 and a primer of SEQ ID NO:22, by PCR performed for 35 cycles consisting of 94° C. for 30 seconds, 65° C. for 15 seconds and 68° C. for 90 seconds. These two amplified cDNA fragments, a primer of SEQ ID NO:23 and a primer of SEQ ID NO:24 underwent the same process as in the above section (1), thereby preparing a hD12/mD34 expression vector.

(3) Preparation of hD123/mD4 Expression Vector

A cDNA fragment of human [[erbB2]]erbB3-D123 was amplified using human erbB3 cDNA as a template, a primer of SEQ ID NO:25 and a primer of SEQ ID NO:26, by PCR performed for 35 cycles consisting of 94° C. for 30 seconds, 65° C. for 15 seconds and 68° C. for 2 minutes.

On the other hand, a cDNA fragment of mouse erbB3-D4 was amplified using mouse erbB3 cDNA as a template, a primer of SEQ ID NO:27 and a primer of SEQ ID NO:28, by PCR performed for 35 cycles consisting of 94° C. for 30 seconds, 65° C. for 15 seconds and 68° C. for 90 seconds. These two amplified cDNA fragments, a primer of SEQ ID NO:29 and a primer of SEQ ID NO:30 underwent the same process as in the above section (1), thereby preparing a hD123/mD4 expression vector.

5. Preparation of erbB3-Fc Protein and erbB3-GST Protein

The erbB3-Fc protein expression vector and erbB3-GST protein expression vector prepared in the above sections 1 to 4 were respectively introduced into FreeStyle 293F cell by using FreeStyle293 Expression kit (manufactured by Invitrogen), according to the instruction attached to the kit. The culture supernatant was recovered on the fifth day after the vector introduction and treated with a 0.2 μm filter (manufactured by Millipore Corporation).

The erbB3-Fc protein was subjected to affinity purification by using a Protein A resin (MabSelect®, manufactured by Amersham Pharmacia Biotech). A phosphate buffer (PBS) was used as a wash solution, and 20 mM sodium citrate and 50 mM NaCl buffer (pH 2.7) were used as an elution buffer. A 200 mM sodium phosphate buffer (pH 7.0) was added to the eluted fractions to adjust pH to around 6.0.

For the erbB3-GST protein, 1 mL of a Glutathione Sepharose 4B (manufactured by Amersham Pharmacia Biotech) resin suspension was added based on 125 mL of the culture supernatant, followed by reaction at 4° C. for 4 hours. Thereafter, the resin was washed with a phosphate buffer, and the respective domain peptides were subjected to affinity purification by using 10 mM Glutathione in 50 mM Tris-HCl (pH 8.0) as an elution buffer.

The eluted fusion protein solution was substituted with a phosphate buffer by using a dialysis membrane (10000 cut, manufactured by Spectrum Laboratories, Ltd) and sterilized by being filtered through a membrane filter MILLEX-GV (manufactured by Millipore Corporation) having a pore size of 0.22 μm, thereby preparing erbB3-Fc protein and erbB3-GST protein.

Each concentration of the erbB3-Fc protein and the erbB3-GST protein was calculated by measuring an absorbance at 280 nm and setting the concentration of a fusion protein solution showing 0.86 optimal density to be 1 mg/mL.

Example 2

Preparation of Anti-Human erbB3 Antibody

In the present example, a monoclonal antibody was prepared by a general method disclosed in "Introduction to Monoclonal Antibody Experiment Manual" (Andou Tamie et al., Kodansha, 1991) or the like. C3H/Hej jms Slc-lpr/lpr mice commercially available from Japan SLC, Inc., were used as immunized animals.

An antigen protein such as erbB3-Fc was mixed with MPL+TDM EMULSION (RiBi manufactured by Sigma-Aldrich Co., LLC. Ca No. 52-0177-00) at a ratio of 1:1 and administered into right abdominal cavity of mice at a dose of 20 μg/mouse as the first immunization. After the first immunization, the antigen was administered plural times to the mice for 7 to 9 days at a dose of 10 μg to 20 μg/mouse to immunize the mice. Moreover, for cell fusion, 3 days before obtaining spleen and lymph node, the same antigen was administered into right abdominal cavity to immunize the mice. Antibody titer measurement begun from the second antigen immunization, and since then, antibody titer was measured over time and the timing of resecting spleen or the like was decided.

10 mL of a serum-free DMEM (manufactured by Gibco BRL) (hereinbelow, described as "serum-free DMEM") containing 350 mg/mL sodium hydrogen carbonate, 50 units/mL penicillin, and 50 μg/mL streptomycin were added to the spleen and lymph node surgically excised from the mouse immunized with the antigen, and these organs were crushed with a spatula on a mesh (cell strainer; manufactured by Falcon). The cell suspension passed through the mesh was centrifuged to precipitate cells, and then the cells were washed twice with the serum-free DMEM and then suspended in the serum-free DMEM, thereby measuring the number of cells.

Meanwhile, 8-azaguanine-resistant mouse myeloma P3X63Ag8U. 1(P3-U1) was subcultured at 37° C. and at a cell concentration of $1 \times 10^8$ cells/mL or less in the presence of 5% $CO_2$, by using a DMEM (manufactured by Gibco BRL) (hereinbelow, described as a "serum-containing DMEM") containing 10% fetal calf serum (hereinbelow, abbreviated to "FCS") (manufactured by Sigma-Aldrich Co., LLC.) and L-Glu.

The cultured mouse myeloma cells were washed with the serum-free DMEM in the same manner as described above and suspended in the serum-free DMEM, thereby measuring the number of cells. The recovered cell suspension derived from mouse spleen and lymph node and the mouse myeloma suspension were mixed with each other at a ratio of 5:1 in terms of the number of cells. This cell mixture solution was centrifuged, and then the supernatant was completely removed.

As a fusion agent, 1 mL of 50% (w/v) polyethylene glycol 1500 (manufactured by Boehringer Mannheim) was slowly added to the pellet by using a pipette while the pellet was being stirred with the tip of the pipette. Thereafter, 1 mL of the serum-free DMEM pre-heated to 37° C. was slowly added thereto in two divided steps, and 7 mL of the serum-free DMEM was further added thereto. After centrifugation, the supernatant was removed, and the thus obtained fusion cells were subjected to screening performed by limiting dilution described below.

A hybridoma was selected by being cultured in a DMEM (HAT medium) containing 10% FCS, hypoxanthine (H), aminopterin (A), and thymidine (T) (hereinbelow, referred to as "HAT" (manufactured by Sigma-Aldrich Co., LLC.)).

The hybridoma was single-cloned by limiting dilution using a HT (manufactured by Sigma-Aldrich Co., LLC.)-containing DMEM (HT medium). Culturing was performed in a 96-well microtiter plate (manufactured by Becton, Dickinson and Company).

The screening of hybridoma producing the anti-human erbB3 monoclonal antibody and the analysis of reacting specificity of the monoclonal antibody produced from the respective hybridomas were carried out by Enzyme-linked immunosorbent assay (ELISA) and Fluorescence-activated cell sorting (FACS) assay described later.

As a result, anti-human erbB3 monoclonal antibody-producing hybridomas 1126, 1153, 920104, and 12511 were established.

Example 3

Determining Binding Domain of Anti-erbB3 Antibody

The binding domain of the anti-human erbB3 monoclonal antibody obtained by the present invention was determined by binding ELISA for GST fusion protein obtained by fusing the extracellular domain of erbB3 with GST.

anti-Glutathione-Transferase-Schistsoma-japonicum (Goat) (manufactured by Rockland Immunochemicals Inc., ca. No. 16979) (hereinbelow, described as "anti-GST") prepared at 1 μg/mL by using a 50 mM carbonate buffer (pH 9) (hereinbelow, described as a "coating buffer") was added to Maxisorp plate (NUNC; ca. No. 442404) at 50 μL/well and immobilized by incubation at 37° C. for an hour (or 4° C., ON).

After the buffer was discarded, a blocking reagent (Super-Block® Blocking Buffer, manufactured by PIERCE) was added to the respective wells at 250 μL to 300 μL/well, followed by incubation at room temperature for 5 to 10 minutes for blocking After the blocking reagent was discarded, the herbB3-GST fusion protein, the merbB3-GST fusion protein, the hD1/mD234 fusion protein, the hD12/mD34 fusion protein, and the hD123/mD4 fusion protein which were diluted at 5 μg/mL with Tris-buffered saline (hereinbelow, described as an "assay diluent") containing 10% Block Ace® (manufactured by Dainippon Sumitomo Pharma Co., Ltd.) and 0.1% Tween 20 were added respectively to the plates of the respective antigens at 50 μL/well, and immobilized by incubation at room temperature for an hour.

The antigen solution was discarded, and the plate was washed three times with a Tris-buffered saline containing 0.1% Tween 20 (hereinbelow, described as a "washing buffer"). Thereafter, an immunized serum sample (diluted 100-fold, 1000-fold, and 10000-fold of the final concentration) and a mouse serum sample (diluted 100-fold, 1000-fold, and 10000-fold of the final concentration) diluted with the assay diluent, anti-c-erbB3 mouse monoclonal antibody (Ab-4) (manufactured by Calbiochem, Cat. No. OP119) (final concentration of 1 ng/mL to 1000 ng/mL) as a positive control, and mouse IgG1κ isotype control (manufactured by Southern Biotech, Cat. No. 010201) (final concentration of 1 ng/mL to 1000 ng/mL) as a negative control were added to the plate at 50 μL/well. After addition of the first antibody, the plate was incubated at room temperature for 30 minutes.

After the plate was washed three times with the washing buffer, HRP-labeled goat anti-mouse IgG antibody (manufactured by Southern Biotech, Cat. No. 1030-05), HRP-labeled goat anti-mouse IgG antibody (manufactured by Caltag Laboratories, Cat. No. M30107), and HRP-labeled goat anti-mouse IgM antibody (manufactured by Southern Biotech, Cat. No. 1020-05) which were diluted with the assay diluent were added at 50 μL/well and bound at room temperature for 30 minutes.

After the plate was washed four times with the washing buffer, a 3,3',5,5'-tetramethylbenzidine (TMB) chromogenic substrate solution (manufactured by DAKO) was added thereto at 50 μL/well, followed by incubation at room temperature in a dark place, thereby developing color (for about 3 minutes). While the state of color development progress was being observed, 0.5M sulfuric acid (50 μL/well) was added thereto to stop the reaction.

An absorbance at a wavelength of 450 nm (reference wavelength of 570 nm) was measured using a microplate reader (MTP-300; manufactured by CORONA ELECTRIC Co., Ltd.). As results of binding ELISA, reactivity of the respective clones with each antigen are shown in Table 1.

TABLE 1

| Clone name | herbB3 | merbB3 | hD1/ mD234 | hD12/ mD34 | hD123/mD4 | Binding domain of antigen |
|---|---|---|---|---|---|---|
| 1153 | + | − | + | + | + | 1 |
| 920104 | + | − | − | − | + | 3 |
| 1126 | + | − | − | − | − | 4 |
| 12511 | + | + | + | + | + | N.D.* |

*Since 12511 bound with all antigen proteins, binding domain was not clarified by the present assay.

As shown in Table 1, it was clarified that the anti-human erbB3 monoclonal antibody 1153 of the present invention recognizes the domain 1 in the extracellular domain of erbB3, the anti-human erbB3 monoclonal antibody 920104 recognizes the domain 3, and the anti-human erbB3 monoclonal antibody 1126 recognizes the domain 4. On the other hand, it was clarified that the anti-human erbB3 monoclonal antibody 12511 of the present invention binds with both the human erbB3 and the mouse erbB3.

Example 4

Preparation of Recombinant Antibody 1. cDNA Cloning of Respective Antibody Genes and Preparation of Mouse/Human Chimera Monoclonal Antibody Expression Vector A hybridoma was cultured in a serum-containing DMEM and centrifuged (at 1500 rpm for 3 minutes) to collect cells, and then 5 mL of ISOGEN® (manufactured by NIPPON GENE CO., LTD.) was added thereto, thereby extracting total RNA according to the protocol attached. By using 1 μL of the total RNA as a template, a first strand cDNA was prepared according to the protocol attached to SMART RACE® cDNA amplification kit (manufactured by Clontech), and by using 2.5 μL of the prepared cDNA as a template, a light chain variable region (hereinbelow, described as "VL") and a heavy chain variable region (hereinbelow, described as "VH") were amplified using KOD Plus® DNA polymerase (manufactured by TOYOBO Co., Ltd.).

For amplifying VL, PCR was performed for 5 cycles consisting of 94° C. for 5 seconds and 72° C. for 3 minutes, and then performed again for 5 cycles consisting of 94° C. for 5 seconds, 70° C. for 10 seconds and 72° C. for 3 minutes, and further performed for 25 cycles consisting of 94° C. for 5 seconds, 68° C. for 10 seconds and 72° C. for 3 minutes, by using UMP (included in SMART RACE cDNA amplification Kit) and mk-RvP1 (SEQ ID NO:31) primer.

Thereafter, by using 1 μL of the reaction solution diluted 5-fold as a template, PCR was performed for 25 to 30 cycles consisting of 94° C. for 15 seconds, 60° C. for 30 seconds and 68° C. for 1 minute, by using NUMP (included in SMART RACE® cDNA amplification Kit) and mk-RvP2 primer (SEQ ID NO:32).

For amplifying VH, PCR using UMP attached to the kit and mH-Rv1 primer (SEQ ID NO:33) and PCR using NUMP attached to the kit and mH-Rv2 primer (SEQ ID NO:34) were performed in the same manner as described above.

The PCR products of the amplified VH and VL were subjected to 2% agarose gel electrophoresis and purified using QIAquick® gel extraction kit (manufactured by QIAGEN). The purified PCR products were ligated to pCR4Blunt-TOPO® vector (manufactured by Invitrogen) and subcloned according to the attached instruction. Subsequently, nucleotide sequences were determined using a T3 primer and a T7 primer included in the kit, thereby designing primers specific to the respective clones.

The process of preparing chimeric antibody expression vectors of the respective clones is shown below. All PCR were performed using KOD Plus® DNA polymerase (manufactured by TOYOBO Co., Ltd.). In addition, in the sequence analysis performed after the insertion of expression vectors, a heavy chain sequence was confirmed using SEQ4618 primer (SEQ ID NO:35), and a light chain sequence was confirmed using SEQ1783 primer (SEQ ID NO:36).

(1) Preparation of 1153 Antibody Expression Vector

By using the subcloned 1153 heavy chain gene as a template, PCR was performed for 30 cycles consisting of 94° C. for 15 seconds, 55° C. for 30 seconds and 68° C. for 1 minute, by using 1153Hc-SalIU (SEQ ID NO:37) and 1153Hc-NheIL (SEQ ID NO:38). The reaction solution was subjected to 2% agarose gel electrophoresis, and about 450 bp of a fragment was purified using QIAquick® gel extraction kit (manufactured by QIAGEN).

The 1153VH amplification fragment was digested with restriction enzymes SalI and NheI, and introduced into sites of SalI and NheI of N5KG1-Val Lark vector (manufactured by Biogen-IDEC) comprising a DNA fragment encoding the H-chain constant region and the L-chain constant region of human IgG1. The DNA sequences of the insertion sites were confirmed, thereby preparing N5KG1/1153H vector having DNA of VH of the 1153 antibody.

By using the subcloned 1153 light chain gene as a template, PCR was performed in the same manner as in the case of VH by using 1153Lc-BglII primer (SEQ ID NO:39) and 1153Lc-BsiWI primer (SEQ ID NO:40), thereby purifying about 400 bp of a fragment. The extracted 1153VL amplification fragment was digested with restriction enzymes BglII and BsiWI, and inserted into the site of BglII and BsiWI of N5KG1/1153VH vector. The DNA sequences of the insertion sites were confirmed, thereby preparing an N5KG1/1153 expression vector comprising DNA of VH and VL of the 1153 antibody.

(2) Preparation of 920104 Antibody Expression Vector

Regarding a 920104 antibody expression vector, an N5KG1/920104 expression vector having DNA of VH and VL of the 920104 antibody was prepared in the same manner as in the section 1-(1), except that a 920104Hc-SalIU primer (SEQ ID NO:41) and a 920104Hc-NheIL primer (SEQ ID NO:42) were used for amplifying VH, and a 920104Lc-BglII primer (SEQ ID NO:43) and a 920104Lc-BsiWI primer (SEQ ID NO:44) were used for amplifying VL.

(3) Preparation of 1126 Antibody Expression Vector

Regarding a 1126 antibody expression vector, an N5KG1/1126 expression vector comprising DNA of VH and VL of the 1126 antibody was prepared in the same manner as in the section 1-(1), except that a 1126Hc-SalIU primer (SEQ ID NO:45) and a 1126Hc-NheIL primer (SEQ ID NO:46) were used for amplifying VH, a 1126Lc-PmeIU primer (SEQ ID NO:47) and a 1126Lc-BsiWI primer (SEQ ID NO:48) were used for amplifying VL, and PmeI was used as a restriction enzyme of VL.

(4) Preparation of 12511 Antibody Expression Vector

Regarding a 12511 antibody expression vector, an N5KG1/12511 expression vector comprising DNA of VH and VL of the 12511 antibody was prepared in the same manner as in the section 1-(1), except that a 12511Lc-SalIU primer (SEQ ID NO:49) and a 12511Lc-NheIL primer (SEQ ID NO:50) were used for amplifying VH, a 12511Lc-BglIIU primer (SEQ ID NO:51) and a 12511Lc-BsiWI primer (SEQ ID NO:52) were used for amplifying VL.

The nucleotide sequence of DNA comprised in the antibody expression vectors described in the above sections (1) to (4), amino acid sequences encoded by the nucleotide sequences, and amino acid sequences of antibodies are shown below.

The nucleotide sequences of DNA encoding VH and VL of the 1153 antibody are represented by SEQ ID NO:53 and SEQ ID NO:55, and the amino acid sequences encoded by the nucleotide sequences are represented by SEQ ID NOS:54 and 56. In addition, the amino acid sequences of VH and VL of the secreted 1153 antibody are represented by SEQ ID NOS:57 and 58. The amino acid sequences of CDRs 1 to 3 of VH and CDRs 1 to 3 of VL are represented by SEQ ID NOS:59 to 61 and SEQ ID NOS:62 to 64 respectively.

The nucleotide sequences of DNA encoding VH and VL of the 920104 antibody are represented by SEQ ID NO:65 and SEQ ID NO:67, and the amino acid sequences encoded by the nucleotide sequences are represented by SEQ ID NOS:66 and 68. In addition, the amino acid sequences of VH and VL of the secreted 920104 antibody are represented by SEQ ID NOS: 69 and 70. The amino acid sequences of CDRs 1 to 3 of VH and CDRs 1 to 3 of VL are represented by SEQ ID NOS:71 to 73 and SEQ ID NOS:74 to 76 respectively.

The nucleotide sequences of DNA encoding VH and VL of the 1126 antibody are represented by SEQ ID NO:77 and SEQ ID NO:79, and the amino acid sequences encoded by the nucleotide sequences are represented by SEQ ID NOS:78 and 80. In addition, the amino acid sequences of VH and VL of the secreted 1126 antibody are represented by SEQ ID NOS:81 and 82. The amino acid sequences of CDRs 1 to 3 of VH and CDRs 1 to 3 of VL are represented by SEQ ID NOS:83 to 85 and SEQ ID NOS:86 to 88 respectively.

The nucleotide sequences of DNA encoding VH and VL of the 12511 antibody are represented by SEQ ID NO:89 and SEQ ID NO:91, and the amino acid sequences encoded by the nucleotide sequences are represented by SEQ ID NOS:90 and 92. In addition, the amino acid sequences of VH and VL of the secreted 12511 antibody are represented by SEQ ID NOS:93 and 94. The amino acid sequences of CDRs 1 to 3 of VH and CDRs 1 to 3 of VL are represented by SEQ ID NOS:95 to 97 and SEQ ID NOS:98 to 100 respectively.

(5) Preparation of Control Antibody Expression Vector

As a positive control antibody, the anti-human erbB3 human antibody U1-59 disclosed in WO 2007/077028 (Patent Document 3) was used. cDNA encoding the amino acid sequences represented by SEQ ID NOS:70 and 72 disclosed in WO 2007/077028 (Patent Document 3) was fully synthesized (TAKARA BIO INC) and inserted into the N5GK1 expression vector (manufactured by Biogen-IDEC), thereby preparing an expression vector of the anti-human erbB3 human antibody U1-59.

As a negative control antibody, the anti-dinitrophenylhydrazine (DNP) antibody disclosed in Motoki K et al., Clin. Cancer Res. 11, 3126-3135, 2005 was used.

2. Expression and Purification of Recombinant Antibody

The recombinant antibody expression vectors prepared in Example 4-1 were introduced respectively into FreeStyle 293F cell according to the attached instruction, by using FreeStyle293® Expression Kit (manufactured by Invitrogen), followed by culturing for several days. The obtained supernatant was provided to a 0.2 μm filter (manufactured by Millipore Corporation), thereby removing waste substances such as FreeStyle 293 cell.

Thereafter, the filtered culture supernatant was added to a Protein A resin (MabSelect®, manufactured by Amersham Pharmacia Biotech), thereby performing affinity purification of the recombinant antibody. A phosphate buffer was used as a wash solution, and a 20 mM sodium citrate buffer (pH 3) was used as an elution buffer.

A 50 mM sodium phosphate buffer (pH 7.0) was added to the eluted fractions, thereby adjusting pH to around 6.0. The prepared antibody solution was substituted with a phosphate buffer by using a dialysis membrane (10000 cut, manufactured by Spectrum Laboratories, Ltd), and sterilized by being filtered through a membrane filter MILLEX-GV (manufactured by Millipore Corporation) having a pore size of 0.22 μm, thereby preparing a purified anti-human erbB3 recombinant antibodies. The concentration of the purified antibody was measured using an absorbance at 280 nm and calculated by setting 1 mg/mL to be a 1.45 Optimal density.

Example 5

Inhibitory Effect of Anti-erbB3 Antibody on Heregulin-Dependent Phosphorylation of erbB3

$5 \times 10^4$ cells of a human squamous carcinoma cell line A431 were suspended in 10% FBS-containing RPMI1640 medium (manufactured by Invitrogen) (hereinbelow, described as "serum-containing RPMI"), seeded to a 24-well plate at 1 mL/well, and cultured overnight under culture conditions of 37° C. and 6.5% $CO_2$.

After the culture supernatant was removed, the plate was washed once with a serum-free RPMI1640 medium (manufactured by Invitrogen) (hereinbelow, described as "RPMI"), and then RPMI was added thereto at 1 mL/well, followed by culturing overnight. After the culture supernatant was removed, the plate was washed once with RPMI, the respective antibodies prepared at 50 μg/mL by using RPMI were then added thereto at 250 μL/well, and the cells were cultured at 37° C. for 30 minutes in the presence of 6.5% $CO_2$.

Subsequently, 200 ng/mL NRG1-α/HRG1-αEGF Domain (manufactured by R&D Systems, Inc., 296-HR-050/CF) or 40 ng/mL NRG1-β1/HRG1-β1 Extracellular Domain (manufactured by R&D Systems, Inc., 377-HB-050/CF) which was diluted with RPMI was added thereto respectively at 250 μL/well, followed by culturing at 37° C. for 10 minutes in the presence of 6.5% $CO_2$.

After culturing, the supernatant was removed on an ice, and the plate was washed once with RPMI. Thereafter, Takara 39000 Lane Marker Reducing Sample Buffer (manufactured by TAKARA BIO INC) was added thereto at 100 μL/well, thereby recovering cells. Thereafter, DNA was crushed and heated at 95° C. for 5 minutes, thereby obtaining a sample for Western blotting.

Thereafter, SDS-PAGE was performed at a rate of 30 mA/gel for 60 minutes, and proteins were transferred to a PVDF membrane at a rate of 30 mA/gel for 90 minutes. In the PVDF membrane to which proteins were transferred, Block Ace® (manufactured by Dainippon Sumitomo Pharma Co., Ltd.) was used for detecting erbB3, phosphorylated erbB3, and Akt, and Tris-buffered saline (hereinbelow, described as "5% BSA-tTBS") containing 5% BSA and 0.1% tween20 was used as a blocking buffer, so as to perform blocking at room temperature for an hour respectively.

After the blocking buffer was removed, an anti-erbB3 antibody (manufactured by Santa Cruz Biotechnology, Inc) prepared using 5% BSA-tTBS, an anti-phosphorylated erbB3 antibody (manufactured by Cell Signaling Technology), an anti-AKT antibody (manufactured by Cell Signaling Technology), and an anti-phosphorylated AKT antibody (manufactured by Promega Corporation) were added thereto, followed by incubation overnight at 4° C.

The PVDF membrane was washed with Tris-buffered saline (hereinbelow, described as "TTBS") containing 0.1% Tween 20, and then anti-rabbit immunoglobulin goat polyclonal antibody/HRP (manufactured by DAKO) was added thereto, followed by incubation at room temperature for an hour. After being washed with TTBS, the PVDF membrane was reacted with ECL® Plus Western Blotting Detection Reagents (manufactured by Amersham Pharmacia Biotech), and fluorescence was detected using a lumino-image analyzer (LAS-1000, FUJIFILM Corporation).

As a result, as shown in FIG. 1, both the heregulin α and β induced phosphorylation of erbB3 of the human squamous carcinoma cell line A431 and Akt phosphorylation of downstream signal. In addition, both the anti-human erbB3 human antibody U1-59 and the anti-human erbB3 recombinant antibodies of the present invention inhibited heregulin α- and β-dependent phosphorylation of erbB3 and inhibited Akt phosphorylation of downstream signal.

Example 6

Inhibition of erbB3 Phosphorylation Depending on Amphiregulin, Betacellulin, Epiregulin, TGF-α, EGF and HB-EGF by Anti-erbB3 Antibody The human squamous carcinoma cell line A431 was pretreated in the same manner as in Example 5, and then the respective ligands were added thereto. 100 ng/mL amphiregulin (R&D 262-AR/CF), 100 ng/mL betacellulin (R&D 261-CF/CF), 100 ng/mL epiregulin (R&D 1195-EP/CF), 200 ng/mL HB-EGF (R&D 259-HE/CF), and 200 ng/mL TGF-α (R&D 239-A) which were diluted with serum-free RPMI were added respectively to media at 250 μL/well, followed by culturing at 37° C. for 10 minutes in the presence of 6.5% $CO_2$. Subsequently, the total amount of the erbB3 protein and the amount of the phosphorylated erbB3 protein were analyzed in the same manner as in Example 5.

Figure 2:
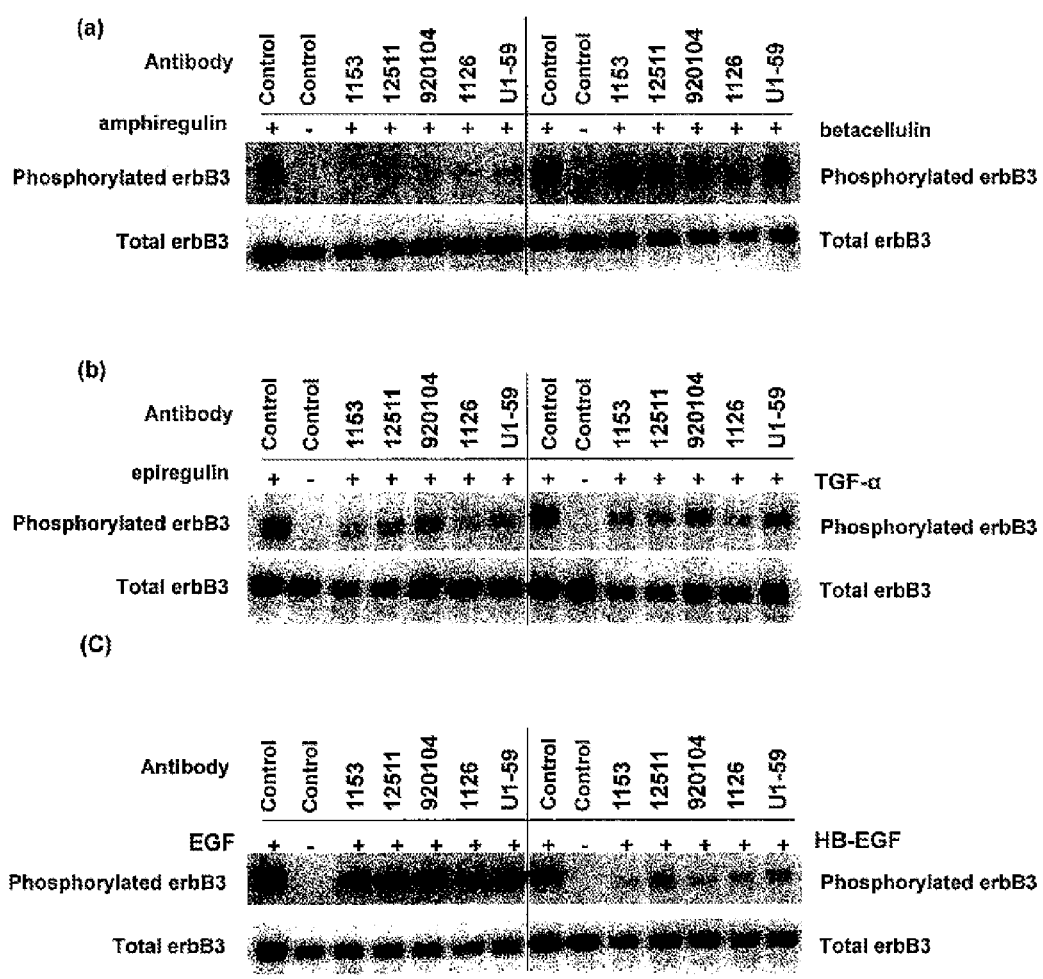
FIGS. 2(a) and (b) show the inhibitory effect of the anti-human erbB3 antibody on EGF-like ligand-dependent phosphorylation of erbB3 in the human squamous carcinoma cell line A431.
FIG. 2(b) shows epiregulin- or TGFα-dependent phosphorylation of erbB3.
FIG. 2(c) shows EGF- or HB-EGF-dependent phosphorylation of erbB3. In the respective drawings, the upper portion shows phosphorylated erbB3, and the low portion shows total erbB3 proteins. In addition, the uppermost portion of the respective drawings shows the antibodies used.

As a result, as shown in FIG. 2, all of the EGF-like ligands other than heregulin including amphiregulin, betacellulin, epiregulin, TGF-α, EGF and HB-EGF also phosphorylated erbB3 of the human squamous carcinoma cell line A431.

All of the anti-human erbB3 human antibody U1-59 and the anti-human erbB3 recombinant antibodies 1153, 920104, 1126, and 12511 of the present invention inhibited all the EGF-like ligand-dependent phosphorylation of erbB3. Particularly, the anti-human erbB3 recombinant antibody 1126 of the present invention most strongly inhibited phosphorylation of erbB3 depending on all ligands.

Example 7

Inhibition of erbB3 Phosphorylation Depending on Epiregulin, TGF-α, HB-EGF and Heregulin by Anti-erbB3 Antibody $1 \times 10^5$ cells of a human breast cancer cell line T47D were suspended in serum-containing RPMI, seeded to a 24-well plate at 1 mL/well, and cultured overnight under culture conditions of 37° C. and 6.5% $CO_2$. The culture supernatant was removed, the plate was washed once with RPMI, and then RPMI was added thereto at 1 mL/well, followed by culturing overnight. Thereafter, culture supernatant was removed, the plate was washed once with RPMI, and then the respective anti-human erbB3 antibodies prepared at 50 μg/mL by using RPMI were added thereto at 250 μL/well, followed by cell culturing at 37° C. for 30 minutes in the presence of 6.5% $CO_2$.

Subsequently, 40 ng/mL NRG1-β/HRG1-β Extracellular Domain (manufactured by R&D Systems, Inc., 377-HB/CF), 100 ng/mL epiregulin (manufactured by R&D Systems Inc., 1195-EP/CF), 200 ng/mL HB-EGF (manufactured by R&D Systems Inc., 259-HE/CF), and 200 ng/mL TGF-α (manufactured by R&D Systems Inc., 239-A) which were diluted with RPMI were added thereto respectively at 250 μL/well, followed by culturing at 37° C. for 10 minutes in the presence of 6.5% $CO_2$.

After culturing, the supernatant was removed on an ice, and the plate was washed once with RPMI. Thereafter, Takara 39000 Lane Marker Reducing Sample Buffer (manufactured by TAKARA BIO INC) was added thereto at 100 μL/well, thereby recovering cells. Thereafter, DNA was crushed and heated at 95° C. for 5 minutes, thereby obtaining a sample for Western blotting. Subsequently, the total amount of the erbB3 protein and the amount of the phosphorylated erbB3 protein were analyzed in the same manner as in Example 5.

Figure 3:
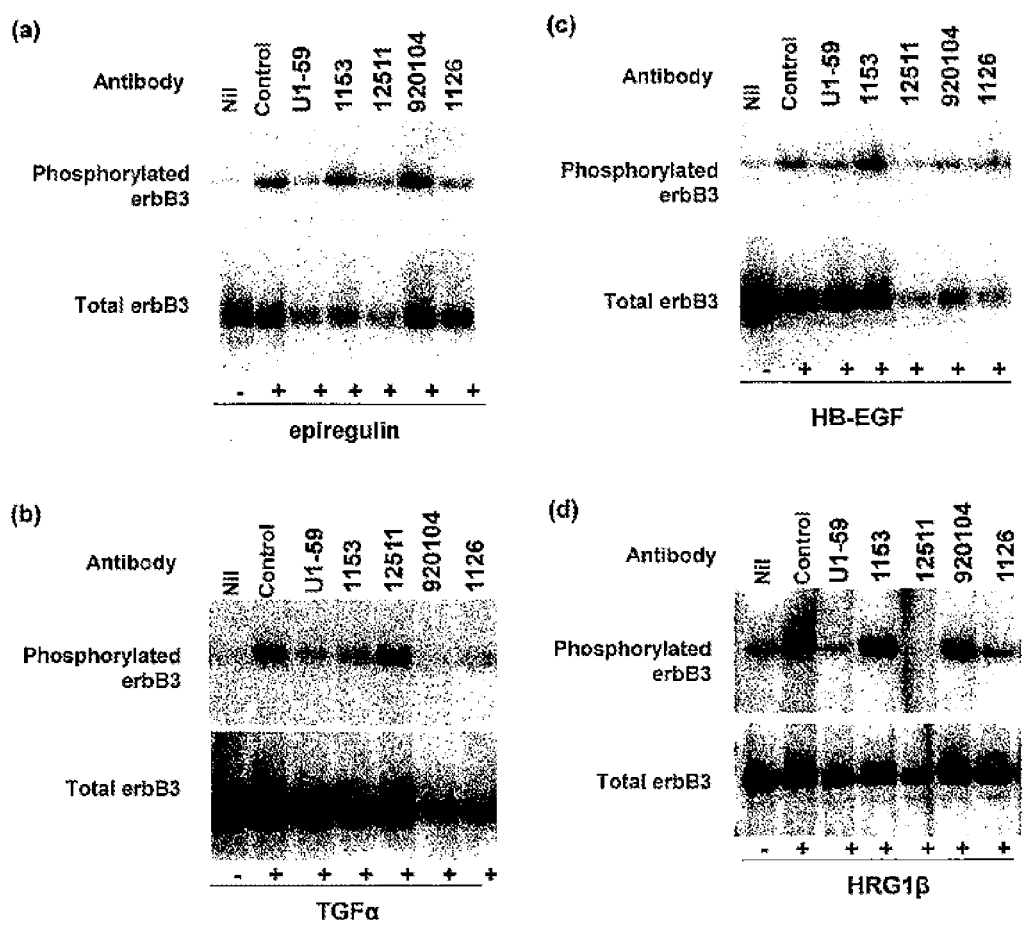
FIGS. 3(a) and (b) show the inhibitory effect of the anti-human erbB3 antibody on EGF-like ligand-dependent phosphorylation of erbB3 in a human breast cancer cell line T47D.
FIG. 3(b) shows TGFα-dependent phosphorylation of erbB3.
FIG. 3(c) shows HB-EGF-dependent phosphorylation of erbB3.
FIG. 3(d) shows heregulin β-dependent phosphorylation of erbB3. In the respective drawings, the upper portion shows phosphorylated erbB3, and the lower portion shows total erbB3 proteins. In addition, the uppermost portion of the respective drawings shows the antibodies used.

As a result, as shown in FIG. 3, the anti-human erbB3 recombinant antibody 1126 of the present invention further inhibited epiregulin-, TGF-α-, HB-EGF-, and HRG1β-dependent phosphorylation of erbB3 of the human breast cancer cell T47D, compared to the negative control antibody. In addition, the anti-human erbB3 recombinant antibody 1126 of the present invention showed higher inhibitory effect against TGF-α- and HB-EGF-dependent phosphorylation of erbB3 of the human breast cancer cell T47D, compared to the positive control antibody.

The anti-human erbB3 recombinant antibody 12511 of the present invention completely suppressed HRG1β- and HB-EGF-dependent phosphorylation of erbB3 in the human breast cancer cell T47D, compared to the positive control antibody (U1-59).

Further the anti-human erbB3 recombinant antibody 920104 of the present invention showed higher inhibitory effect against TGF-α- and HB-EGF-dependent phosphorylation of erbB3 in the human breast cancer cell T47D, compared to the positive control antibody (U1-59).

The anti-human erbB3 recombinant antibody 1153 of the present invention further inhibited TGF-α-dependent phosphorylation of erbB3 in the human breast cancer cell T47D, compared to the negative control antibody.

Example 8

In-Vivo Drug Efficacy Evaluation of Anti-erbB3 Antibody 6-week-old female BALB/cA Jcl-nu/nu (manufactured by CLEA Japan, Inc.) were prepared and bred preliminarily for a week. The human breast cancer line T47D which was cultured using 10% RPMI medium under conditions of 37° C. and 6.5% $CO_2$ was prepared as a cell suspension at $1 \times 10^8$ cells/mL by using RPMI.

The prepared cell suspension was subcutaneously grafted to 72 mice at 100 μL/head. After engraftment of T47D to the mice was confirmed, mice were selected at a point in time when the tumor volume (long diameter×short diameter×short diameter/2) reached 50 $mm^3$ to 100 $mm^3$, such that the average of tumor volume became equivalent among the mice, and the mice were grouped into 6 groups at 6 mice/group.

1 mg/mL anti-human erbB3 recombinant antibodies 1153, 12511, 920104, and 1126, 1 mg/mL anti-human erbB3 human antibody U1-59, and anti-DNP antibody as a negative control, diluted with PBS, were started to be intraperitoneally administered to the mice at 200 μL/head from the point of grouping. The antibodies were administered 8 times in total by twice a week.

Figure 4:
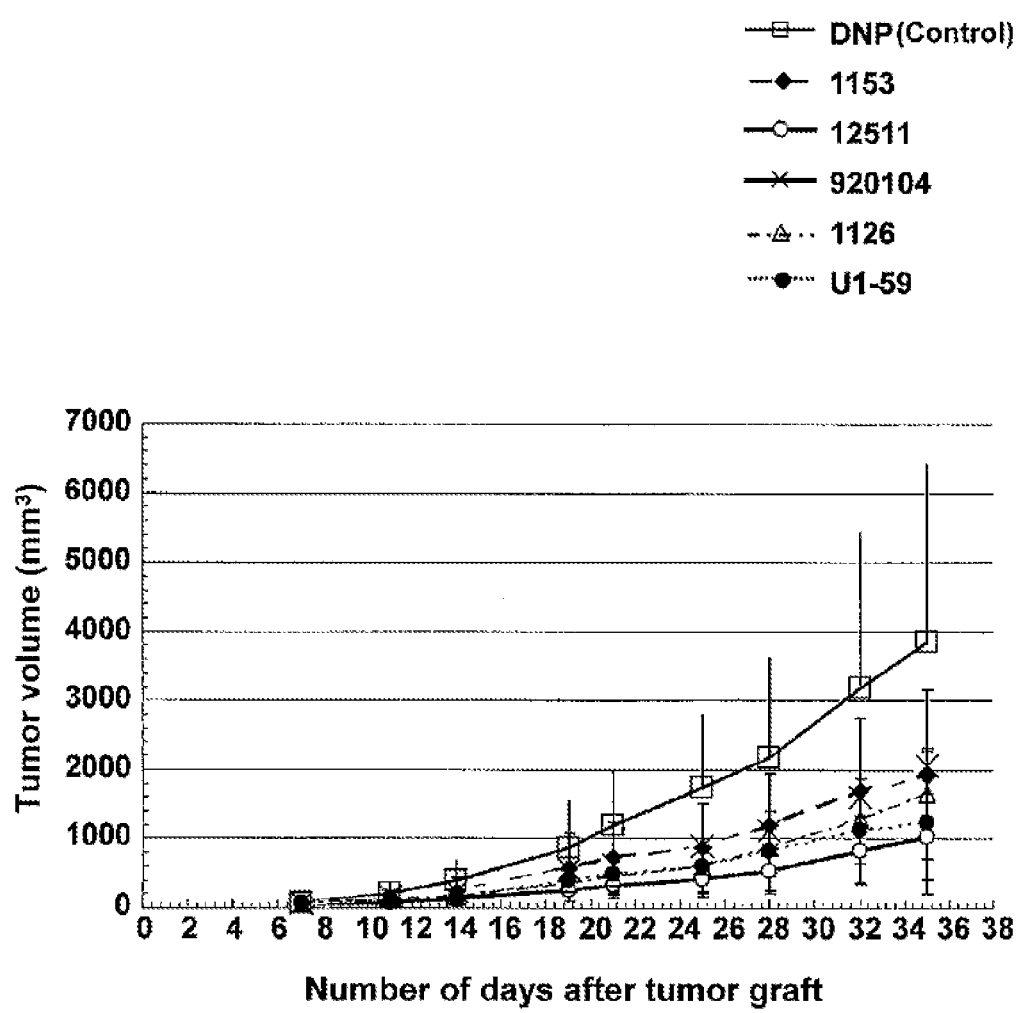
FIG. 4 shows the antitumor effect of the anti-human erbB3 antibody in a human breast cancer cell line T47D-grafted mouse model. The abscissa shows the number of days after the tumor grafting, and the ordinate shows the tumor volume. "□" indicates an anti-DNP antibody as a control, "◆" indicates a 1153 antibody, "○" indicates a 12511 antibody, "X" indicates a 920104 antibody, "Δ" indicates a 1126 antibody, and "●" indicates a U1-59 antibody.

As a result, as shown in FIG. 4, both the anti-human erbB3 human antibody U1-59 and the anti-human erbB3 recombinant antibodies further inhibited the tumor growth of the human breast cancer cell line T47D, compared to the anti-DNP antibody as a control.

Example 9

In-Vivo Drug Efficacy Evaluation Using Plural Anti-erbB3 Antibodies

Xenograft mice to which the human breast cancer cell line T47D was subcutaneously grafted or xenograft mice to which the human squamous carcinoma cell line A431 was subcutaneously grafted were prepared in the same manner as in Example 8. At a point in time when the tumor mass reached 100 $mm^3$ to 200 $mm^3$, mice were selected such that the average of the tumor volume become equivalent among the mice, and the mice were grouped into 4 groups at 6 mice/group.

Solutions of 2 mg/mL anti-human erbB3 recombinant antibodies 1153, 12511, 1126, and anti-DNP antibody were prepared using PBS. The solutions of 1153, 12511, and 1126 antibodies were mixed with each other at a ratio of 1:1, thereby preparing a 1153+12511 combination antibody solution (combination antibody solution containing 1153 and 12511 antibodies), a 1153+1126 combination antibody solution (combination antibody solution containing 1153 and 1126 antibodies), and a 12511+1126 combination antibody solution (combination antibody solution containing 12511 and 1126 antibodies). The antibodies were intraperitoneally administered at 100 μL/head from the point of grouping. The antibodies were administered 10 times in total by twice a week.

Figure 5:
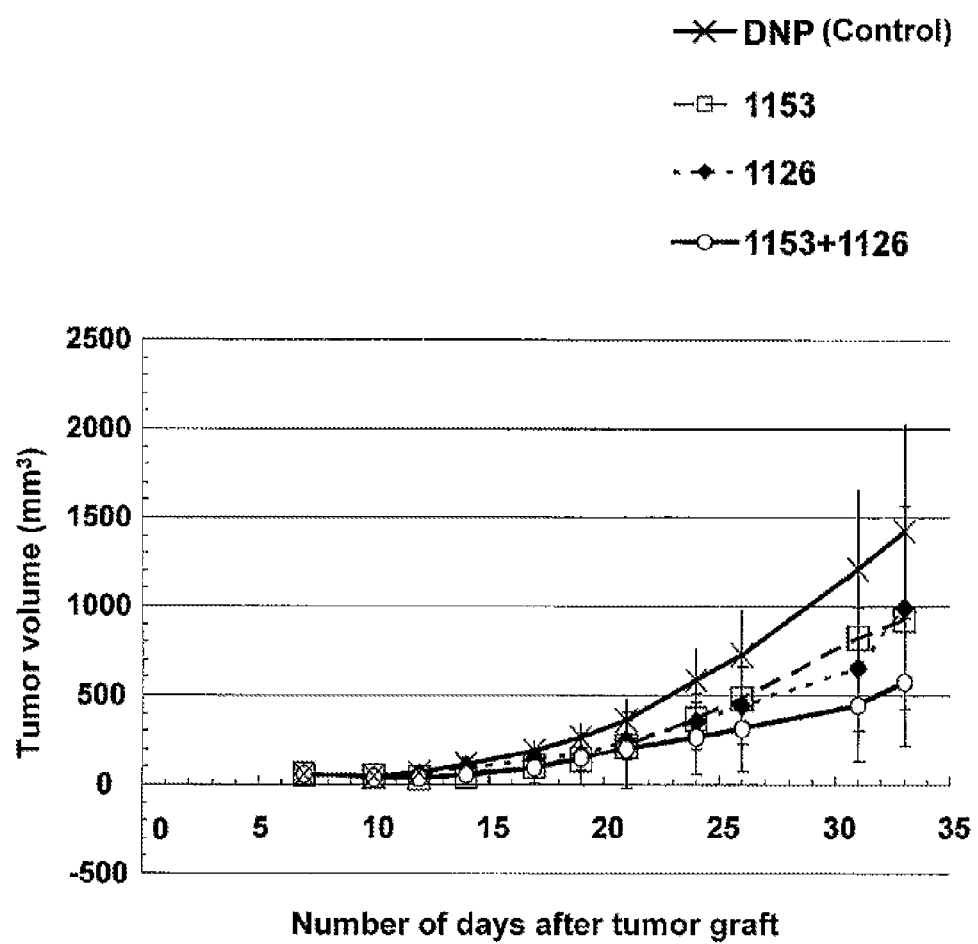
FIG. 5 shows the combinational effect of the anti-human erbB3 antibody in the human breast cancer cell line T47D-grafted mouse model. "X" indicates an anti-DNP antibody as a control, "□" indicates a 1153 antibody, "◆" indicates a 1126 antibody, and "○" indicates a 1153+1126 combination antibody (combination antibody of a 1153 antibody and a 1126 antibody). The abscissa shows the number of days after the tumor grafting, and the ordinate shows the tumor volume.

As a result, as shown in FIG. 5, the anti-human erbB3 recombinant antibodies 1153 and 1126 further inhibited the tumor growth of the human breast cancer T47D, compared to the anti-DNP antibody as a control. In addition, the combined administration of 1153 and 1126 antibodies more strongly inhibited the tumor growth, compared to a case where the 1153 or 1126 antibody was administered alone.

Figure 6:
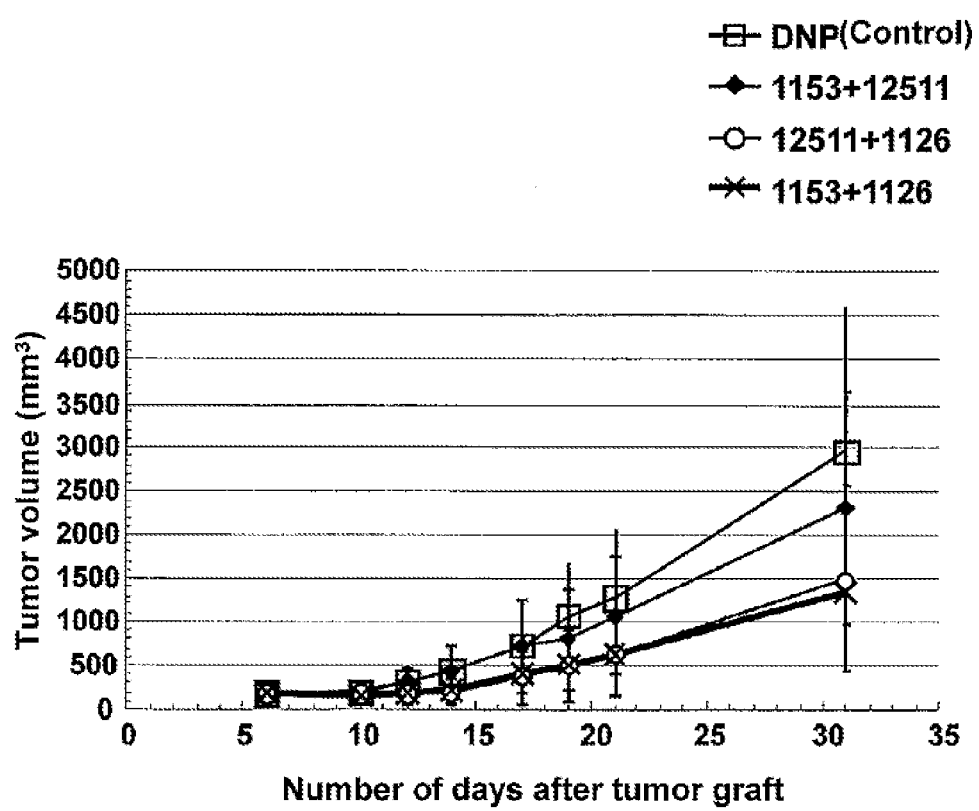
FIG. 6 shows combinational effect of the anti-human erbB3 antibodies in the human squamous carcinoma cell line A431-grafted mouse model. "□" indicates an anti-DNP antibody as a control, "◆" indicates a 1153+1251 combination antibody (combination antibody of a 1153 antibody and a 12511 antibody), "○" indicates a 12511+1126 combination antibody (combination antibody of a 12511 antibody and a 1126 antibody), and "X" indicates a 1153+1126 combination antibody (combination antibody of a 1153 antibody and a 1126 antibody). The abscissa shows the number of days after the tumor grafting, and the ordinate shows the tumor volume.

In addition, as shown in FIG. 6, all of the antibody combinations including combination of the 1153 and 12511 antibodies, the combination of the 12511 and 1126 antibodies, and the combination of the 1153 and 1126 antibodies further inhibited cell growth of the human squamous carcinoma cell A431, compared to the anti-DNP antibody as a control. Moreover, the combined administration of the 12511 and 1126 antibodies and the 1153 and 1126 antibodies more strongly inhibited tumor growth, compared to the combined administration of 1153 and 12511 antibodies.

From the above results, it is clarified that when the antibody 1126 recognizing the domain 4 in the extracellular domain of erbB3 is administered in combination with the antibody 1153 or 12511 binding to the extracellular domain of erbB3 other than the domain 4, antitumor activity is enhanced.

The present application is a patent application to which researches on "Project of Development of Technologies to Create New Functional Antibody", "Development of Technologies to Create New Functional Antibody/Development of Technologies to Create Systematic High-Specificity Antibody/Development of Technologies to Create Oligoclonal Antibody" sponsored by New Energy and Industrial Technology Development Organization on 2006, and Industrial Technology Enhancement Act, Article 19 are applied.

Though the present invention has been described in detail by using specific embodiments, a person skilled in the art knows clearly that the various changes and modifications can be made within a range which does not depart from the spirit and scope of the present invention. The present application is based on U.S. provisional application (61/498,732) filed Jun. 20, 2011, the entire content of which is incorporated herein as reference.

FREE TEXT OF SEQUENCE LISTING

SEQ ID NO:3: The amino acid sequence of extracellular domain of human erbB3
SEQ ID NO:6: The amino acid sequence of extracellular domain of mouse erbB3
SEQ ID NO:7: The nucleotide sequence of rherbB3 primer 1
SEQ ID NO:8: The nucleotide sequence of rherbB3 primer 2
SEQ ID NO:9: The nucleotide sequence of rherbB3-GST primer 1
SEQ ID NO:10: The nucleotide sequence of rherbB3-GST primer 2
SEQ ID NO:11: The nucleotide sequence of mouse erbB3-GST primer 1
SEQ ID NO:12: The nucleotide sequence of mouse erbB3-GST primer 2
SEQ ID NO:13: The nucleotide sequence of hD1/mD234 primer 1
SEQ ID NO:14: The nucleotide sequence of hD1/mD234 primer 2
SEQ ID NO:15: The nucleotide sequence of hD1/mD234 primer 3
SEQ ID NO:16: The nucleotide sequence of hD1/mD234 primer 4
SEQ ID NO:17: The nucleotide sequence of hD1/mD234 primer 5
SEQ ID NO:18: The nucleotide sequence of hD1/mD234 primer 6
SEQ ID NO:19: The nucleotide sequence of hD12/mD34 primer 1
SEQ ID NO:20: The nucleotide sequence of hD12/mD34 primer 2
SEQ ID NO:21: The nucleotide sequence of hD12/mD34 primer 3
SEQ ID NO:22: The nucleotide sequence of hD12/mD34 primer 4
SEQ ID NO:23: The nucleotide sequence of hD12/mD34 primer 5
SEQ ID NO:24: The nucleotide sequence of hD12/mD34 primer 6
SEQ ID NO:25: The nucleotide sequence of hD123/mD4 primer 1
SEQ ID NO:26: The nucleotide sequence of hD123/mD4 primer 2
SEQ ID NO:27: The nucleotide sequence of hD123/mD4 primer 3
SEQ ID NO:28: The nucleotide sequence of hD123/mD4 primer 4
SEQ ID NO:29: The nucleotide sequence of hD123/mD4 primer 5
SEQ ID NO:30: The nucleotide sequence of hD123/mD4 primer 6
SEQ ID NO:31: The nucleotide sequence of mkRvP1 primer
SEQ ID NO:32: The nucleotide sequence of mkRvP2 primer
SEQ ID NO:33: The nucleotide sequence of mH-Rv1 primer
SEQ ID NO:34: The nucleotide sequence of mH-Rv2 primer
SEQ ID NO:35: The nucleotide sequence of SEQ4618 primer
SEQ ID NO:36: The nucleotide sequence of SEQ1783 primer
SEQ ID NO:37: The nucleotide sequence of 1153Hc-SalIU primer
SEQ ID NO:38: The nucleotide sequence of 1153Hc-NheIL primer
SEQ ID NO:39: The nucleotide sequence of 1153Lc-BglII primer
SEQ ID NO:40: The nucleotide sequence of 1153Lc-BsiWI primer
SEQ ID NO:41: The nucleotide sequence of 920104Hc-SalIU primer
SEQ ID NO:42: The nucleotide sequence of 920104Hc-NheIL primer
SEQ ID NO:43: The nucleotide sequence of 920104Lc-BglII primer
SEQ ID NO:44: The nucleotide sequence of 920104Lc-BsiWI primer
SEQ ID NO:45: The nucleotide sequence of 1126Hc-SalIU primer
SEQ ID NO:46: The nucleotide sequence of 1126Hc-NheIL primer
SEQ ID NO:47: The nucleotide sequence of 1126Lc-PmeIU primer
SEQ ID NO:48: The nucleotide sequence of 1126Lc-BsiWI primer
SEQ ID NO:49: The nucleotide sequence of 12511Hc-SalIU primer
SEQ ID NO:50: The nucleotide sequence of 12511Hc-NheIL primer
SEQ ID NO:51: The nucleotide sequence of 12511Lc-BglII primer
SEQ ID NO:52: The nucleotide sequence of 12511Lc-BsiWI primer

The invention claimed is:

1. An antibody or an antibody fragment thereof, wherein the antibody comprises an antibody heavy chain variable region ($V_H$) comprising SEQ ID NO: 81 and an antibody light chain variable region ($V_L$) comprising SEQ ID NO: 82, and wherein the antibody and antibody fragment thereof specifically bind to extracellular domain 4 of erbB3 consisting of amino acids 488 to 643 of SEQ ID NO: 3.

2. A pharmaceutical composition comprising the antibody or antibody fragment according to claim 1 and a pharmaceutically acceptable carrier.

3. An antibody composition comprising a first antibody or antibody fragment thereof according to claim 1 and a second antibody or antibody fragment thereof, wherein the second antibody and antibody fragment thereof bind to a domain of erbB3 that is not extracellular domain 4 of erbB3 consisting of amino acids 488 to 643 of SEQ ID NO: 3.

4. The antibody composition according to claim 3 wherein the second antibody or antibody fragment thereof binds with domain 1 or 3 in the extracellular domain of erbB3.

5. The antibody composition according to claim 3 wherein the second antibody comprises an antibody heavy chain variable region ($V_H$) comprising SEQ ID NO: 57 and an antibody light chain variable region ($V_L$) comprising SEQ ID NO: 58.

6. The antibody composition according to claim 3 wherein the second antibody comprises heavy chain complementary determining regions (CDRs) 1 to 3 comprising SEQ ID NOS: 59-61, respectively, and light chain CDRs 1 to 3 comprising SEQ ID NOS: 62-64, respectively.

7. A pharmaceutical composition comprising the antibody composition of claim 3 and a pharmaceutically acceptable carrier.

8. An antibody or an antibody fragment thereof, wherein the antibody and the antibody fragment comprise heavy chain complementary determining regions (CDRs) 1 to 3 comprising SEQ ID NOS: 83-85, respectively, and light chain CDRs 1 to 3 comprising SEQ ID NOS: 86-88, respectively, and wherein the antibody and antibody fragment thereof specifically bind to extracellular domain 4 of erbB3 consisting of amino acids 488 to 643 of SEQ ID NO: 3.

9. A pharmaceutical composition comprising the antibody or antibody fragment of claim 8 and a pharmaceutically acceptable carrier.

10. An antibody composition comprising a first antibody or antibody fragment thereof according to claim 8 and a second antibody or antibody fragment thereof, wherein the second antibody and antibody fragment thereof bind to a domain of erbB3 that is not extracellular domain 4 of erbB3 consisting of amino acids 488 to 643 of SEQ ID NO: 3.

11. The antibody composition according to claim 10 wherein the second antibody or antibody fragment thereof binds with domain 1 or 3 in the extracellular domain of erbB3.

12. The antibody composition according to claim 10 wherein the second antibody comprises an antibody heavy chain variable region ($V_H$) comprising SEQ ID NO: 57 and an antibody light chain variable region ($V_L$) comprising SEQ ID NO: 58.

13. The antibody composition according to claim 10 wherein the second antibody comprises heavy chain complementary determining regions (CDRs) 1 to 3 comprising SEQ ID NOS: 59-61, respectively, and light chain CDRs 1 to 3 comprising SEQ ID NOS: 62-64, respectively.

14. A pharmaceutical composition comprising the antibody composition of claim 10 and a pharmaceutically acceptable carrier.

* * * * *